United States Patent
Shishido et al.

(10) Patent No.: US 10,369,219 B2
(45) Date of Patent: Aug. 6, 2019

(54) COMPOSITION FOR ENHANCING INDUCTION OF HUMORAL IMMUNITY, AND VACCINE PHARMACEUTICAL COMPOSITION

(71) Applicant: NITTO DENKO CORPORATION, Osaka (JP)

(72) Inventors: Takuya Shishido, Osaka (JP); Daisuke Asari, Osaka (JP); Kyohei Matsushita, Osaka (JP); Mitsuhiko Hori, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 15/501,271

(22) PCT Filed: Aug. 4, 2015

(86) PCT No.: PCT/JP2015/072101
§ 371 (c)(1),
(2) Date: Feb. 2, 2017

(87) PCT Pub. No.: WO2016/021599
PCT Pub. Date: Feb. 11, 2016

(65) Prior Publication Data
US 2017/0216429 A1      Aug. 3, 2017

(30) Foreign Application Priority Data
Aug. 4, 2014 (JP) ................. 2014-158999

(51) Int. Cl.
| | | |
|---|---|---|
| *A61K 39/00* | (2006.01) | |
| *C07K 14/005* | (2006.01) | |
| *C07H 21/00* | (2006.01) | |
| *C07H 21/04* | (2006.01) | |
| *C12N 15/10* | (2006.01) | |
| *A61K 39/39* | (2006.01) | |

(52) U.S. Cl.
CPC ............ *A61K 39/39* (2013.01); *A61K 39/00* (2013.01); *A61K 2039/54* (2013.01); *A61K 2039/542* (2013.01); *A61K 2039/543* (2013.01); *A61K 2039/55511* (2013.01); *A61K 2039/575* (2013.01); *Y02A 50/388* (2018.01); *Y02A 50/39* (2018.01)

(58) Field of Classification Search
CPC ............ A61K 2300/00; A61K 2039/53; A61K 39/00; C07K 14/005; C12N 15/1027
See application file for complete search history.

(56) References Cited

U.S. PATENT DOCUMENTS

| 4,578,399 A | 3/1986 | Schorlemmer et al. |
| 2006/0233743 A1 | 10/2006 | Kelly |
| 2010/0278875 A1 | 11/2010 | Giles-Komar et al. |

FOREIGN PATENT DOCUMENTS

| JP | 59-205315 A | 11/1984 |
| JP | 2006-508936 A | 3/2006 |
| JP | 2010-505769 A | 2/2010 |
| WO | 2005097211 A2 | 10/2005 |
| WO | 2008/040009 A1 | 4/2008 |
| WO | WO2008040009 | * 4/2008 |

OTHER PUBLICATIONS

Rubtsova et al. "A study on the immunotropic activity of caffeine and theophylline as cAMP-phosphodiesterase inhibitors" (Farmakol Toksikol, 1986, 49(3):pdf 1-5).*
Nakano et al. "Dendriti cells inducing Th2 cells", Clinical Immunology & Allergology, 2009, 51(5):pdf pp. 1-10.*
Rubisova et al."The study of the immunotropic activity of cAMP phosphodiesterase inhibitors caffeine and theophylline", Farmakologiya Toksikologiya, 1986, pp. 74-77, vol. 49, No. 3.
Koh W. S. et al., "Cyclic AMP is essential factor in immune responses.", Biochemical and Biophysical Research Communications, 1995, pp. 703-709, vol. 206, No. 2.
Goren N. et al., "Increases in cyclic AMP levels couple to H1 receptors in atria from autoimmune myocarditis mice.", Cellular Signalling, 1995, pp. 759-764, vol. 7, No. 8.
Nakano et al., "CD4+ T-Saibo no kinotecki Agun eno Bunka Dendritic cells and Th2 differentiation", Clinical Immunology & Allergology, 2009, pp. 450-455, vol. 51, No. 5.
Lipscomb et al., "Dendritic Cells: Immune Regulators in Health and Disease", Physiol Rev., 2002, vol. 82, pp. 97-130.
Mazzoni et al., "Controlling the Toll road to dendritic cell polarization", Journal of Leukocyte Biology, 2004, vol. 75, pp. 721-730.
Stevceva et al., "Mucosal Adjuvants", Current Pharmaceutical Design, 2005, vol. 11, pp. 801-811.
Zhou et al., "Plasticity of CD4+ T Cell Lineage Differentiation", Immunity, 2009, pp. 646-655.
International Search Report issued with respect to Application No. PCT/JP2015/072101, dated Nov. 10, 2015.
International Preliminary Report on Patentability issued with respect to Application No. PCT/JP2015/072101, dated Feb. 7, 2017.
Katamura "Differentiation of naive human CD4+ T cells into Th2 cells: The role of prostaglandin E2", Allergology International, 1999, pp. 7-14, vol. 48.
Matsushita et al., "Adjuvants that Enhance Th2 or Tr Responses", Allergology International, 2005, pp. 507-513, vol. 54.
Extended European Search Report for Application No. 15828998.3 dated Dec. 21, 2017.
Office Action for EP App. No. 15 828 998.3 dated May 2, 2019.
Office Action for JP App. No. 2015-154344 dated Jun. 4, 2019 (w/ English-language translation).

* cited by examiner

*Primary Examiner* — Barry A Chestnut
(74) *Attorney, Agent, or Firm* — Greenblum & Bernstein, P.L.C.

(57) ABSTRACT

The present invention aims to provide a composition for promoting humoral immunity induction and a vaccine pharmaceutical composition that can be universally used for various antigens in inducing humoral immunity to antigens, contain a Th2 reaction promoter, and exerts a high humoral immunity inducing effect. The present invention relates to a vaccine pharmaceutical composition containing an antigen for humoral immunity induction and at least one Th2 reaction promoter.

3 Claims, 3 Drawing Sheets

COMPOSITION FOR ENHANCING INDUCTION OF HUMORAL IMMUNITY, AND VACCINE PHARMACEUTICAL COMPOSITION

TECHNICAL FIELD

The present invention relates to a composition for promoting humoral immunity induction containing a Th2 reaction promoter and a vaccine pharmaceutical composition for humoral immunity induction containing the composition for promoting humoral immunity induction.

BACKGROUND ART

Common widely used vaccines are made from pathogens (e.g., microorganisms, viruses) or such pathogens whose toxicity is partially weakened or eliminated. The vaccines are administered to living bodies to induce immunity to prevent infectious diseases.

Dendritic cells after having engulfed viruses, microorganisms, or like foreign bodies migrate to lymph nodes and give naive T cells (Th0 cells) the information of the foreign bodies, thus inducing the differentiation of helper T cells. Through the interaction with dendritic cells, Th0 cells differentiate into type 1 helper T cells (Th1 cells), which are responsible for cellular immunity, and type 2 helper T cells (Th2 cells), which are responsible for humoral immunity (see Non-Patent Literature 1, for example).

Many toll-like receptors (TLRs) are expressed in immunocompetent cells responsible for the innate immunity system, including dendritic cells. They are activated upon receiving a TLR ligand and promote the differentiation of helper T cells, thus inducing an effective immune reaction (see Non-Patent Literature 2, for example). For immunity activation, only the reaction routes via TLRs have been known, and other reaction routes have remained unclear.

It is known that the direction of the differentiation of helper T cells is controllable with biological signaling molecules such as cytokines. Such control is widely employed in in vitro testing systems. The dendritic cells are activated by stimuli such as cytokines and assumed to determine the direction of the helper T cell differentiation through complicated signal transduction. That is, the "state" of dendritic cells decides the differentiation of T cells, leading to the induction of the cellular immunity or the humoral immunity. The former, where Th 1 cells serve as the center of the reaction, is called Th1 reaction. Similarly, the latter is called Th2 reaction (see Non-Patent Literature 3, for example).

The promotion of immune reactions via TLRs as described above has been known, but promotion of a humoral immune response (Th2 reaction) via other reactions, that is, reactions not involving TLR stimuli by TLR ligands, has yet to be reported.

It is known that immunity activation effects can be given by toxins such as cholera toxin or *Escherichia coli* heat-labile enterotoxin or fat/oil adjuvants that enhance the effects of immune reactions by slow-release of antigens. However, they have problems in terms of the balance between the safety and the efficacy (see Non-Patent Literature 4, for example). Thus, adjuvants capable of activating immunity while ensuring safety are demanded.

CITATION LIST

Non Patent Literature

Non-Patent Literature 1: Lipscomb M F. et al., Physiol Rev., 82, 97-130 (2002)

Non-Patent Literature 2: Mazzoni A. et al., J Leukoc Biol., 75, 721-730 (2004)

Non-Patent Literature 3: Zhou L. et al., Immunity, 30, 646-655 (2009)

Non-Patent Literature 4: Stevceva L. et al., Curr Pharm Des, 11, 801-811 (2005)

SUMMARY OF INVENTION

Technical Problem

In view of the situation in the art mentioned above, the present invention aims to provide a composition for promoting humoral immunity induction and a vaccine pharmaceutical composition which are universally usable for various antigens in the induction of humoral immunity to antigens, contain a Th2 reaction promoter, and exert a high humoral immunity inducing effect.

Solution to Problem

The present inventors found out that applying an external stimulus to a dendritic cell using a specific drug when the cell engulfs an antigen can promote the Th2 reaction, allowing promotion of induction of humoral immunity. This is presumably because such a stimulus causes signal transduction in the dendritic cell to activate the cell, thus leading to induction of humoral immunity. This enables promotion of induction of humoral immunity via a reaction not involving a TLR stimulus by a TLR ligand.

Specifically, the above specific drug may be a drug that promotes the synthesis, or reduce the decomposition, of cyclic AMP (cAMP), which is responsible for signal transduction in cells, or a drug that suppresses a stimulus to phospholipase C (PLC).

Accordingly, the present invention found out that direct administration of a specific drug that promotes Th2 reaction together with or separately from an antigen to the same site or different sites of a living body enables effective induction of antigen-specific humoral immunity via a reaction not involving a TLR stimulus by a TLR ligand.

One aspect of the present invention provides a composition for promoting humoral immunity induction containing a Th2 reaction promoter.

The Th2 reaction promoter in the composition for promoting humoral immunity induction of the present invention is preferably at least one of a phosphodiesterase inhibitor or a G protein-coupled receptor ligand.

The Th2 reaction promoter of the composition for promoting humoral immunity induction of the present invention is preferably at least one selected from the group consisting of a drug that promote synthesis of cyclic AMP (cAMP), a drug that reduces decomposition of cyclic AMP (cAMP), and a drug that suppresses a stimulus to phospholipase C (PLC).

In the composition for promoting humoral immunity induction of the present invention, the drug that promotes synthesis of cyclic AMP (cAMP) is preferably at least one selected from the group consisting of an adrenergic receptor ligand, a muscarinic receptor ligand, a dopamine receptor ligand, a histamine receptor ligand, a serotonin receptor ligand, and a vasopressin receptor ligand, the drug that reduces decomposition of cyclic AMP (cAMP) is preferably at least one selected from the group consisting of a phosphodiesterase inhibitor, an adrenergic receptor ligand, a muscarinic receptor ligand, a dopamine receptor ligand, a histamine receptor ligand, a serotonin receptor ligand, a PAF receptor ligand, a purine receptor ligand, an opioid receptor ligand, a leukotriene receptor ligand, and an angiotensin receptor ligand, and the drug that suppresses a stimulus to phospholipase C (PLC) is preferably at least one selected from the group consisting of an adrenergic receptor ligand, a muscarinic receptor ligand, a histamine receptor ligand, a serotonin receptor ligand, a PAF receptor ligand, a vasopressin receptor ligand, a leukotriene receptor ligand, and an angiotensin receptor ligand.

Another aspect of the present invention provides a vaccine pharmaceutical composition containing an antigen for humoral immunity induction and the composition for promoting humoral immunity induction.

The vaccine pharmaceutical composition of the present invention is preferably administered to a body surface.

The vaccine pharmaceutical composition of the present invention is preferably administered by intradermal injection, subcutaneous injection, or intramuscular injection.

The present invention will be described below.

The composition for promoting humoral immunity induction and vaccine pharmaceutical composition of the present invention are used for humoral immunity induction.

The vaccine pharmaceutical composition of the present invention contains an antigen for inducing humoral immunity and the composition for promoting humoral immunity induction in combination, so that it can effectively induce humoral immunity. The antigen and the composition for promoting humoral immunity induction may be contained together in a formulation, or may be in different formulations and used in combination.

The humoral immunity inducing effect may be quantitatively determined by any method. Various methods have been developed. For example, the effect can be determined by an immunity induction test using an animal model for immunity evaluation and ELISA (antigen-specific IgG antibody). The sample for determining humoral immunity may be, for example, blood of the animal model for immunity evaluation.

As used herein, the term "composition for promoting humoral immunity induction" means any substance that can improve the efficiency to induce humoral immunity to an antigen administered with the substance, as compared to the efficiency obtained without the substance. The substance is not limited by the mechanism of promoting humoral immunity induction, but the term means those specified herein.

As used herein, the term "Th2 reaction promoter" means a substance that promotes the entire series of Th2 reactions that induce the differentiation of a Th0 cell into a Th2 cell for antibody production. Specifically, the term means a drug that increases cAMP or suppresses PLC.

The Th2 reaction promoter is preferably a phosphodiesterase inhibitor and/or a G protein-coupled receptor ligand. In the present invention, any G protein-coupled receptor ligand can be used, but preferably a G protein-coupled receptor agonist and/or a G protein-coupled receptor antagonist are/is used because in such a case a phosphodiesterase inhibitor or a ligand for a G protein-coupled receptor can be used to increase the intracellular cAMP concentration and an antagonist for a G protein-coupled receptor can be used to suppress PLC.

In one preferred embodiment, the composition for promoting humoral immunity induction contains the Th2 reaction promoter in which the drug that promotes synthesis of cyclic AMP (cAMP) is at least one selected from the group consisting of an adrenergic receptor ligand, a muscarinic receptor ligand, a dopamine receptor ligand, a histamine receptor ligand, a serotonin receptor ligand, and a vasopressin receptor ligand, the drug that reduces decomposition of cyclic AMP (cAMP) is at least one selected from the group consisting of a phosphodiesterase inhibitor, an adrenergic receptor ligand, a muscarinic receptor ligand, a dopamine receptor ligand, a histamine receptor ligand, a serotonin receptor ligand, a PAF receptor ligand, a purine receptor ligand, an opioid receptor ligand, a leukotriene receptor ligand, and an angiotensin receptor ligand, and the drug that suppresses a stimulus to phospholipase C (PLC) is at least one selected from the group consisting of an adrenergic receptor ligand, a muscarinic receptor ligand, a histamine receptor ligand, a serotonin receptor ligand, a PAF receptor ligand, a vasopressin receptor ligand, a leukotriene receptor ligand, and an angiotensin receptor ligand.

As used herein, the term "phosphodiesterase inhibitor" means a substance that inhibits the function of a phosphodiesterase (PDE) that decomposes cAMP. The phosphodiesterase inhibitor is also referred to as "PDE inhibitor". Some PDE inhibitors selectively act on specific phosphodiesterases (phosphodiesterases have subtypes such as PDE1 and PDE2.), and others have no selectivity. Examples of PDE inhibitors usable in the present invention include aminophylline, theophylline, pentoxifylline, proxyphylline, caffeine, IBMX, resveratrol, vinpocetine, EHNA, amrinone, milrinone, olprinone, cilostazol, enoximone, pimobendan, vesnarinone, bucladesine, quazinone, trequinsin, anagrelide, cilostamide, siguazodan, zardaverine, KMUP-1, RPL-554, rolipram, roflumilast, cilomilast, arofylline, ibudilast, denbutyline, drotaverine, etazolate, filaminast, glaucine, irsogladine, mesembrine, piclamilast, OPC6535, R020-1724, CP-80633, HT-0712, ICI-63197, RPL-554, YM-976, ASB16165, BRL50481, papaverine, tofisopam, SCH51866, dipyridamole, zaprinast, and derivatives thereof, and pharmacologically acceptable salts thereof. In a preferred embodiment of the present invention, the PDE inhibitor is resveratrol, vinpocetine, EHNA, cilostazol, pimobendan, BRL50481, and/or dipyridamole.

As used herein, the term "G protein-coupled receptor (GPCR)" herein means a substance which is a 7-transmembrane receptor localized in the cell membrane and is coupled to a G protein present on the inner side of the cell membrane so as to transduce signals in communication via extracellular neurotransmitters or the like. G proteins are trimeric proteins consisting of Gα, Gβ, and Gγ. Binding of a ligand to the GPCR causes dissociation into the GPCR, Gα, and a Gβγ complex. Gα is involved with an increase in cAMP and activation of PLC. Gα is largely divided into three subunits: Gs, which activates adenylate cyclase to promote the synthesis of cAMP; Gs, which suppresses the synthesis of cAMP; and Gq, which activates PLC. Accordingly, in order to increase cAMP, an agonist for a Gs-coupled GPCR or an antagonist for a Gi-coupled GPCR is used. In order to suppress PLC activation, an antagonist for a Gq-coupled GPCR is used.

In the present invention, the agonist for the G protein-coupled receptor and the antagonist for the G protein-coupled receptor are each at least one selected from the group consisting of an adrenergic receptor agonist, an adrenergic receptor antagonist, a muscarinic receptor agonist, a muscarinic receptor antagonist, a dopamine receptor agonist, a dopamine receptor antagonist, a histamine receptor agonist, a histamine receptor antagonist, a serotonin receptor agonist, a serotonin receptor antagonist, a PAF receptor antagonist, a purine receptor antagonist, a vasopressin receptor agonist, a vasopressin receptor antagonist, an opioid receptor antagonist, a leukotriene receptor antagonist, and an angiotensin receptor antagonist. Table 1 shows the types and subtypes of GPCRs for Th2 reaction promotion, Gα, and the relation of the GPCRs with agonists/antagonists.

TABLE 1

| GPCR | Subtype | Gα | Transduction mechanism | | Th2 promotion |
|---|---|---|---|---|---|
| Adrenaline | α1 | Gq | ↑ PLC | | Antagonist |
| | α2 | Gi | ↓ cAMP | | Antagonist |
| | β1,2,3 | Gs | ↑ cAMP | | Agonist |
| Muscarine | M1,3,5 | Gq | ↑ PLC | | Antagonist |
| | M2,4 | Gi | ↓ cAMP | | Antagonist |
| Dopamine | D1,5 | Gs | ↑ cAMP | | Agonist |
| | D2,3,4 | Gi | ↓ cAMP | | Antagonist |
| Histamine | H1 | Gq | ↑ PLC | | Antagonist |
| | H2 | Gs | ↑ cAMP | | Agonist |
| | H3,4 | Gi | ↓ cAMP | | Antagonist |
| Serotonin | 5-HT4,6,7 | Gs | ↑ cAMP | | Agonist |
| | 5-HT1,5 | Gi | ↓ cAMP | | Antagonist |
| | 5-HT2 | Gq | ↑ PLC | | Antagonist |
| PAF | — | Gi & Gq | ↓ cAMP | ↑ PLC | Antagonist |
| Purine | P2Y12 | Gi | ↓ cAMP | | Antagonist |
| Vasopressin | V1 | Gq | ↑ PLC | | Antagonist |
| | V2 | Gs | ↑ cAMP | | Agonist |
| Opioid | μ, κ, σ | Gi | ↓ cAMP | | Antagonist |
| Leukotriene | BLT | Gq & Gi | ↓ cAMP | ↑ PLC | Antagonist |
| | CysLT | Gi & Gq | ↓ cAMP | ↑ PLC | Antagonist |
| Angiotensin | AT1 | Gq | ↑ PLC | | Antagonist |
| | AT2 | Gi | ↓ cAMP | | Antagonist |

In the present invention, any adrenergic receptor ligand can be used. An adrenergic receptor agonist and/or an adrenergic receptor antagonist can preferably be used. As used herein, the term "adrenergic receptor agonist" means a substance that itself has a function to act on adrenergic receptors. Examples thereof include β1 receptor agonists, β2 receptor agonists, and β3 receptor agonists. Among the adrenergic receptor subtypes, β1, β2, and β3 are coupled to Gs.

As used herein, the term "adrenergic receptor antagonist" means a substance that itself has a function to inhibit action on adrenergic receptors. Examples thereof include α1 receptor antagonists and α2 receptor antagonists. Among the adrenergic receptor subtypes, al is coupled to Gq, and α2 is coupled to Gi.

As used herein, the term "β1 receptor agonist" means a substance that itself has a function to act on β1 receptors. The term "β2 receptor agonist" means a substance that itself has a function to act on β2 receptors. The term "β3 receptor agonist" means a substance that itself has a function to act on β3 receptors. Examples of the pi receptor agonists, β2 receptor agonists, and/or β3 receptor agonists include isoprenaline, dobutamine, ephedrine, cimaterol, denopamine, dipivefrine, isoxsuprine, ritodrine, fenoterol, orciprenaline, salbutamol, terbutaline, trimetoquinol, tulobuterol, salmeterol, formoterol, clenbuterol, procaterol, indacaterol, methoxyphenamine, clorprenaline, levarterenol, zinterol, amibegron, mirabegron, ritobegron, solabecron, BRL 37344, CL 316243, ICI 215001, SR 58611A, ZD 2079, ZD 7114, and derivatives thereof, and pharmacologically acceptable salts thereof.

As used herein, the term "α1 receptor antagonist" means a substance that itself has a function to inhibit action on al receptors. The term "α2 receptor antagonist" means a substance that itself has a function to inhibit action on α2 receptors. Examples of the al receptor antagonists and/or α2 receptor antagonists include tamsulosin, prazosin, indoramin, trimazosin, doxazosin, urapidil, ketanserin, phentolamine, tolazoline, nicergoline, moxisylyte, ifenprodil, alfuzosin, terazosin, silodosin, ergotamine, risperidone, mianserin, bunazosin, setiptiline, BE 2254, 2-MPMDQ, 2-PMDQ, Rec 15/2615, RS 100329, RS 17053, SNAP 5089, WB 4101, imiloxan, phenoxybenzamine, yohimbine, chlorpromazine, asenapine, mirtazapine, aptazapine, atipamezole, delequamine, setiptiline, A 80426, ARC 239, BRL 44408, efaroxan, idazoxan, imiloxan, JP 1302, rauwolscine, RS 79948, RX 821002, SKF 86466, spiroxatrine, and derivatives thereof, and pharmacologically acceptable salts thereof.

In the present invention, any muscarinic receptor ligand can be used. A muscarinic receptor antagonist can preferably be used.

As used herein, the term "muscarinic receptor antagonist" means a substance that itself has a function to inhibit action on muscarinic receptors. Examples thereof include M1 receptor antagonists, M2 receptor antagonists, M3 receptor antagonists, M4 receptor antagonists, and M5 receptor antagonists. Among the muscarinic receptor subtypes, M1, M3, and M5 are coupled to Gq, and M2 and M4 are coupled to Gi.

As used herein, the term "M1 receptor antagonist" means a substance that itself has a function to inhibit action on M1 receptors. The term "M2 receptor antagonist" means a substance that itself has a function to inhibit action on M2 receptors. The term "M3 receptor antagonist" means a substance that itself has a function to inhibit action on M3 receptors. The term "M4 receptor antagonist" means a substance that itself has a function to inhibit action on M4 receptors. The term "M5 receptor antagonist" means a substance that itself has a function to inhibit action on M5 receptors. Examples of the M1 receptor antagonists, M2 receptor antagonists, M3 receptor antagonists, M4 receptor antagonists and/or M5 receptor antagonists include trimebutine, piperidolate, propantheline, methanthelinium, tridihexethyl, isopropamide, hexocyclium, mepenzolate, tiemonium, prifinium, timepidium, scopolamine, atoropine, hyoscyamine, fentonium, cimetropium, propiverine, trospium, fesoterodine, orphenadrine, trihexyphenidyl, metixene, procyclidine, profenamine, dexetimide, mazaticol, benztropine, ethybenztropine, ipratropium, oxitropium, cyclopentolate, homatropine, acridinium, benzetimide, butropium, darotropium, diphenylpiperidinomethyldioxolan, diponium, etomidoline, eucatropine, flutropium, methylbenactyzium, methyloctatropine, oxapium, pipethanate, piroheptine, umeclidinium, valethamate, pirenzepine, dicycloverine, dicylomine, acotiamide, imidafenacin, biperiden, nitrocaramiphen, telenzepine, VU 0255035, oxybutynin, esoxybutynin, tripitramine, dimethindene, AF-DX 116, AF-DX 384, AQ-RA 741, oxyphencyclimine, camylofine, glycopyrronium, tolterodine, solifenacin, darifenacin, tiotropium, tiquizium, 4-DAMP, DAU 5884 hydrochloride, J 104129 fumarate, zamifenacin, tropicamide, PD 102807, and derivatives thereof, and pharmacologically acceptable salts thereof.

In the present invention, any dopamine receptor ligand can be used. A dopamine receptor agonist and/or a dopamine receptor antagonist can preferably be used.

As used herein, the term "dopamine receptor agonist" means a substance that itself has a function to act on dopamine receptors. Examples thereof include D1 receptor agonists and D5 receptor agonists. Among the dopamine receptor subtypes, D1 and D5 are coupled to Gs.

As used herein, the term "dopamine receptor antagonist" means a substance that itself has a function to inhibit action on dopamine receptors. Examples thereof include D2 receptor antagonists, D3 receptor antagonists, and D4 receptor antagonists. Among the dopamine receptor subtypes, D2, D3, and D4 are coupled to Gi.

As used herein, the term "D1 receptor agonist" means a substance that itself has a function to act on D1 receptors. The term "D5 receptor agonist" means a substance that itself has a function to act on D5 receptors. Examples of the D1 receptor agonists and/or the D5 receptor agonist include fenoldopam, adrogolide, A 68930 hydrochloride, A 77636 hydrochloride, CY 208-243, dihydrexidine hydrochloride, SKF 81297 hydrobromide, SKF 83822 hydrobromide, and derivatives thereof, and pharmacologically acceptable salts thereof.

As used herein, the term "D2 receptor antagonist" means a substance that itself has a function to inhibit action on D2 receptors. The term "D3 receptor antagonist" means a substance that itself has a function to inhibit action on D3 receptors. The term "D4 receptor antagonist" means a substance that itself has a function to inhibit action on D4 receptors. Examples of the D2 receptor antagonists, the D3 receptor antagonists, and/or D4 receptor antagonists include metoclopramide, domperidone, bromopride, alizapride, metopimazine, chlorpromazine, levomepromazine, promazine, triflupromazine, fluphenazine, perphenazine, prochlorperazine, thioridazine, haloperidol, trifluperidol, moperone, pipamperone, bromperidol, droperidol, molindone, sertindole, ziprasidone, pimozide, loxapine, clozapine, olanzapine, quetiapine, asenapine, sulpiride, sultopride, tiapride, remoxipride, levosulpiride, risperidone, mosapramine, zotepine, paliperidone, opipramol, aplindore, bifeprunox, blonanserin, cariprazine, clocapramine, iloperidone, mazapertine, methoxypromazine maleate, nemonapride, perospirone, piquindone, spiperone, timiperone, tiospirone, raclopride, eticlopride hydrochloride, GR 103691, nafadotride, NGB 2904, PG 01037 dihydrochloride, PNU 177864 hydrochloride, SB 277011A dihydrochloride, U 99194 maleate, fanaserin, sonepiprazole, L-741, 742 hydrochloride, L-745, 870 trihydrochloride, PD 168568 dihydrochloride, PNU 96415E, and derivatives thereof, and pharmacologically acceptable salts thereof.

In the present invention, any histamine receptor ligand can be used. A histamine receptor agonist and/or a histamine receptor antagonist can preferably be used.

As used herein, the term "histamine receptor agonist" means a substance that itself has a function to act on histamine receptors. Examples thereof include H2 receptor agonists. Among the histamine receptor subtypes, H2 is coupled to Gs.

As used herein, the term "histamine receptor antagonist" means a substance that itself has a function to inhibit action on histamine receptors. Examples thereof include H1 receptor antagonists, H3 receptor antagonists, and H4 receptor antagonists. Among the histamine receptor subtypes, H1 is coupled to Gq, and H3 and H4 are coupled to Gi.

As used herein, the term "H2 receptor agonist" means a substance that itself has a function to act on H2 receptors. Examples of the H2 receptor agonists include impromidine hydrochloride, amthamine dihydrobromide, dimaprit dihydrochloride, HTMT dimaleate, and derivatives thereof, and pharmacologically acceptable salts thereof.

As used herein, the term "H1 receptor antagonist" means a substance that itself has a function to inhibit action on H1 receptors. The term "H3 receptor antagonist" means a substance that itself has a function to inhibit action on H3 receptors. The term "H4 receptor antagonist" means a substance that itself has a function to inhibit action on H4 receptors. Examples of the H1 receptor antagonists, the H3 receptor antagonists, and/or the H4 receptor antagonists include ketanserin, thonzylamine, mepyramine, tripelennamine, promethazine, dimetindene, clemastine, bamipine, isothipendyl, diphenhydramine, chlorphenoxamine, dimetotiazine, hydroxyzine, cinnarizine, levocabastine, azelastine, antazoline, olopatadine, diphenylpyraline, carbinoxamine, doxylamine, brompheniramine, dexchlorpheniramine, chlorpheniramine, pheniramine, alimemazine, mequitazine, cyclizine, meclizine, oxatomide, cetirizine, levocetirizine, cyproheptadine, phenindamine, triprolidine, azatadine, astemizole, loratadine, ketotifen, acrivastine, ebastine, epinastine, fexofenadine, desloratadine, rupatadine, bilastine, emedastine, alcaftadine, bepotastine, dimenhydrinate, dioxopromethazine, homochlorcyclizine, icotidine, mizolastine, noberastine, rocastine, tecastemizole, temelastine, irdabisant, betahistine, thioperamide, BF 2649 hydrochloride, burimamide oxalate, carcinine ditrifluoroacetate, clobenpropit dihydrobromide, conessine, GT 2016, impentamine dihydrobromide, iodophenpropit dihydrobromide, JNJ 10181457 dihydrochloride, JNJ 5207852 dihydrochloride, ROS 234 dioxalate, SEN 12333, VUF 5681 dihydrobromide, A 943931 dihydrochloride, A 987306, JNJ 10191584 maleate, JNJ 7777120, and derivatives thereof, and pharmacologically acceptable salts thereof.

In the present invention, any serotonin receptor ligand can be used. A serotonin receptor agonist and/or serotonin receptor antagonist can preferably be used.

As used herein, the term "serotonin receptor agonist" means a substance that itself has a function to act on serotonin receptors. Examples thereof include κ-HT4 receptor agonists, 5-HT6 receptor agonists, and 5-HT7 receptor agonists. Among the serotonin receptor subtypes, 5-HT4, 5-HT6, and 5-HT7 are coupled to Gs.

As used herein, the term "serotonin receptor antagonist" means a substance that itself has a function to inhibit action on serotonin receptors. Examples thereof include κ-HT1 receptor antagonists, 5-HT2 receptor antagonists, and 5-HT5 receptor antagonists. Among the serotonin receptor subtypes, 5-HT1 and 5-HT5 are coupled to Gi, and 5-HT2 is coupled to Gq.

As used herein, the term "5-HT4 receptor agonist" means a substance that itself has a function to act on 5-HT4 receptors. The term "5-HT6 receptor agonist" means a substance that itself has a function to act on 5-HT6 receptors. The term "5-HT7 receptor agonist" means a substance that itself has a function to act on 5-HT7 receptors. Examples of the 5-HT4 receptor agonists, the 5-HT6 receptor agonists, and/or the 5-HT7 receptor agonists include tegaserod, prucalopride, cisapride, mosapride, naronapride, renzapride, velusetrag, zacopride, BIMU 8, benzothiazole, EMD 386088, EMDT, ST 1936, WAY 208466, AS 19, LP 12, LP 44, and derivatives thereof, and pharmacologically acceptable salts thereof.

As used herein, the term "5-HT1 receptor antagonist" means a substance that itself has a function to inhibit action on 5-HT1 receptors. The term "5-HT2 receptor antagonist" means a substance that itself has a function to inhibit action on 5-HT2 receptors. The term "5-HT5 receptor antagonist" means a substance that itself has a function to inhibit action on 5-HT5 receptors. Examples of the 5-HT1 receptor antagonists, the 5-HT2 receptor antagonists, and/or the 5-HT5 receptor antagonists include elzasonan, lecozotan, alprenolol, cyanopindolol, MM 77, NAD 299, NAN-190, pindolol, SDZ 21009, spiroxatrine, (S)-WAY 100135, WAY 100635, GR 127935, GR 55562, isamoltane, LY 393558, NAS-181, SB 216641, SB 224289, BRL 15572, LY 310762, dimetotiazine, levomepromazine, asenapine, chlorpromazine, ziprasidone, opipramol, mianserin, mirtazapine, cinanserin, glemanserin, metrenperone, pelanserin, setiptiline, tropanserin, ketanserin, naftidrofuryl, pizotifen, risperidone, pipamperone, sertindole, clozapine, olanzapine, quetiapine, mosapramine, zotepine, paliperidone, trazodone, nefazodone, altanserin, amesergide, blonanserin, eplivanserin, fananserin, iloperidone, lubazodone, perospirone, pimavanserin, pruvanserin, ritanserin, sarpogrelate, spiperone, temanogrel, AT 1015, dimethyltryptamine, DV 7028, EMD 281014, 4F 4PP, MDL 11, 939, melperone, mesulergine, ATC 0175, LY 266097, LY 272015, RS 127445, SB 200646, SB 204741, SB 206553, SB 221284, SB 228357, SDZ SER 082, methysergide, agomelatine, tedatioxetine, RS 102221, S 32212, SB 242084, SB 243213, and derivatives thereof, and pharmacologically acceptable salts thereof.

In the present invention, any PAF receptor ligand can be used. A PAF receptor antagonist can preferably be used.

As used herein, the term "PAF receptor antagonist" means a substance that itself has a function to inhibit action on platelet-activating factor (PAF) receptors. Examples of the PAF receptor antagonist include apafant, israpafant, lexipafant, ginkgolide B, PCA 4248, and derivatives thereof, and pharmacologically acceptable salts thereof. The PAF receptor is coupled to Gi and Gq.

In the present invention, any purine receptor ligand can be used. A purine receptor antagonist can preferably be used.

As used herein, the term "purine receptor antagonist" means a substance that itself has a function to inhibit action on purine receptors. Examples thereof include P2Y12 receptor antagonists. Among the purine receptor subtypes, P2Y12 is coupled to Gi.

As used herein, the term "P2Y12 receptor antagonist" means a substance that itself has a function to inhibit action on P2Y12 receptors. Examples of the P2Y12 receptor antagonists include clopidogrel, ticlopidine, prasugrel, ticagrelor, cangrelor, elinogrel, and derivatives thereof, and pharmacologically acceptable salts thereof.

In the present invention, any vasopressin receptor ligand can be used. A vasopressin receptor agonist and/or vasopressin receptor antagonist can preferably be used.

As used herein, the term "vasopressin receptor agonist" means a substance that itself has a function to act on vasopressin receptors. Examples thereof include V2 receptor agonists. Among the vasopressin receptor subtypes, V2 is coupled to Gs.

As used herein, the term "vasopressin receptor antagonist" means a substance that itself has a function to inhibit action on vasopressin receptors. Examples thereof include V1 receptor antagonists. Among the vasopressin receptor subtypes, V1 is coupled to Gq.

As used herein, the term "V2 receptor agonist" means a substance that itself has a function to act on V2 receptors. Examples of the V2 receptor agonists include vasopressin, desmopressin, lypressin, terlipressin, ornipressin, argipressin, and derivatives thereof, and pharmacologically acceptable salts thereof.

As used herein, the term "V1 receptor antagonist" means a substance that itself has a function to inhibit action on V1 receptors. Examples of the V1 receptor antagonists include OPC 21268, SR 49059, and derivatives thereof, and pharmacologically acceptable salts thereof.

In the present invention, any opioid receptor ligand can be used. An opioid receptor antagonist can preferably be used.

As used herein, the term "opioid receptor antagonist" means a substance that itself has a function to inhibit action on opioid receptors. Examples thereof include μ receptor antagonists, κ receptor antagonists, and δ receptor antagonists. Among the opioid receptor subtypes, μ, κ, and δ are coupled to Gi.

As used herein, the term "μ receptor antagonist" means a substance that itself has a function to inhibit action on μ receptors. As used herein, the term "κ receptor antagonist" means a substance that itself has a function to inhibit action on κ receptors. As used herein, the term "δ receptor antagonist" means a substance that itself has a function to inhibit action on δ receptors. Examples of the μ receptor antagonists, the κ receptor antagonists, and/or the δ receptor antagonists include alvimopan, nalbuphine, naltrexone, nalorphine, naloxone, cyclazocine, eptazocine, naldemedine, quadazocine, clocinnamox, cyprodime, β-funaltrexamine, naloxonazine, binaltorphimine, DIPPA, GNTI, ML 190, rimcazole, benzylnaltrindole, BNTX, naltriben, naltrindole, SDM25N, and derivatives thereof, and pharmacologically acceptable salts thereof.

In the present invention, any leukotriene receptor ligand can be used. A leukotriene receptor antagonist can preferably be used.

As used herein, the term "leukotriene receptor antagonist" means a substance that itself has a function to inhibit action on leukotriene receptors. Examples thereof include BLT receptor antagonists and CysLT receptor antagonists. Among the leukotriene receptor subtypes, BLT and CysLT are coupled to Gi and Gq.

As used herein, the term "BLT receptor antagonist" means a substance that itself has a function to inhibit action on BLT receptors. As used herein, the term "CysLT receptor antagonist" means a substance that itself has a function to inhibit action on CysLT receptors. Examples of the BLT receptor antagonists and/or the CysLT receptor antagonists include LY 255283, zafirlukast, pranlukast, montelukast, ablukast, pobilukast edamine, ritolukast, sulukast, tipelukast, tomelukast, verlukast, and derivatives thereof, and pharmacologically acceptable salts thereof.

In the present invention, any angiotensin receptor ligand can be used. An angiotensin receptor antagonist can preferably be used.

As used herein, the term "angiotensin receptor antagonist" means a substance that itself has a function to inhibit action on angiotensin receptors. Examples thereof include AT1 receptor antagonists and AT2 receptor antagonists. Among the angiotensin receptor subtypes, AT1 is coupled to Gq, and AT2 is coupled to Gi.

As used herein, the term "AT1 receptor antagonist" means a substance that itself has a function to inhibit action on AT1 receptors. As used herein, the term "AT2 receptor antagonist" means a substance that itself has a function to inhibit action on AT2 receptors. Examples of the AT1 receptor antagonists and/or the AT2 receptor antagonists include losartan potassium, eprosartan, valsartan, irbesartan, candesartan, telmisartan, olmesartan, azilsartan, forasartan, saralasin acetate, PD 123319, and derivatives thereof, and pharmacologically acceptable salts thereof.

The vaccine pharmaceutical composition of the present invention contains at least one antigen and the composition for promoting humoral immunity induction.

As used herein, the term "antigen" means any substance that can induce an immune response. Any antigen may be used. Examples thereof include infectious disease-derived antigens.

As used herein, the term "infectious disease-derived antigen" means an infectious pathogen or a component thereof or any substance derived from thereof, capable of inducing an immune response (e.g., maturation of an immunocompetent cell, increase in cytokine production, promotion of antibody production). An infectious disease can be addressed (for example, treated or prevented) by administering the infectious disease-derived antigen with the composition for promoting humoral immunity induction to a subject using the pharmaceutical composition of the present invention.

As used herein, the term "infectious disease" means a disease caused by infection with an infectious pathogen or multiplication of an infectious pathogen.

The infectious disease is not limited. Examples thereof include virus diseases such as diseases caused by infection with adenovirus (e.g., human adenovirus), herpesvirus (e.g., herpes simplex virus, varicella-zoster virus, cytomegalovirus, human herpesvirus, Kaposi sarcoma-associated herpesvirus), picornavirus (e.g., poliovirus, common cold virus, hepatitis A virus), poxvirus (e.g., smallpox virus, vaccinia virus, molluscum contagiosum virus), picornavirus (e.g., rhinovirus, enterovirus), orthomyxovirus (e.g., influenza virus), paramyxovirus (e.g., parainfluenza virus, mumps virus, measles virus, respiratory syncytial virus (RSV), Newcastle disease virus), parvovirus (e.g., adeno associated virus), togavirus (e.g., rubella virus), coronavirus (e.g., SARS coronavirus), hepadnavirus (e.g., hepatitis B virus), flavivirus (e.g., Japanese encephalitis virus, yellow fever virus, dengue virus, West Nile fever virus, St. Louis encephalitis virus, Murray Valley encephalitis virus, hepatitis C virus, hepatitis G virus), hepevirus (e.g., hepatitis E virus), papillomavirus (e.g., human papilloma virus), calicivirus (e.g., norovirus), rhabdovirus (e.g., rabies virus, vesicular stomatitis virus), filovirus (e.g., Ebola hemorrhagic fever virus), arenavirus (e.g., Lassa virus, hepatitis D virus), bunyavirus (e.g., California encephalitis virus, Rift Valley fever virus), reovirus (e.g., rotavirus), or retrovirus (e.g., human immunodeficiency virus (HIV), adult T-cell leukemia virus); bacterial diseases such as those caused by infection with a bacterium such as *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococci, Neisseria, Clostridium, Bacillus, Corynebacterium, Mycobacterium, Campyrobacter, Vibrio, Serratia, Providencia, Chromobacterium, Brucella, Yersinia, Haemophilus*, or *Bordetella*; fungous diseases such as *chlamydia*, candidiasis, aspergillosis, histoplasmosis, and cryptococcal meningitis; malaria; *pneumocystis carinii* pneumonia; leishmaniasis; cryptosporidiosis; toxoplasmosis; and *Trypanosoma* infection.

The amount of the Th2 reaction promoter in the composition for promoting humoral immunity induction of the present invention is not limited. The amount is preferably 0.0001 to 100% by weight, more preferably 0.001 to 80% by weight, still more preferably 0.1 to 50% by weight, most preferably 0.05 to 20% by weight based on the total weight of the composition.

The amount of the antigen in the vaccine pharmaceutical composition of the present invention is not limited. The amount is preferably 0.000001 to 50% by weight, more preferably 0.00001 to 20% by weight based on the total weight of the composition.

The amount of the Th2 reaction promoter in the vaccine pharmaceutical composition of the present invention is not limited. The amount is preferably 0.001 to 10000 parts by weight, more preferably 0.01 to 10000 parts by weight based on 1 part by weight of the antigen.

If the amount of the Th2 reaction promoter is less than 0.001 parts by weight, the immunity inducing effect may be insufficient. If the amount is more than 10000 parts by weight, the vaccine pharmaceutical composition may cause safety issues.

The composition for promoting humoral immunity induction and vaccine pharmaceutical composition of the present invention may contain additive(s), if necessary. The additives can be selected from isotonizing agents, antiseptics, antioxidants, resolvents, solubilizing agents, suspending agents, fillers, pH adjusters, stabilizers, absorption promoters, release-rate controlling agents, colorants, plasticizers, crosslinking agents, and adhesives depending on, for example, the main components of the base, the compatibility with the antigen and the composition for promoting humoral immunity induction, or intended administration regimen. These additives may be used alone or in combination of two or more thereof.

The composition for promoting humoral immunity induction and vaccine pharmaceutical composition of the present invention may be intradermally, subcutaneously, or intramuscularly administered. They also may be administered to the body surface. The administration to the body surface may be transdermal administration or transmucosal administration. Accordingly, the composition for promoting humoral immunity induction and vaccine pharmaceutical composition of the present invention may be a vaccine pharmaceutical composition for intradermal, subcutaneous, or intramuscular administration, or may be a vaccine pharmaceutical composition for transdermal administration or transmucosal administration. The transdermal administration may be noninvasive or minimally invasive.

Injections cause pain, fear, and injection scars with subsequent cicatrization, putting a psychological burden on patients. When repetitive administrations are required, regular hospital visits put a burden on patient life. For the QOL of patients, consideration needs to be given to these burdens. Consideration also needs to be given to the fact that injections are permitted only for health care workers, that the intradermal injection, which has high immune effects, requires difficult manipulation, that health care workers have a risk of infection via needle stick injury, and that injections generates medical waste requiring specific waste treatment, such as injection needles. In view of this, the composition for promoting humoral immunity induction and the vaccine pharmaceutical composition are preferably administered to the body surface.

As used herein, the term "subject" means any animal to which the vaccine pharmaceutical composition at a practical stage can be administered so as to induce an immune response. The term typically means mammals including human, mouse, rat, canine, feline, leporine, equine, bovine, ovine, porcine, caprine, simian, and chimpanzee. The subject is particularly preferably a human.

<Vaccine Pharmaceutical Composition for Intradermal, Subcutaneous, or Intramuscular Administration>

The vaccine pharmaceutical composition for intradermal, subcutaneous, or intramuscular administration of the present invention exerts a high humoral immunity inducing effect in intradermal, subcutaneous, or intramuscular administration of various antigens to the subject. In particular for immunity for prevention of infectious diseases, vaccines can be easily invasively administered to the inside of the body because the intrusion of microorganisms or viruses through the skin is usually prevented due to their size.

As used herein, the term "for intradermal, subcutaneous, or intramuscular administration" in the pharmaceutical composition for intradermal, subcutaneous, or intramuscular administration refers to any form that has a certain degree of fluidity that allows administration by injection, such as a solution, a suspension, or a cream. The categories, definition, characteristics, production processes, and the like of these compositions are well known in the art. See the Japanese Pharmacopoeia 16th edition, for example.

The solvent for solutions may be, for example, an appropriate amount water or saline, ethanol, glycerin, or propylene glycol. A solution can be prepared by dispersing or dissolving components into the solvent.

Examples of the base usable for aqueous suspensions include hydrogel bases, such as carboxyvinyl polymers, gel bases, fat-free ointment, polyvinylpyrrolidone, polyvinyl alcohol, sodium polyacrylate, carboxymethylcellulose, starch, xanthan gum, karaya gum, sodium alginate, methylcellulose, hydroxypropylcellulose, hydroxypropylmethylcellulose phthalate (HPMCP), cellulose acetate phthalate (CAP), carboxymethylethylcellulose (CMEC), ethylcellulose, hydroxyethylcellulose, hydroxypropylmethylcellulose, carboxyvinyl polymers, tragacanth, gum arabic, tara gum, tamarind seed gum, *psyllium* seed gum, agar, gellan gum, glucomannan, locust bean gum, guar gum, carrageenan, dextrin, dextran, amylose, potassium carboxymethylcellulose, sodium carboxymethylcellulose, calcium carboxymethylcellulose, pullulan, chitosan, sodium carboxymethyl starch, *Plantago* testa, galactomannan, Eudragit, casein, alkyl alginate, gelatin, and polyethylene glycol. A fluidic suspension can be prepared by dissolving any of these bases into a solvent. The solvent is preferably saline, but glycerin or propylene glycol can also be used.

Examples of the base for hydrophobic suspensions include water/oil-type bases such as hydrophilic ointment and vanishing cream; and oil/water-type bases such as hydrophilic Vaseline, purified lanolin, Aquahole, Eucerin, Neocerin, hydrous lanolin, cold cream, and hydrophilic plastibase. A fat/oil suspension can be prepared by placing any of these bases into a fat/oil solvent or water and stirring the mixture at a high speed with, for example, a homogenizer.

<Composition for Promoting Humoral Immunity Induction for Intradermal, Subcutaneous, or Intramuscular Administration>

The composition for promoting humoral immunity induction for intradermal, subcutaneous, or intramuscular administration according to the present invention allows, in intradermal, subcutaneous, or intramuscular administration of various Th2 reaction promoters to the subject, more effective exertion of the humoral immunity induced by various antigens administered together with or separately from the TH2 reaction promoters.

As used herein, the term "for intradermal, subcutaneous, or intramuscular administration" in the composition for promoting humoral immunity induction for intradermal, subcutaneous, or intramuscular administration refers to any form that has a certain degree of fluidity that allows administration by injection, such as a solution, a suspension, a cream. The categories, definition, characteristics, production processes, and the like of these compositions are well known in the art. See the Japanese Pharmacopoeia 16th edition, for example.

For the above formulations, the same materials as those used for preparing the vaccine pharmaceutical composition for intradermal, subcutaneous, or intramuscular administration can be used.

<Vaccine Pharmaceutical Composition for Mucosal Administration>

The vaccine pharmaceutical composition for mucosal administration of the present invention exerts a high humoral immunity inducing effect in mucosal administration of various antigens to the subject.

As used herein, the term "for mucosal administration" in the pharmaceutical composition for mucosal administration may refer to any formulation usually used for mucosal administration, for example, sublingual, transnasal, buccal, rectal, or vaginal administration. Examples of such formulations include semisolid formulations such as gels (jellies), creams, ointments, and plasters, solutions, solid formulations such as powders, fine granules, granules, films, tablets, and orally disintegrating tablets, mucosal sprays such as aerosols, and inhalants. The categories, definition, characteristics, production processes, and the like of these compositions are well known in the art. See the Japanese Pharmacopoeia 16th edition, for example.

The solvent for solutions may be, for example, an appropriate amount of water or ethanol, glycerin, or propylene glycol. A solution can be prepared by dispersing or dissolving components in the solvent.

Examples of the base for gels (jellies) include hydrogel bases, such as carboxyvinyl polymers, gel bases, fat-free ointment, polyvinylpyrrolidone, polyvinyl alcohol, sodium polyacrylate, carboxymethylcellulose, starch, xanthan gum, karaya gum, sodium alginate, methylcellulose, hydroxypropylcellulose, hydroxypropylmethylcellulose phthalate (HPMCP), cellulose acetate phthalate (CAP), carboxymethylethylcellulose (CMEC), ethylcellulose, hydroxyethylcellulose, hydroxypropylmethylcellulose, carboxyvinyl polymers, tragacanth, gum arabic, tara gum, tamarind seed gum, *psyllium* seed gum, agar, gellan gum, glucomannan, locust bean gum, guar gum, carrageenan, dextrin, dextran, amylose, potassium carboxymethylcellulose, sodium carboxymethylcellulose, calcium carboxymethylcellulose, pullulan, chitosan, sodium carboxymethyl starch, *Plantago* testa, galactomannan, Eudragit, casein, alkyl alginate, gelatin, and polyethylene glycol. A fluid gel or a gel with formability can be prepared by dissolving any of these bases into a solvent. The solvent is preferably water, but glycerin or propylene glycol can also be used.

Examples of the base for creams include water/oil-type bases such as hydrophilic ointment and vanishing cream; and oil/water-type bases such as hydrophilic Vaseline, purified lanolin, Aquahole, Eucerin, Neocerin, hydrous lanolin, cold cream, hydrophilic plastibase. A cream can be prepared by placing any of these bases into a fat/oil solvent or water and stirring the mixture at a high speed with, for example, a homogenizer.

Examples of the base for films include polyvinylpyrrolidone, polyvinyl alcohol, sodium polyacrylate, carboxymethylcellulose, starch, xanthan gum, karaya gum, sodium alginate, methylcellulose, carboxyvinyl polymers, agar, hydroxypropylcellulose, hydroxypropylmethylcellulose phthalate (HPMCP), cellulose acetate phthalate (CAP), carboxymethylethylcellulose (CMEC), ethylcellulose, hydroxyethylcellulose, hydroxypropylmethylcellulose, carboxyvinyl polymers, tragacanth, gum arabic, locust bean gum, guar gum, carrageenan, dextrin, dextran, amylose, potassium carboxymethylcellulose, sodium carboxymethylcellulose, calcium carboxymethylcellulose, pullulan, chitosan, sodium carboxymethyl starch, *Plantago* testa, galactomannan, aminoalkyl methacrylate copolymer E, aminoalkyl methacrylate copolymer RS, methacrylic acid copolymer L, methacrylic acid copolymer LD, methacrylic acid copolymer S, methyl acrylate-methacrylic acid-methyl methacrylate copolymer, ethyl acrylate-methyl methacrylate copolymer, polyvinyl acetal diethylamino acetate, casein, and alkyl alginate. A film can be prepared by dissolving any of these bases in a polar organic solvent such as water or ethanol, applying the solution to form a thin film, and drying the film. In one preferred embodiment, the vaccine pharmaceutical composition of the present invention for mucosal administration is in the form of a film formulation.

Examples of additives for powders, fine granules, granules, and tablets include excipients such as lactose, corn starch, and crystalline cellulose, and binders such as hydroxypropylcellulose and gum arabic. Powder, fine granules, granules, and tablets can be prepared by mixing and stirring these additives with an appropriate amount of solvent such as water or ethanol and then subjecting the resulting mixture to a combination of processes such as granulation, drying, and tablet compression. If necessary, a lubricant such as magnesium stearate and a coating agent such as hydroxypropylcellulose or sucrose may be added.

Examples of the base for orally disintegrating tablets (freeze dry type) include polysaccharides such as gelatin and pullulan. Forming aids such as mannitol, trehalose, sorbitol, or glycine may also be used. An orally disintegrating tablet (freeze dry type) can be prepared by dissolving these additives in water, dispensing the solution, and then freeze drying it. In one preferred embodiment, the vaccine pharmaceutical composition for mucosal administration of the present invention is in the form of an orally disintegrating tablet.

The content of the aerosol may be, for example, a solution, a highly fluidic gel, a cream, or fine powder such as a powdered drug. Dispersing them as solid or liquid microparticles in a gas using a spray device enables effective administration to an administration site such as the oral mucosa or the nasal mucosa.

<Composition for Promoting Humoral Immunity Induction for Mucosal Administration>

The composition for promoting humoral immunity induction for mucosal administration according to the present invention allows, in mucosal administration of various Th2 reaction promoters to the subject, more effective exertion of humoral immunity induced by various antigens administered together with or separately from the TH2 reaction promoters.

As used herein, the term "for mucosal administration" in the composition for promoting humoral immunity induction for mucosal administration may refer to any formulation usually used for mucosal administration, such as sublingual, transnasal, buccal, rectal, or vaginal administration. Examples of such a formulation include semisolid formulations such as gels (jellies), creams, ointment, plasters, solutions, solid formulations such as powders, fine granules, granules, films, tablets, and orally disintegrating tablets, mucosal sprays such as aerosols, and inhalants. The categories, definition, characteristics, production processes, and the like of the compositions are well known in the art. See the Japanese Pharmacopoeia 16th edition, for example.

For the above formulations, the same materials as those used for preparing the vaccine pharmaceutical composition for mucosal administration can be used.

<Vaccine Pharmaceutical Composition for Transdermal Administration>

As used herein, the term "for transdermal administration" in the pharmaceutical composition for transdermal administration may refer to any formulation usually used for transdermal administration. Examples thereof include solutions for external use such as liniments and lotions, sprays for external use such as aerosols, ointments, plasters, creams, gels, and patches such as tapes or poultices. The categories, definition, characteristics, production processes, and the like of the compositions are well known in the art. See the Japanese Pharmacopoeia 16th edition, for example.

Examples of the base for liniments include water, ethanol, fatty oils such as hard paraffin, soft paraffin, liquid paraffin, glycerin, paraffin oil, beeswax, or metallic soap; mucilage; natural oils [e.g., almond oil, corn oil, peanut oil, castor oil, olive oil, derivatives thereof (e.g., polyoxyl castor oil)]; mutton tallow or derivatives thereof, and fatty acids and/or esters (e.g., stearic acid, oleic acid, isopropyl myristate).

Lotion is a formulation containing an active ingredient finely and homogenously dispersed in an aqueous liquid and classified into suspension lotion and emulsion lotion. The suspending agent may be, for example, gum arabic, sodium alginate, sodium carboxymethylcellulose, methylcellulose, or bentonite. The emulsifier may be, for example, sodium lauryl sulfate or sorbitan fatty acid ester.

Examples of the base usable for ointments include common hydrophobic bases such as fats and oils, waxes, and hydrocarbon compounds. Specific examples include mineral bases such as yellow Vaseline, white Vaseline, paraffin, liquid paraffin, plastibase, and silicone, and animal or vegetable bases such as beeswax and animal or vegetable oils and fats.

Examples of the base for creams include water/oil type bases such as hydrophilic ointment and vanishing cream; and oil/water type bases such as hydrophilic Vaseline, purified lanolin, Aquahole, Eucerin, Neocerin, hydrous lanolin, cold cream, and hydrophilic plastibase.

Examples of gel bases include hydrogel bases such as carboxyvinyl polymers, gel bases, fat-free ointment, polyvinylpyrrolidone, polyvinyl alcohol, sodium polyacrylate, carboxymethylcellulose, starch, xanthan gum, karaya gum, sodium alginate, methylcellulose, hydroxypropylcellulose, hydroxypropylmethylcellulose phthalate (HPMCP), cellulose acetate phthalate (CAP), carboxymethylethylcellulose (CMEC), ethylcellulose, hydroxyethylcellulose, hydroxypropylmethylcellulose, carboxyvinyl polymer, tragacanth, gum arabic, tara gum, tamarind seed gum, *psyllium* seed gum, agar, gellan gum, glucomannan, locust bean gum, guar gum, carrageenan, dextrin, dextran, amylose, potassium carboxymethylcellulose, sodium carboxymethylcellulose, calcium carboxymethylcellulose, pullulan, chitosan, sodium carboxymethyl starch, *Plantago* testa, galactomannan, aminoalkyl methacrylate copolymer E, aminoalkyl methacrylate copolymer RS, methacrylic acid copolymer L, methacrylic acid copolymer LD, methacrylic acid copolymer S, methyl acrylate-methacrylic acid-methyl methacrylate copolymer, ethyl acrylate-methyl methacrylate copolymer, polyvinyl acetal diethylamino acetate, casein, alkyl alginate, gelatin, and polyethylene glycol.

Examples of the base for poultices include gelatin, sodium carboxymethylcellulose, methylcellulose, sodium polyacrylate, kaolin, polyvinyl alcohol, polyvinylpyrrolidone, glycerin, propylene glycol, and water.

A tape includes, for example, an adhesive layer and a support for supporting the adhesive layer. The adhesive layer includes, for example, an acrylic adhesive, a natural rubber adhesive, a synthetic rubber adhesive (including rubber elastomers such as synthetic isoprene rubber, polyisobutylene (PIB), styrene-butadiene rubber, and styrene-isoprene-styrene (SIS) rubber), a silicone adhesive, a vinyl ester adhesive, or a vinyl ether adhesive. If desired, the tape may include a release liner that prevents exposure of the adhesive layer before use and can be easily peeled when the tape is used.

The adhesive to constitute the adhesive layer of the tape according to the present invention is not limited. Examples thereof include acrylic adhesives containing an acrylic polymer; rubber adhesives containing a rubber elastomer such as a styrene-diene-styrene block copolymer (e.g., styrene-isoprene-styrene block copolymer, styrene-butadiene-styrene block copolymer), polyisoprene, polyisobutylene, butyl rubber, or polybutadiene; silicone adhesives such as silicone rubber, dimethyl siloxane-based adhesives, and diphenyl siloxane-based adhesives; vinyl ether adhesives such as polyvinyl methyl ether, polyvinyl ethyl ether, and polyvinyl isobutyl ether; vinyl ester adhesives such as vinyl acetate-ethylene copolymer; and polyester adhesives containing a carboxylic acid component (e.g., dimethyl terephthalate, dimethyl isophthalate, dimethyl phthalate) and a polyalcohol component (e.g., ethylene glycol). Particularly preferred adhesives are acrylic adhesives, rubber adhesives, and silicone adhesives. The adhesive layer preferably contains the adhesive(s) in an amount of 10 to 90% by weight, more preferably 20 to 80% by weight in terms of solids, based on the total weight of the adhesive layer.

Examples of the acrylic adhesives include acrylate adhesives mainly composed of a polymer containing a C2-C18 alkyl (meth)acrylate as a first monomer. Examples of the alkyl (meth)acrylate (first monomer) include alkyl (meth)acrylates having a C1-C18 linear, branched, or cyclic alkyl group (e.g., methyl, ethyl, propyl, butyl, pentyl, hexyl, cyclohexyl, heptyl, octyl, 2-ethylhexyl, nonyl, decyl, undecyl, dodecyl, tridecyl), with alkyl (meth)acrylates having a C4-C18 linear, branched, or cyclic alkyl group (e.g., butyl, pentyl, hexyl, cyclohexyl, heptyl, octyl, 2-ethylhexyl, nonyl, decyl, undecyl, dodecyl, tridecyl) being preferred. Moreover, alkyl (meth)acrylates having a C4-C8 linear, branched, or cyclic alkyl group (e.g., butyl, pentyl, hexyl, cyclohexyl, heptyl, octyl, or 2-ethylhexyl, preferably butyl, 2-ethylhexyl, or cyclohexyl, particularly preferably 2-ethylhexyl) because the use of a monomer component that lowers the glass transition temperature of the polymer is more suitable for providing adhesiveness at normal temperature. Specifically, butyl acrylate, 2-ethylhexyl acrylate, 2-ethylhexyl methacrylate, cyclohexyl acrylate, and cyclohexyl methacrylate are more preferred, and 2-ethylhexyl acrylate is most preferred. These alkyl (meth)acrylates (first monomer components) can be used alone or in combination of two or more thereof.

The acrylic adhesive may contain a second monomer copolymerizable with the alkyl (meth)acrylate. Examples of the second monomer include monomers having a functional group that can be a crosslinking point when a crosslinking agent is used. Examples of such a functional group that can be involved with crosslinking reaction include a hydroxy group, a carboxy group, and a vinyl group, with a hydroxy group and a carboxy group being preferred. Specific examples of such a monomer (second monomer component) include hydroxyethyl (meth)acrylate, hydroxypropyl (meth)acrylate, N-hydroxyalkyl(meth)acrylamide, (meth)acrylic acid, itaconic acid, maleic acid, maleic anhydride, mesaconic acid, citraconic acid, and glutaconic acid. From the viewpoint of availability, acrylic acid, methacrylic acid, and hydroxyethyl acrylate (in particular, 2-hydroxyethyl acrylate) are preferred, with acrylic acid being most preferred. These monomers (second monomer components) can be used alone or in combination of two or more thereof.

The acrylic adhesive may contain a third monomer other than the second monomer, if desired. Examples of the third monomer (third monomer component) include vinyl esters such as vinyl acetate and vinyl propionate; vinyl ethers such as methyl vinyl ether and ethyl vinyl ether; vinylamides such as N-vinyl-2-pyrrolidone and N-vinylcaprolactam; alkoxy (meth)acrylates such as methoxyethyl (meth)acrylate, ethoxyethyl (meth)acrylate, and tetrahydrofurfuryl (meth)acrylate; hydroxy group-containing monomers (as the third monomer component, not as a crosslinking point) such as hydroxypropyl (meth)acrylate and α-hydroxymethyl acrylate; (meth)acrylic acid derivatives having an amide group such as (meth)acrylamide, dimethyl(meth)acrylamide, N-butyl(meth)acrylamide, and N-methylol(meth)acrylamide; aminoalkyl (meth)acrylates such as aminoethyl (meth)acrylate, dimethylaminoethyl (meth)acrylate, and t-butylaminoethyl (meth)acrylate; alkoxyalkylene glycol (meth)acrylates such as methoxyethylene glycol (meth)acrylate, methoxydiethylene glycol (meth)acrylate, methoxypolyethylene glycol (meth)acrylate, and methoxypolypropylene glycol (meth)acrylate; (meth)acrylonitrile; monomers having a sulfonic acid such as styrenesulfonic acid, allylsulfonic acid, sulfopropyl (meth)acrylate, (meth)acryloyloxynaphthalenesulfonic acid, and acrylamidemethylsulfonic acid; and vinyl group-containing monomers such as vinylpiperidone, vinylpyrimidine, vinylpiperazine, vinylpyrrole, vinylimidazole, vinyloxazole, and vinylmorpholine. Preferred among these are vinyl esters, and vinylamides. A preferred vinyl ester is vinyl acetate, and a preferred vinylamide is N-vinyl-2-pyrrolidone. These monomers (third monomer components) can be use alone or in combination of two or more thereof.

When the acrylic adhesive is a copolymer of alkyl (meth)acrylate (first monomer component) and a vinyl monomer (second monomer component) having a functional group that can be involved with crosslinking reaction, the alkyl (meth)acrylate and the vinyl monomer having a functional group that can be involved with crosslinking reaction are preferably copolymerized at a weight ratio (alkyl (meth)acrylate:vinyl monomer having a functional group that can be involved with crosslinking reaction) of 99 to 85:1 to 15, more preferably 99 to 90:1 to 10.

When the acrylic adhesive is a copolymer of alkyl (meth)acrylate (first monomer component), a vinyl monomer (second monomer component) having a functional group that can be involved with crosslinking reaction, and a different monomer (third monomer component), the alkyl (meth)acrylate, the vinyl monomer having a functional group that can be involved with crosslinking reaction, and the different monomer are preferably copolymerized at a weight ratio (alkyl (meth)acrylate:vinyl monomer having a functional group that can be involved with crosslinking reaction: different monomer) of 40 to 94:1 to 15:5 to 50, more preferably 50 to 89:1 to 10:10 to 40.

The polymerization reaction is not limited, and may be performed by a known method per se. For example, the above monomers are reacted in the presence of a polymerization initiator (e.g., benzoyl peroxide, azobisisobutyronitrile) in a solvent (e.g., ethyl acetate) at 50° C. to 70° C. for 5 to 48 hours.

Examples of particularly preferred acrylic adhesives in the present invention include 2-ethylhexyl acrylate/acrylic acid/N-vinyl-2-pyrrolidone copolymer, 2-ethylhexyl acrylate/N-(2-hydroxyethyl)acrylamide/N-vinyl-2-pyrrolidone copolymer, 2-ethylhexyl acrylate/2-hydroxyethyl acrylate/vinyl acetate copolymer, and 2-ethylhexyl acrylate/acrylic acid copolymer, with 2-ethylhexyl acrylate/acrylic acid/N-vinyl-2-pyrrolidone copolymer being more preferred.

If desired, these acrylic adhesives may be subjected to physical crosslinking by radiation such as UV irradiation or electron beam irradiation, or may be subjected to chemical crosslinking using various crosslinking agents such as an isocyanate compound (e.g., trifunctional isocyanate), an organic peroxide, an organic metal salt, a metal alcoholate, a metal chelate compound, or a multifunctional compound (e.g., a multifunctional external crosslinking agent, a multifunctional monomer for internal crosslinking such as diacrylate and dimethacrylate).

Examples of the rubber adhesives include those containing a rubber elastomer such as polyisobutylene-polybutene elastomer, styrene-diene-styrene block copolymer, styrene-butadiene elastomer, nitrile elastomer, chloroprene elastomer, vinylpyridine elastomer, polyisobutylene elastomer, butyl elastomer, or isoprene-isobutylene elastomer. In particular, from the viewpoint of the solubility to the antigen and the composition for promoting humoral immunity induction and the adhesiveness to the skin, preferred elastomers include polyisobutylene (PIB) and styrene-diene-styrene block copolymers [e.g., styrene-butadiene-styrene block copolymer (SBS), styrene-isoprene-styrene block copolymer (SIS)]. These elastomers may be used in combination.

In order to obtain suitable adhesion and drug solubility, the rubber adhesive may contain a mixture of rubber elastomers that are the same as or different in the components and different in the average molecular weight. For polyisobutylene, for example, preferred is a mixture of a high-molecular-weight polyisobutylene with an average molecular weight 150,000 to 5,500,000, a middle-molecular-weight polyisobutylene with an average molecular weight of 10,000 to 150,000, and/or a low-molecular-weight polyisobutylene with an average molecular weight of 500 to 4,000. In the mixture, the amount of the high-molecular-weight polyisobutylene is 10 to 80% by weight, preferably 20 to 70% by weight based on the total amount of the polyisobutylenes. The amount of the middle-molecular weight polyisobutylene is 0 to 90% by weight, preferably 10 to 80% by weight based on the total amount of the polyisobutylenes. The amount of the low-molecular-weight polyisobutylene is 0 to 80% by weight, preferably 10 to 60% by weight based on the total amount of the polyisobutylenes.

The average molecular weight herein means the viscosity average molecular weight calculated by Flory's viscosity equation. The average molecular weight is determined by calculating Staudinger index ($J_0$) from the flow time at 20° C. of the capillary 1 of an Ubbelohde viscometer by Schulz-Blaschke equation and calculating the viscosity average molecular weight using the $J_0$ value according to the formula below.

$$J_0 = \eta_{sp}/c(1+0.31\,\eta_{ap}) \quad \text{(Schulz-Blaschke equation)}$$

$$\eta_{ap} = t/t_0 - 1$$

t: Flow time of solution (according to Hagenbach-couette correction formula)
$t_0$: Flow time of solvent (according to Hagenbach-couette correction formula)
c: Concentration of solution (g/cm$^3$)

$$J_0 = 3.06 \times 10^{-2} \overline{Mv}^{0.65}$$

$\overline{Mv}$: Viscosity average molecular weight

In order to provide suitable tackiness, the rubber adhesive may contain a tackifier, such as rosin resin, polyterpene resin, coumarone-indene resin, petroleum resin, terpene-phenol resin, xylene resin, or alicyclic saturated hydrocarbon resin. The rubber adhesive can contain one or two or more of these tackifiers in an amount of 50% by weight or less, preferably 5 to 40% by weight based on the total weight of the rubber adhesive.

Examples of the silicone adhesives include polyorganosiloxane adhesives, polydimethylsiloxane adhesives, and polydimethyldiphenyl-siloxane adhesives. In particular, commercially available silicone adhesives, such as BIO PSA from Dow Corning Corporation, are preferred.

The support for supporting the adhesive layer is not limited. Preferably, the support is one substantially impermeable to the antigen and the composition for promoting humoral immunity induction, that is, one that prevents reduction in the amounts of the antigen, the composition for promoting humoral immunity induction, additives, and the like in the adhesive layer by not allowing them to pass through the support and escape from the back side.

The support may be, for example, a single film containing polyester, polyamide, polyvinylidene chloride, polyethylene, polypropylene, polyvinyl chloride, ethylene-ethyl acrylate copolymer, polytetrafluoroethylene, ionomer resin, or metallic foil or may be a laminated film containing such films. In particular, for good adhesiveness (anchoring properties) between the support and the adhesive layer, the support is preferably a laminated film including a non-porous plastic film and a porous film each containing any of the above materials. In this case, the adhesive layer is preferably formed on the porous film-side. The porous film to be used is one that improves the anchoring properties between the adhesive layer and the porous film. Specific examples thereof include paper, woven fabrics, nonwoven fabrics, knitted fabrics, and mechanically perforated sheets. Preferred among these are paper, woven fabrics, and nonwoven fabrics from the viewpoint of the handleability. The porous film to be used is one that has a thickness within the range of 1 to 200 μm from the viewpoint of improving the anchoring properties and the flexibility and attachment operability of the tape. When the porous film is a woven fabric or a nonwoven fabric, the weight per unit area thereof is preferably 5 to 30 g/m$^2$, more preferably 6 to 15 g/m$^2$.

Examples of the most suitable supports include a laminated film including a polyester film (preferably, polyethylene terephthalate film) with a thickness of 1.5 to 6 μm and a polyester (preferably, polyethylene terephthalate) nonwoven fabric with a weight per unit area of 6 to 15 g/m$^2$.

The tape according to the present invention preferably has a release liner on the adhesive side so as to protect the adhesive side until the time of use. Any release liner can be used as long as it is release-treated and can be peeled with sufficiently light force. For example, the release liner may be a film formed of polyester, polyvinyl chloride, polyvinylidene chloride, or polyethylene terephthalate, paper such as woodfree paper or glassine, or a laminated film including woodfree paper or glassine and a polyolefin, which are release-treated by applying silicone resin, fluororesin, or the like to the side to be in contact with the adhesive layer. The release liner has a thickness of preferably 10 to 200 μm, more preferably 25 to 100 μm. From the viewpoint of barrier properties and the price, the release liner is preferably formed of a polyester (in particular, polyethylene terephthalate) resin.

In this case, from the viewpoint of the handleability, the thickness of the release liner is preferably about 25 to 100 μm.

The pharmaceutical composition of the present invention may further include additive(s), if necessary. The additives can be selected from isotonizing agents, antiseptics, antioxidants, resolvents, solubilizing agents, suspending agents, fillers, pH adjusters, stabilizers, absorption promoters, release-rate controlling agents, colorants, plasticizers, crosslinking agents, adhesives, and the like or combinations of two or more thereof, depending on, for example, the main components of the base, the compatibility with the antigen and composition for promoting humoral immunity induction, or intended administration regimen.

When the pharmaceutical composition of the present invention is in the form of a tape, the tape may contain a skin permeation enhancer as an additive.

As used herein, the term "skin permeation enhancer" means a substance that can improve the efficiency at which a transdermally administered antigen permeates the skin, as compared to the efficiency obtained without the substance. Any skin permeation enhancer can be used as long as it is liquid, that is, fluidic, at room temperature (25° C.) and has an absorption promoting effect. When a mixture of two or more substances is used, the resulting mixture is liquid at room temperature (25° C.). Such an organic liquid component is preferably a hydrophobic liquid component from the viewpoint of the compatibility with the adhesive layer.

Examples of the skin permeation enhancer include higher alcohols such as oleyl alcohol and octyl dodecanol; polyalcohols such as glycerin, ethyleneglycol, and polypropylene glycol; higher fatty acids such as oleic acid and caplyric acid; fatty acid esters such as isopropyl myristate, isopropyl palmitate, and ethyl oleate; polybasic acid esters such as diethyl sebacate and diisopropyl adipate; polyalcohol fatty acid esters such as diglyceryl triisostearate, sorbitan monooleate, propylene glycol dicaprylate, polyethylene glycol monolaurate, and polyoxyethylene sorbitol tetraoleate; polyoxyethylene alkyl ether such as polyoxyethylene lauryl ether; hydrocarbons such as squalane and liquid paraffin; vegetable oils such as olive oil and castor oil; silicone oil; pyrrolidones such as N-methylpyrrolidone and N-dodecylpyrrolidone; and sulfoxides such as decylmethylsulfoxide. These can be used alone or in combination of two or more thereof.

When the rubber or acrylic adhesive is used, a second skin permeation enhancer can be used. Specific examples of the second skin permeation enhancer include, but not limited to, polyvinylpyrrolidone, crospovidone, polypropylene glycol, polyvinyl alcohol, carboxyvinyl polymers, hydroxypropylcellulose, and mixtures thereof. In a preferred embodiment, the second skin permeation enhancer in the present invention contains polyvinylpyrrolidone, crospovidone and/or polypropylene glycol.

In order to enhance skin permeation of the antigen, the skin permeation enhancer is preferably, for example, a higher alcohol, more specifically, a higher alcohol containing 8 to 18 (preferably 8 to 14) carbon atoms; a fatty acid ester, more specifically a fatty acid ester of a fatty acid containing 8 to 18 (preferably 12 to 16) carbon atoms with a monohydric alcohol having 1 to 18 carbon atoms; or a polyalcohol fatty acid ester. The skin permeation enhancer is particularly preferably a fatty acid ester. In particular, isopropyl myristate, isopropyl palmitate, and diethyl sebacate are preferred. The amount of the skin permeation enhancer is preferably 0.1% by weight to 70% by weight, more preferably 1% by weight to 65% by weight, still more preferably 5% by weight to 60% by weight based on the total weight of the adhesive layer. The amount of the skin permeation enhancer of 0.1% by weight or more can provide a high promoting effect for transdermal absorption. The amount of the skin permeation enhancer of 70% by weight or less is advantageous in that high transdermal absorption can be achieved while reduction in the adhesion and cohesion of the entire adhesive layer are suppressed.

<Composition for Promoting Humoral Immunity Induction for Transdermal Administration>

The composition for promoting humoral immunity induction for transdermal administration according to the present invention allows, in administration of various Th2 reaction promoters to the subject, more effective exertion of humoral immunity induced by various antigens administered together with or separately from the TH2 reaction promoters.

As used herein, the term "for transdermal administration" in the composition for promoting humoral immunity induction for transdermal administration may refer to any formulation usually used for transdermal administration. Examples thereof include solutions for external use such as liniments and lotions, sprays for external use such as aerosols, ointments, plasters, creams, gels, and patches such as tapes or poultices. The categories, definition, characteristics, production processes, and the like of these compositions are well known in the art. See the Japanese Pharmacopoeia 16th edition, for example.

For the above formulations, the same materials as those used for preparing the vaccine pharmaceutical composition for transdermal administration can be used.

As used herein, the "pharmacologically acceptable salt" that can be contained in the pharmaceutical composition of the present invention means a salt that does not adversely affect the subject and does not eliminate the pharmacological activity of the components in the pharmaceutical composition. Examples of such a salt include, but not limited to, inorganic acid salts (e.g., hydrochlorides, phosphates), organic acid salts (e.g., acetates, phthalates, TFA salts, mesylates, tartrates), metal salts (alkali metal salts (e.g., sodium salts, potassium salts), alkaline earth metal salts (e.g., calcium salts, magnesium salts), aluminum salts), amine salts (triethylamine salts, benzylamine salt, diethanolamine salts, t-butylamine salts, dicyclohexylamine salts, arginine salts, dimethylammonium salts, ammonium salts).

Advantageous Effects of Invention

The composition for promoting humoral immunity induction and vaccine pharmaceutical composition of the present invention enable effective induction of humoral immunity by promoting Th2 reaction, the central process for antibody production. Furthermore, since the Th2 reaction promoters according to the present invention include many commercial drugs available at pharmacies and widely perceived to be highly safe, the compositions are considered to cause less adverse effects.

The vaccine pharmaceutical composition of the present invention can not only be subcutaneously, intradermally, and intramuscularly injected, but also dermally and mucosally administrated. The composition thus leads to excellent compliance and offers, for example, the following advantages: The composition can be non-invasively administered (e.g., dermally or transmucosally administered), or minimally invasively administered to the skin surface (e.g., to the surface of the skin after a corneum removal treatment such as tape stripping or after a corneum perforation treatment such as a microneedle treatment or electroporation), allowing painless administration and freeing patients from fear for injections. As the composition is easy to administer, patients can administer it by themselves, which reduces the risk of infections of health care workers via needle stick injury, and also reduces the frequency of hospital visits when repetitive administrations are required, contributing to improved quality of life of patients. Moreover, medical wastes requiring specific waste treatment, such as injection needles, are not generated. The composition in a patch form such as a poultice or a tape is advantageous in that it allows secure administration of a predetermined dose and control of the drug releasing rate at any rate, and that it does not stick to unintended sites when administered. The composition in a patch form is advantageous also in that since a patch can easily be removed, patients can immediately stop the administration by themselves by removing the patch from the application site if any adverse effect occurs. The vaccine pharmaceutical composition of the present invention is also advantageous in that it has a significantly improved efficacy compared with an antigen administered alone.

DESCRIPTION OF EMBODIMENTS

Figure 1:
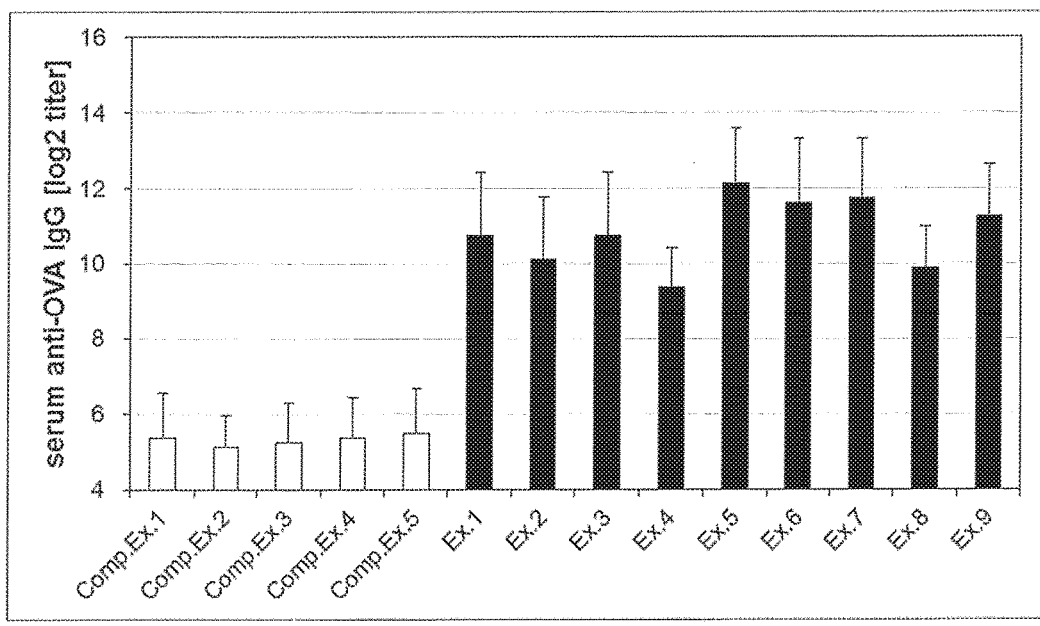
FIG. 1 shows an antigen (OVA)-specific IgG antibody titer in mouse serum after transnasal administration of Th2 reaction promoter (PDE inhibitor and GPCR agonist)-containing pharmaceutical compositions.

The present invention will be specifically described with reference to examples below. The present invention, however, is not limited to these examples.

Examples 1 to 30, Comparative Examples 1 to 8

(Preparation of solution for transmucosal administration)

A solution for transmucosal administration was prepared according to the formulation shown in Tables 2 and 3. Specifically, an antigen and a Th2 reaction promoter were blended in the amounts specified in Tables 2 and 3, and 10 uL of saline was added thereto, followed by mixing to provide a vaccine composition.

Substances used are listed below.
Examples: resveratrol (Wako Pure Chemical Industries, Ltd.), vinpocetine (Yodogawa Seiyaku K.K.), pimobendan (LKT Laboratories), BRL50481 (Tocris Bioscience), dipyridamole (Wako Pure Chemical Industries, Ltd.), methoxyphenamine hydrochloride (MP Biomedicals), fenoldopam mesylate (LKT Laboratories), cisapride (Sigma-Aldrich), desmopressin (Sigma-Aldrich), prazosin hydrochloride (Wako Pure Chemical Industries, Ltd.), pirenzepine hydrochloride (Wako Pure Chemical Industries, Ltd.), oxybutynin hydrochloride (LKT Laboratories), tolterodine tartrate (HELM JAPAN), fluphenazine (Sigma-Aldrich), droperidol (Sigma-Aldrich), sulpiride (Wako Pure Chemical Industries, Ltd.), azelastine hydrochloride (AdooQ BioScience), levocetirizine (Sigma-Aldrich), mequitazine (Wako Pure Chemical Industries, Ltd.), thioperamide (Sigma-Aldrich), sarpogrelate hydrochloride (Sigma-Aldrich), clopidogrel (M/s LEE Pharma), ticlopidine (Wako Pure Chemical Industries, Ltd.), prasugrel (Sigma-Aldrich), apafant (Sigma-Aldrich), naloxone (Wako Pure Chemical Industries, Ltd.), zafirlukast (Sigma-Aldrich), montelukast (LG Life Sciences), pranlukast (Cayman Chemical), candesartan (AdooQ BioScience) Comparative Examples: propranolol hydrochloride (Sigma-Aldrich), butaclamol hydrochloride (Sigma-Aldrich), piboserod hydrochloride (Axon Medchem), tolvaptan (Sigma-Aldrich), metaraminol (Sigma-Aldrich), cevimeline (Sigma-Aldrich), cabergoline (Toronto Research Chemicals)
Model antigen: ovalbumin (OVA)
(Mouse Immunity Test of Solution for Transmucosal Administration)

A mouse immunity test using an animal model for immunity evaluation was performed with the solution prepared as described above. A Mouse (BALB/c mouse, female, 7 weeks old) was provided in advance. After the mouse was anesthetized, the solution was administered to the mouse by transnasal administration (10 uL) or sublingual administration (30 uL). One week after the administration, the mouse was anesthetized again, and the solution was administered again in the same manner.

One week after the second administration, the mouse serum and nasal wash were taken, and the OVA-specific IgG antibody titer in the serum was determined by ELISA.
ELISA The systemic immune response was evaluated by determining the OVA-specific IgG antibody titer in the mouse serum.

<Method for Determining Antigen-Specific IgG Antibody Titer in Mouse Serum (ELISA)>

To each well of a 96-well plate for ELISA was added 100 uL of an OVA-containing solution (100 ug/mL) diluted with carbonate buffer, followed by standing overnight.

The wells were washed three times with preliminarily prepared wash (Tween 20-containing PBS), and to each well was added 200 uL of a blocking solution prepared by diluting a blocking agent (Block Ace, Sumitomo Dainippon Pharma Co., Ltd.) in purified water to 4 g/100 mL. This was followed by standing for 2 hours at room temperature. The wells were then washed three times with wash.

The serum taken from the mouse was centrifuged at 4° C. and 3000 g for 10 minutes, and the supernatant was recovered. The supernatant or nasal wash was diluted in two-fold increments using a solution prepared by diluting a blocking agent in a phosphate buffer (Nacalai Tesque, Inc.) to 0.4 g/100 mL. The diluted solution was added to wells (50 μL for each well), followed by standing for 2 hours at room temperature.

The wells were then washed three times with wash. An HRP-labeled anti-mouse IgG antibody (Goat-anti mouse IgG Fc HRP, BETHYL) was diluted 10000-fold using a solution prepared by diluting a blocking agent in a phosphate buffer (Nacalai Tesque, Inc.) to 0.4 g/100 mL. To each well was added 100 uL of the resulting solution, followed by standing for 1 hour at room temperature.

The wells were then washed three times with wash, and 100 uL of a TMB solution (ELISA POD TMB kit, Nacalai Tesque, Inc.) was added to each well, followed by standing for 30 minutes at dark place.

Figure 2:
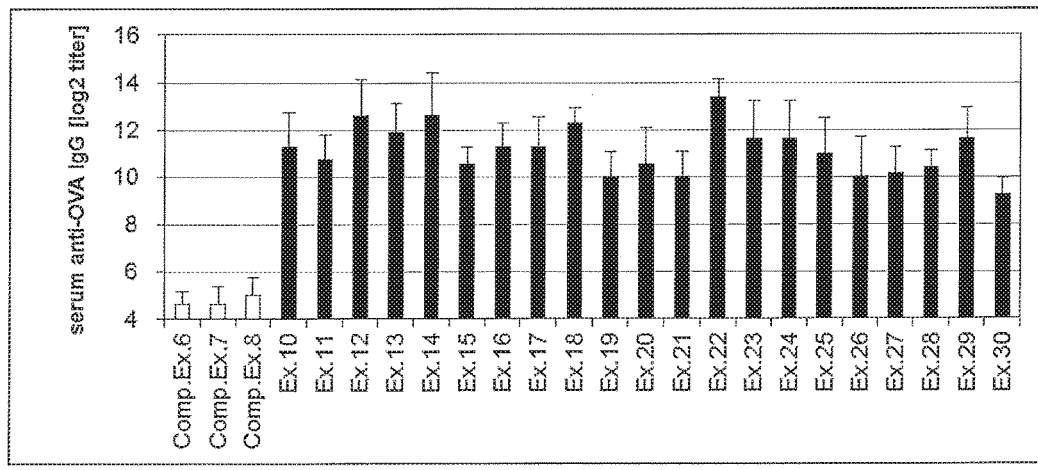
FIG. 2 shows an antigen (OVA)-specific IgG antibody titer in mouse serum after transnasal administration of Th2 reaction promoter (GPCR antagonist)-containing pharmaceutical compositions.

Thereafter, 100 uL of a 1M sulfuric acid solution was added to each well, and the 96-well plate was subjected to measurement of absorbance at 450 nm with a microplate reader (Spectra Max M2$^e$, molecular device). The IgG antibody titer in the mouse serum was determined as Log 2 titer based on the absorbance at the incremental dilution. The results are shown in FIGS. 1 and 2.

TABLE 2

| No. | Administration route | Dosage form | Antigen Name | Amount [ug] | Th2 reaction promoter Name | Amount [ug] | Pharmacological effect | IgG antibody titer [Log2 titer] |
|---|---|---|---|---|---|---|---|---|
| Comp. Ex. 1 | Transnasal | Solution | OVA | 1 | — | — | — | 5.4 |
| Comp. Ex. 2 | Transnasal | Solution | OVA | 1 | Propranolol hydrochloride | 20 | β1-3 antagonization | 5.1 |
| Comp. Ex. 3 | Transnasal | Solution | OVA | 1 | Butaclamol hydrochloride | 20 | D1 antagonization | 5.3 |
| Comp. Ex. 4 | Transnasal | Solution | OVA | 1 | Piboserod hydrochloride | 20 | 5-HT4 antagonization | 5.4 |
| Comp. Ex. 5 | Transnasal | Solution | OVA | 1 | Tolvaptan | 40 | V2 antagonization | 5.5 |
| Ex. 1 | Transnasal | Solution | OVA | 1 | Resveratrol | 40 | PDE inhibition | 10.8 |
| Ex. 2 | Transnasal | Solution | OVA | 1 | Vinpocetine | 20 | PDE inhibition | 10.1 |
| Ex. 3 | Transnasal | Solution | OVA | 1 | Pimobendan | 20 | PDE inhibition | 10.8 |
| Ex. 4 | Transnasal | Solution | OVA | 1 | BRL50481 | 20 | PDE inhibition | 9.4 |
| Ex. 5 | Transnasal | Solution | OVA | 1 | Dipyridamole | 40 | PDE inhibition | 12.1 |
| Ex. 6 | Transnasal | Solution | OVA | 1 | Methoxyphenamine hydrochloride | 20 | β2 activation | 11.6 |
| Ex. 7 | Transnasal | Solution | OVA | 1 | Fenoldopam mesylate | 20 | D1 activation | 11.8 |
| Ex. 8 | Transnasal | Solution | OVA | 1 | Cisapride | 20 | 5-HT4 activation | 9.9 |
| Ex. 9 | Transnasal | Solution | OVA | 1 | Desmopressin | 20 | V2 activation | 11.3 |

TABLE 3

| No. | Administration route | Dosage form | Antigen Name | Amount [ug] | Th2 reaction promoter Name | Amount [ug] | Pharmacological effect | IgG antibody titer [Log2 titer] |
|---|---|---|---|---|---|---|---|---|
| Comp. Ex. 6 | Transnasal | Solution | OVA | 1 | Metaraminol | 20 | α1,2 activation | 4.6 |
| Comp. Ex. 7 | Transnasal | Solution | OVA | 1 | Cevimeline | 20 | M1,3 activation | 4.6 |
| Comp. Ex. 8 | Transnasal | Solution | OVA | 1 | Cabergoline | 20 | D2 activation | 5.0 |
| Ex. 10 | Transnasal | Solution | OVA | 1 | Prazosin hydrochloride | 80 | α1,2 antagonization | 11.3 |
| Ex. 11 | Transnasal | Solution | OVA | 1 | Pirenzepine hydrochloride | 20 | M1 antagonization | 10.8 |
| Ex. 12 | Transnasal | Solution | OVA | 1 | Oxybutynin hydrochloride | 40 | M2 antagonization | 12.6 |
| Ex. 13 | Transnasal | Solution | OVA | 1 | Tolterodine tartrate | 80 | M3 antagonization | 11.9 |
| Ex. 14 | Transnasal | Solution | OVA | 1 | Fluphenazine | 10 | D2 antagonization | 12.6 |
| Ex. 15 | Transnasal | Solution | OVA | 1 | Droperidol | 20 |  | 10.5 |
| Ex. 16 | Transnasal | Solution | OVA | 1 | Sulpiride | 20 |  | 11.3 |
| Ex. 17 | Transnasal | Solution | OVA | 1 | Azelastine hydrochloride | 40 | H1 antagonization | 11.3 |
| Ex. 18 | Transnasal | Solution | OVA | 1 | Levocetirizine | 20 |  | 12.3 |
| Ex. 19 | Transnasal | Solution | OVA | 1 | Mequitazine | 20 |  | 10.0 |
| Ex. 20 | Transnasal | Solution | OVA | 1 | Thioperamide | 20 | H3 antagonization | 10.5 |
| Ex. 21 | Transnasal | Solution | OVA | 1 | Sarpogrelate hydrochloride | 20 | 5-HT2 antagonization | 10.0 |
| Ex. 22 | Transnasal | Solution | OVA | 1 | Clopidogrel | 20 | P2Y12 antagonization | 13.4 |
| Ex. 23 | Transnasal | Solution | OVA | 1 | Ticlopidine | 40 |  | 11.6 |
| Ex. 24 | Transnasal | Solution | OVA | 1 | Prasugrel | 20 |  | 11.6 |
| Ex. 25 | Transnasal | Solution | OVA | 1 | Apafant | 20 | PAF antagonization | 11.0 |
| Ex. 26 | Transnasal | Solution | OVA | 1 | Naloxone | 20 | μ, κ, σ antagonization | 10.0 |
| Ex. 27 | Transnasal | Solution | OVA | 1 | Zafirlukast | 20 | CysLT antagonization | 10.1 |
| Ex. 28 | Transnasal | Solution | OVA | 1 | Montelukast | 20 |  | 10.4 |
| Ex. 29 | Transnasal | Solution | OVA | 1 | Pranlukast | 20 |  | 11.6 |

TABLE 3-continued

| No. | Administration route | Dosage form | Antigen Name | Amount [ug] | Th2 reaction promoter Name | Amount [ug] | Pharmacological effect | IgG antibody titer [Log2 titer] |
|---|---|---|---|---|---|---|---|---|
| Ex. 30 | Transnasal | Solution | OVA | 1 | Candesartan | 20 | AT1 antagonization | 9.3 |

Examples 31 to 55, Comparative Examples 9 to 16

(Preparation of Injection for Subcutaneous Administration)

An injection for subcutaneous administration was prepared according to the formulation shown in Table 4 and 5 below. Specifically, an antigen and a Th2 reaction promoter were blended in the amounts shown in Tables 4 and 5, and 100 uL of saline was added thereto, followed by mixing to provide a vaccine composition.

Substances used are listed below.
Example: resveratrol (Wako Pure Chemical Industries, Ltd.), EHNA (Wako Pure Chemical Industries, Ltd.), cilostazol (LKT Laboratories), pimobendan (LKT Laboratories), BRL50481 (Tocris Bioscience), dipyridamole (Wako Pure Chemical Industries, Ltd.), methoxyphenamine hydrochloride (MP Biomedicals), fenoldopam mesylate (LKT Laboratories), cisapride (Sigma-Aldrich), desmopressin (Sigma-Aldrich), prazosin hydrochloride (Wako Pure Chemical Industries, Ltd.), pirenzepine hydrochloride (Wako Pure Chemical Industries, Ltd.), tolterodine tartrate (HELM JAPAN), scopolamine (Wako Pure Chemical Industries, Ltd.), perphenazine (Sigma-Aldrich), droperidol (Sigma-Aldrich), sulpiride (Wako Pure Chemical Industries, Ltd.), azelastine hydrochloride (AdooQ BioScience), thiopéramide (Sigma-Aldrich), sarpogrelate hydrochloride (Sigma-Aldrich), clopidogrel (M/s LEE Pharma), ticlopidine (Wako Pure Chemical Industries, Ltd.), prasugrel (Sigma-Aldrich), apafant (Sigma-Aldrich), naloxone (Wako Pure Chemical Industries, Ltd.), montelukast (LG Life Sciences), candesartan (AdooQ BioScience)
Comparative Example: propranolol hydrochloride (Sigma-Aldrich), butaclamol hydrochloride (Sigma-Aldrich), piboserod hydrochloride (Axon Medchem), tolvaptan (Sigma-Aldrich), metaraminol (Sigma-Aldrich), cevimeline (Sigma-Aldrich), cabergoline (Toronto Research Chemicals)
Model antigen: ovalbumin (OVA)
(Mouse Immunity Test of Injection for Subcutaneous Administration)

A mouse immunity test using an animal model for immunity evaluation was performed with the solution prepared as described above. A mouse (BALB/c mouse, female, 7 weeks old) was provided in advance, and 200 uL of the injection was subcutaneously injected to the back of the mouse. One week after the administration, the injection was administered again in the same manner.

Figure 3:
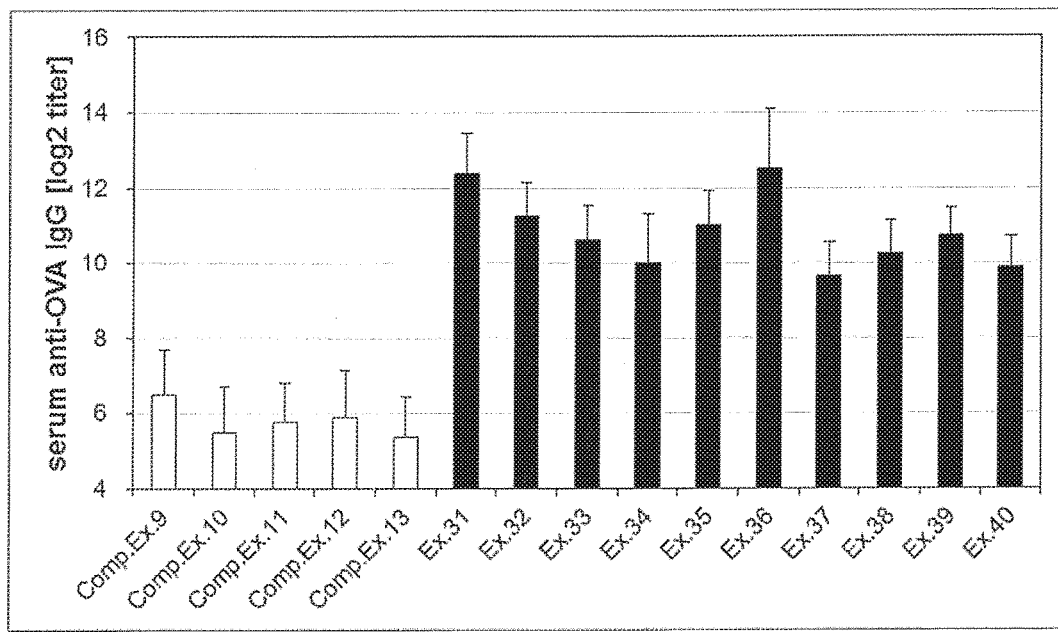
FIG. 3 shows an antigen (OVA)-specific IgG antibody titer in mouse serum after subcutaneous administration of Th2 reaction promoter (PDE inhibitor and GPCR agonist)-containing pharmaceutical compositions.
Figure 4:
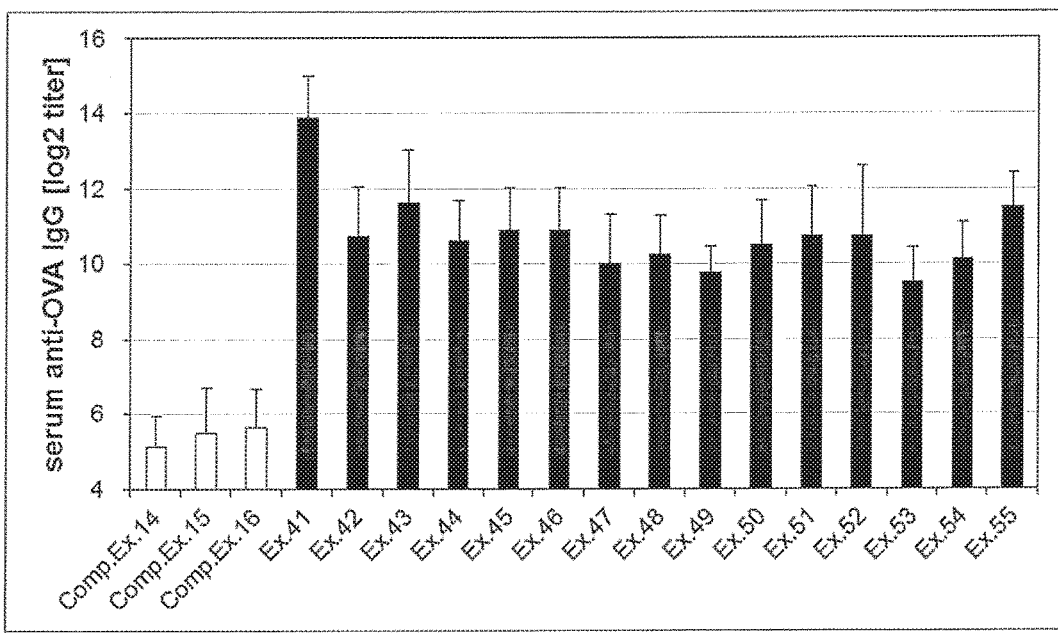
FIG. 4 shows an antigen (OVA)-specific IgG antibody titer in mouse serum after subcutaneous administration of Th2 reaction promoter (GPCR antagonist)-containing pharmaceutical compositions.

One week after the second administration, the mouse serum was taken, and the OVA-specific IgG antibody titer in the serum was determined by ELISA. The results are shown in FIGS. 3 and 4.

TABLE 4

| No. | Administration route | Dosage form | Antigen Name | Amount [ug] | Th2 reaction promoter Name | Amount [ug] | Pharmacological effect | IgG antibody titer [Log2 titer] |
|---|---|---|---|---|---|---|---|---|
| Comp. Ex. 9 | Subcutaneous | Solution | OVA | 0.05 | — | — | — | 6.5 |
| Comp. Ex. 10 | Subcutaneous | Solution | OVA | 0.05 | Propranolol hydrochloride | 200 | β1-3 antagonization | 5.5 |
| Comp. Ex. 11 | Subcutaneous | Solution | OVA | 0.05 | Butaclamol hydrochloride | 200 | D1 antagonization | 5.8 |
| Comp. Ex. 12 | Subcutaneous | Solution | OVA | 0.05 | Piboserod hydrochloride | 200 | 5-HT4 antagonization | 5.9 |
| Comp. Ex. 13 | Subcutaneous | Solution | OVA | 0.05 | Tolvaptan | 200 | V2 antagonization | 5.4 |
| Ex. 31 | Subcutaneous | Solution | OVA | 0.05 | Resveratrol | 200 | PDE inhibition | 12.4 |
| Ex. 32 | Subcutaneous | Solution | OVA | 0.05 | EHNA | 200 | PDE inhibition | 11.3 |
| Ex. 33 | Subcutaneous | Solution | OVA | 0.05 | Cilostazol | 200 | PDE inhibition | 10.6 |
| Ex. 34 | Subcutaneous | Solution | OVA | 0.05 | Pimobendan | 200 | PDE inhibition | 10.0 |
| Ex. 35 | Subcutaneous | Solution | OVA | 0.05 | BRL50481 | 200 | PDE inhibition | 11.0 |
| Ex. 36 | Subcutaneous | Solution | OVA | 0.05 | Dipyridamole | 200 | PDE inhibition | 12.5 |
| Ex. 37 | Subcutaneous | Solution | OVA | 0.05 | Methoxyphenamine hydrochloride | 200 | β2 activation | 9.6 |
| Ex. 38 | Subcutaneous | Solution | OVA | 0.05 | Fenoldopam mesylate | 200 | D1 activation | 10.3 |
| Ex. 39 | Subcutaneous | Solution | OVA | 0.05 | Cisapride | 200 | 5-HT4 activation | 10.8 |
| Ex. 40 | Subcutaneous | Solution | OVA | 0.05 | Desmopressin | 200 | V2 activation | 9.9 |

TABLE 5

| No. | Administration route | Dosage form | Antigen Name | Amount [ug] | Th2 reaction promoter Name | Amount [ug] | Pharmacological effect | IgG antibody titer [Log2 titer] |
|---|---|---|---|---|---|---|---|---|
| Comp. Ex. 14 | Subcutaneous | Solution | OVA | 1 | Metaraminol | 200 | α1,2 activation | 5.1 |
| Comp. Ex. 15 | Subcutaneous | Solution | OVA | 1 | Cevimeline | 200 | M1,3 activation | 5.5 |
| Comp. Ex. 16 | Subcutaneous | Solution | OVA | 1 | Cabergoline | 200 | D2 activation | 5.6 |
| Ex. 41 | Subcutaneous | Solution | OVA | 1 | Prazosin hydrochloride | 200 | α1,2 antagonization | 13.9 |
| Ex. 42 | Subcutaneous | Solution | OVA | 1 | Pirenzepine hydrochloride | 200 | M1 antagonization | 10.8 |
| Ex. 43 | Subcutaneous | Solution | OVA | 1 | Tolterodine tartrate | 200 | M3 antagonization | 11.6 |
| Ex. 44 | Subcutaneous | Solution | OVA | 1 | Scopolamine | 200 | M1-5 antagonization | 10.6 |
| Ex. 45 | Subcutaneous | Solution | OVA | 1 | Perphenazine | 200 | D2 block | 10.9 |
| Ex. 46 | Subcutaneous | Solution | OVA | 1 | Droperidol | 200 | | 10.9 |
| Ex. 47 | Subcutaneous | Solution | OVA | 1 | Sulpiride | 200 | | 10.0 |
| Ex. 48 | Subcutaneous | Solution | OVA | 1 | Azelastine hydrochloride | 200 | H1 antagonization | 10.3 |
| Ex. 49 | Subcutaneous | Solution | OVA | 1 | Clopidogrel | 200 | P2Y12 antagonization | 9.8 |
| Ex. 50 | Subcutaneous | Solution | OVA | 1 | Ticlopidine | 200 | | 10.5 |
| Ex. 51 | Subcutaneous | Solution | OVA | 1 | Prasugrel | 200 | | 10.8 |
| Ex. 52 | Subcutaneous | Solution | OVA | 1 | Apafant | 200 | PAF antagonizstion | 10.8 |
| Ex. 53 | Subcutaneous | Solution | OVA | 1 | Naloxone | 200 | μ, κ, σ antagonization | 9.5 |
| Ex. 54 | Subcutaneous | Solution | OVA | 1 | Montelukast | 200 | CysLT1 antagonization | 10.1 |
| Ex. 55 | Subcutaneous | Solution | OVA | 1 | Candesartan | 200 | AT1 antagonization | 11.5 |

Examples 56 to 69, Comparative Examples 17 to 23

(Preparation of Cream for Transdermal Administration)

A cream for transdermal administration was prepared according to the formulation shown in Table 6 below. Specifically, an antigen and a Th2 reaction promoter were blended in the amounts shown in Table 6. To the mixture was added a base (base cream) to achieve a total amount of 100 parts by weight, followed by mixing to provide a cream. The base cream was prepared by blending and mixing the materials according to the formulation shown in Table 48.

A composite base was prepared by bonding a PET film/PET nonwoven fabric laminate (area: 0.7 cm$^2$) to the center portion of an adhesive tape for attachment such that the PET film side faced the adhesive side of the tape. The cream in an amount of 4 mg was applied to the nonwoven fabric portion of the composite base to provide a sample for an immunity test.

Substances used are listed below.
Example: resveratrol (Wako Pure Chemical Industries, Ltd.), dipyridamole (Wako Pure Chemical Industries, Ltd.), methoxyphenamine hydrochloride (MP Biomedicals), fenoldopam mesylate (LKT Laboratories), cisapride (Sigma-Aldrich), prazosin hydrochloride (Wako Pure Chemical Industries, Ltd.), oxybutynin hydrochloride (LKT Laboratories), tolterodine tartrate (HELM JAPAN), perphenazine (Sigma-Aldrich), azelastine hydrochloride (AdooQ BioScience), clopidogrel (M/s LEE Pharma), apafant (Sigma-Aldrich), montelukast (LG Life Sciences), candesartan (AdooQ BioScience) Comparative Example: propranolol hydrochloride (Sigma-Aldrich), butaclamol hydrochloride (Sigma-Aldrich), piboserod hydrochloride (Axon Medchem), metaraminol (Sigma-Aldrich), cevimeline (Sigma-Aldrich), cabergoline (Toronto Research Chemicals)
Model antigen: ovalbumin (OVA)
(Mouse Immunity Test of Cream for Transdermal Administration)

A mouse immunity test using an animal model for immunity evaluation was performed with the cream prepared as described above. The right back of a mouse (C57BL6 NCr mice, female, 7 weeks old) was shaved in advance. After a rearing period for recovery from the skin damage caused by the shaving, 4 mg of the cream was administered to the skin of the right back of the mouse, and the left back was shaved at the same time. Twenty-four hours later, the formulation was removed. One week after the administration, the cream was administered to the skin of the left back of the mouse, and removed 24 hours later.

Figure 5:
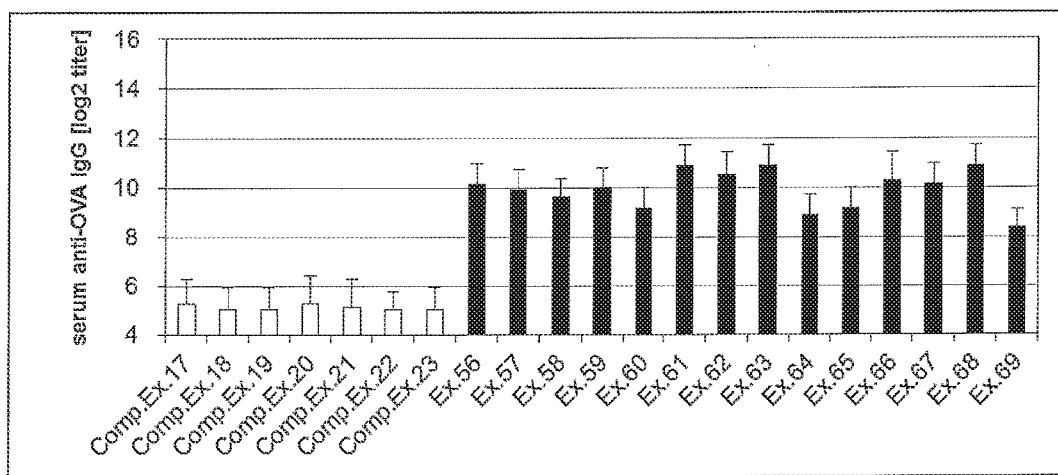
FIG. 5 shows an antigen (OVA)-specific IgG antibody titer in mouse serum after transdermal administration of Th2 reaction promoter (PDE inhibitor, GPCR agonist, and GPCR antagonist)-containing pharmaceutical compositions.

One week after the second administration, the mouse serum was taken and the OVA-specific IgG antibody titer in the serum was determined by ELISA. The results are shown in FIG. 5.

White Vaseline, sorbitan monostearate, isostearic acid, benzyl alcohol, stearyl alcohol, polysorbate 60, and concentrated glycerin were purchased from Wako Pure Chemical Industries, Ltd. Cetanol was purchased from Tokyo Chemical Industry Co., Ltd.

TABLE 6

| No. | Administration route | Dosage form | Antigen Name | Amount [Parts by weight] | Th2 reaction promoter Name | Amount [Parts by weight] | Pharmacological effect | IgG antibody titer [Log2 titer] |
|---|---|---|---|---|---|---|---|---|
| Comp. Ex. 17 | Transdermal | Cream | OVA | 5.0 | — | — | — | 5.3 |
| Comp. Ex. 18 | Transdermal | Cream | OVA | 5.0 | Propranolol hydrochloride | 5.0 | β1-3 antagonization | 5.0 |
| Comp. Ex. 19 | Transdermal | Cream | OVA | 5.0 | Butaclamol hydrochloride | 5.0 | D1 antagonization | 5.0 |
| Comp. Ex. 20 | Transdermal | Cream | OVA | 5.0 | Piboserod hydrochloride | 5.0 | 5-HT4 antagonization | 5.3 |
| Comp. Ex. 21 | Transdermal | Cream | OVA | 5.0 | Metaraminol | 5.0 | α1,2 activation | 5.1 |
| Comp. Ex. 22 | Transdermal | Cream | OVA | 5.0 | Cevimeline | 5.0 | M1,3 activation | 5.0 |
| Comp. Ex. 23 | Transdermal | Cream | OVA | 5.0 | Cabergoline | 5.0 | D2 activation | 5.0 |
| Ex. 56 | Transdermal | Cream | OVA | 5.0 | Resveratrol | 5.0 | PDE inhibition | 10.1 |
| Ex. 57 | Transdermal | Cream | OVA | 5.0 | Dipyridamole | 5.0 | PDE inhibition | 9.9 |
| Ex. 58 | Transdermal | Cream | OVA | 5.0 | Methoxyphenamine hydrochloride | 5.0 | β2 activation | 9.6 |
| Ex. 59 | Transdermal | Cream | OVA | 5.0 | Fenoldopam mesylate | 5.0 | D1 activation | 10.0 |
| Ex. 60 | Transdermal | Cream | OVA | 5.0 | Cisapride | 5.0 | 5-HT4 activation | 9.1 |
| Ex. 61 | Transdermal | Cream | OVA | 5.0 | Prazosin hydrochloride | 5.0 | α1,2 antagonization | 10.9 |
| Ex. 62 | Transdermal | Cream | OVA | 5.0 | Oxybutynin hydrochloride | 5.0 | M2 antagonization | 10.5 |
| Ex. 63 | Transdermal | Cream | OVA | 5.0 | Tolterodine tartrate | 5.0 | M3 antagonization | 10.9 |
| Ex. 64 | Transdermal | Cream | OVA | 5.0 | Perphenazine | 5.0 | D2 block | 8.9 |
| Ex. 65 | Transdermal | Cream | OVA | 5.0 | Azelastine hydrochloride | 5.0 | H1 antagonization | 9.1 |
| Ex. 66 | Transdermal | Cream | OVA | 5.0 | Clopidogrel | 5.0 | P2Y12 antagonization | 10.3 |
| Ex. 67 | Transdermal | Cream | OVA | 5.0 | Apafant | 5.0 | PAF antagonization | 10.1 |
| Ex. 68 | Transdermal | Cream | OVA | 5.0 | Montelukast | 5.0 | CysLT1 antagonization | 10.9 |
| Ex. 69 | Transdermal | Cream | OVA | 5.0 | Candesartan | 5.0 | AT1 antagonization | 8.4 |

Examples 70 to 83, Comparative Example 24

(Preparation of Cream for Transdermal (Minimally Invasive) Administration)

A cream for transdermal administration according to the formulation shown in Table 7 below was prepared in the same manner as the cream for transdermal administration shown in Table 6. The right back of a mouse (C57BL6 NCr mouse, female, 7 weeks old) was shaved, and after the skin was subjected to a corneum removing treatment five times with an OPP tape (EZ Dunplon No. 3301EZ, Nitto Denko Corporation), the cream was administered to the skin (minimally invasive administration), and the left back was shaved at the same time. Twenty-four hours later, the cream for transdermal administration on the right back was removed. One week after the administration, the skin of the left back of the mouse was subjected to a corneum removing treatment in the same manner as above, and the cream for transdermal administration was administered thereto. The cream was removed 24 hours later. One week after the second administration, the mouse serum was taken, and the antigen (OVA)-specific IgG antibody in the serum was determined by ELISA. Also in this immunization using the minimally invasive administration, humoral immunity specific to the administered antigen can be induced.

Substances used are listed below.
Example: resveratrol (Wako Pure Chemical Industries, Ltd.), dipyridamole (Wako Pure Chemical Industries, Ltd.), methoxyphenamine hydrochloride (MP Biomedicals), fenoldopam mesylate (LKT Laboratories), cisapride (Sigma-Aldrich), prazosin hydrochloride (Wako Pure Chemical Industries, Ltd.), oxybutynin hydrochloride (LKT Laboratories), tolterodine tartrate (HELM JAPAN), perphenazine (Sigma-Aldrich), azelastine hydrochloride (AdooQ BioScience), clopidogrel (M/s LEE Pharma), apafant (Sigma-Aldrich), montelukast (LG Life Sciences), candesartan (AdooQ BioScience)

Model antigen: ovalbumin (OVA)

TABLE 7

| No. | Administration route | Dosage form | Antigen Name | Amount [Parts by weight] | Th2 reaction promoter Name | Amount [Parts by weight] | Pharmacological effect |
|---|---|---|---|---|---|---|---|
| Comp. Ex. 24 | Transdermal (minimally invasive) | Cream | OVA | 5.0 | — | — | |
| Ex. 70 | Transdermal (minimally invasive) | Cream | OVA | 5.0 | Resveratrol | 5.0 | PDE inhibition |
| Ex. 71 | Transdermal (minimally invasive) | Cream | OVA | 5.0 | Dipyridamole | 5.0 | PDE inhibition |
| Ex. 72 | Transdermal (minimally invasive) | Cream | OVA | 5.0 | Methoxyphenamine hydrochloride | 5.0 | β2 activation |
| Ex. 73 | Transdermal (minimally invasive) | Cream | OVA | 5.0 | Fenoldopam mesylate | 5.0 | D1 activation |
| Ex. 74 | Transdermal (minimally invasive) | Cream | OVA | 5.0 | Cisapride | 5.0 | 5-HT4 activation |
| Ex. 75 | Transdermal (minimally invasive) | Cream | OVA | 5.0 | Prazosin hydrochloride | 5.0 | α1,2 antagonization |
| Ex. 76 | Transdermal (minimally invasive) | Cream | OVA | 5.0 | Oxybutynin hydrochloride | 5.0 | M2 antagonization |
| Ex. 77 | Transdermal (minimally invasive) | Cream | OVA | 5.0 | Tolterodine tartrate | 5.0 | M3 antagonization |
| Ex. 78 | Transdermal (minimally invasive) | Cream | OVA | 5.0 | Perphenazine | 5.0 | D2 block |
| Ex. 79 | Transdermal (minimally invasive) | Cream | OVA | 5.0 | Azelastine hydrochloride | 5.0 | H1 antagonization |
| Ex. 80 | Transdermal (minimally invasive) | Cream | OVA | 5.0 | Clopidogrel | 5.0 | P2Y12 antagonization |
| Ex. 81 | Transdermal (minimally invasive) | Cream | OVA | 5.0 | Apafant | 5.0 | PAF antagonization |
| Ex. 82 | Transdermal (minimally invasive) | Cream | OVA | 5.0 | Montelukast | 5.0 | CysLT antagonization |
| Ex. 83 | Transdermal (minimally invasive) | Cream | OVA | 5.0 | Candesartan | 5.0 | AT1 antagonization |

Example 84 to 1283, Comparative Examples 25 to 64

(Preparation of Solution for Transmucosal Administration)

A solution for transmucosal administration (transnasal administration or sublingual administration) was prepared according to the formulation shown in Tables 8 to 47 below. Specifically, an antigen and Th2 reaction promoter were blended in the amounts shown in Tables 8 to 47. For transnasal administration, saline was added so that the amount of the resulting mixture was 10 μL. For sublingual administration, saline was added so that the amount of the resulting mixture was 30 μL. This was followed by mixing to provide a solution for transmucosal administration (transnasal administration or sublingual administration).

Model Antigens in Tables 8 to 47

As influenza vaccine antigens, an influenza vaccine antigen-containing solution H1N1 (A/California/07/2009, The Research Foundation for Microbial Diseases of Osaka University), H3N2 (A/Victoria361/2011, The Research Foundation for Microbial Diseases of Osaka University), Influenza B virus (B/Wisconsin/1/2010, The Research Foundation for Microbial Diseases of Osaka University), Influenza B virus (B/Brisbane/60/2008, The Research Foundation for Microbial Diseases of Osaka University) were used. Also used were a pneumococcal capsular polysaccharide-containing solution (Pneumovax NP, MSD), HPV16 recombinant protein-containing solution (HPV16, PROSPEC), a live attenuated rotavirus-containing solution (RotaTeq Oral Solution, MSD), an inactivated poliovirus-containing solution (IMOVAX POLIO for subcutaneous injection, Sanofi), an inactivated hepatitis A virus-containing solution (Aimmugen, The Chemo-Sero-Therapeutic Research Institute), an inactivated Japanese encephalitis virus-containing solution (Encevac for subcutaneous injection, The Chemo-Sero-Therapeutic Research Institute), a live attenuated mumps virus-containing solution (live mumps vaccine, Kitasato Daiichi Sankyo Vaccine Co., Ltd), a live attenuated measles virus-containing solution (live measles vaccine, Kitasato Daiichi Sankyo Vaccine Co., Ltd), a live attenuated rubella virus-containing solution (dried live attenuated rubella vaccine, Kitasato Daiichi Sankyo Vaccine Co., Ltd), a solution containing tetanus toxoid-conjugated *haemophilus influenzae* type b polysaccharide (ActHIB, Sanofi), a recombinant HBs antigen protein-containing solution (Bimmugen, The Chemo-Sero-Therapeutic Research Institute), a live attenuated yellow fever virus-containing solution (yellow fever vaccine, Sanofi), a tetanus toxoid-containing solution (tetanus toxoid, Denka Seiken Co., Ltd.), a live attenuated varicella virus-containing solution (dried live attenuated varicella vaccine, The Research Foundation for Microbial Diseases of Osaka University), a live BCG-containing solution (dried BCG vaccine, Japan BCG Laboratory), and an inactivated rabies virus-containing solution (tissue-cultured inactivated rabies vaccine, The Chemo-Sero-Therapeutic Research Institute).

Substances shown in Tables 8 to 47 are listed below.
Example: resveratrol (Wako Pure Chemical Industries, Ltd.), vinpocetine (Yodogawa Seiyaku K.K.), pimobendan (LKT Laboratories), BRL50481 (Tocris Bioscience), dipyridamole (Wako Pure Chemical Industries, Ltd.), methoxyphenamine hydrochloride (MP Biomedicals), fenoldopam mesylate (LKT Laboratories), cisapride (Sigma-Aldrich), desmopressin (Sigma-Aldrich), prazosin hydrochloride (Wako Pure Chemical Industries, Ltd.), pirenzepine hydrochloride (Wako Pure Chemical Industries, Ltd.), oxybutynin hydrochloride (LKT Laboratories), tolterodine tartrate (HELM JAPAN), fluphenazine (Sigma-Aldrich), droperidol (Sigma-Aldrich), sulpiride (Wako Pure Chemical Industries, Ltd.), azelastine hydrochloride (AdooQ BioScience), levocetirizine (Sigma-Aldrich), mequitazine (Wako Pure Chemical Industries, Ltd.), thioperamide (Sigma-Aldrich), sarpogrelate hydrochloride (Sigma-Aldrich), clopidogrel (M/s LEE Pharma), ticlopidine (Wako Pure Chemical Industries, Ltd.), prasugrel (Sigma-Aldrich), apafant (Sigma-Aldrich), naloxone (Wako Pure Chemical Industries, Ltd.), zafirlukast (Sigma-Aldrich), montelukast (LG Life Sciences), pranlukast (Cayman Chemical), candesartan (AdooQ BioScience)

A mouse immunity test using an animal model for immunity evaluation was performed with the solution prepared as described above. A mouse was provided in advance. After the mouse was anesthetized, the solution was administered to the mouse by transnasal administration (10 uL) or sublingual administration (30 uL). One week after the administration, the mouse was anesthetized again, and the solution was administered again in the same manner. One week after the second administration, the mouse serum and nasal wash were taken, and the OVA-specific IgG antibody titer in the serum was determined by ELISA. In the immunization by transmucosal administration (transnasal administration and sublingual administration), humoral immunity specific to the administered antigen can be induced.

TABLE 8

| | | | Antigen | | Th2 reaction promoter | | | |
|---|---|---|---|---|---|---|---|---|
| | Administration route | Dosage form | Name | Amount [μg] | Name | Amount [μg] | Pharmacological effect | Amount [μL] |
| Comp. Ex. 25 | Transnasal | Solution | A/California/07/2009 [H1N1] | 1.0 | — | — | | 10 |
| Ex. 84 | Transnasal | Solution | A/California/07/2009 [H1N1] | 1.0 | Resveratrol | 40 | PDE inhibition | 10 |
| Ex. 85 | Transnasal | Solution | A/California/07/2009 [H1N1] | 1.0 | Vinpocetine | 20 | PDE inhibition | 10 |
| Ex. 86 | Transnasal | Solution | A/California/07/2009 [H1N1] | 1.0 | Pimobendan | 20 | PDE inhibition | 10 |
| Ex. 87 | Transnasal | Solution | A/California/07/2009 [H1N1] | 1.0 | BRL50481 | 20 | PDE inhibition | 10 |
| Ex. 88 | Transnasal | Solution | A/California/07/2009 [H1N1] | 1.0 | Dipyridamole | 40 | PDE inhibition | 10 |
| Ex. 89 | Transnasal | Solution | A/California/07/2009 [H1N1] | 1.0 | Methoxyphenamine hydrochloride | 20 | β2 activation | 10 |
| Ex. 90 | Transnasal | Solution | A/California/07/2009 [H1N1] | 1.0 | Fenoldopam mesylate | 20 | D1 activation | 10 |
| Ex. 91 | Transnasal | Solution | A/California/07/2009 [H1N1] | 1.0 | Cisapride | 20 | 5-HT4 activation | 10 |
| Ex. 92 | Transnasal | Solution | A/California/07/2009 [H1N1] | 1.0 | Desmopressin | 20 | V2 activation | 10 |
| Ex. 93 | Transnasal | Solution | A/California/07/2009 [H1N1] | 1.0 | Prazosin hydrochloride | 80 | α1,2 antagonization | 10 |
| Ex. 94 | Transnasal | Solution | A/California/07/2009 [H1N1] | 1.0 | Pirenzepine hycrochloride | 20 | M1 antagonization | 10 |
| Ex. 95 | Transnasal | Solution | A/California/07/2009 [H1N1] | 1.0 | Oxybutynin hydrochloride | 40 | M2 antagonization | 10 |
| Ex. 96 | Transnasal | Solution | A/California/07/2009 [H1N1] | 1.0 | Tolterodine tartrate | 80 | M3 antagonization | 10 |
| Ex. 97 | Transnasal | Solution | A/California/07/2009 [H1N1] | 1.0 | Fluphenazine | 10 | D2 antagonization | 10 |
| Ex. 98 | Transnasal | Solution | A/California/07/2009 [H1N1] | 1.0 | Droperidol | 20 | | 10 |
| Ex. 99 | Transnasal | Solution | A/California/07/2009 [H1N1] | 1.0 | Sulpiride | 20 | | 10 |
| Ex. 100 | Transnasal | Solution | A/California/07/2009 [H1N1] | 1.0 | Azelastine hydrochloride | 40 | H1 antagonization | 10 |
| Ex. 101 | Transnasal | Solution | A/California/07/2009 [H1N1] | 1.0 | Levocetirizine | 20 | | 10 |
| Ex. 102 | Transnasal | Solution | A/California/07/2009 [H1N1] | 1.0 | Mequitazine | 20 | | 10 |
| Ex. 103 | Transnasal | Solution | A/California/07/2009 [H1N1] | 1.0 | Thioperamide | 20 | H3 antagonization | 10 |
| Ex. 104 | Transnasal | Solution | A/California/07/2009 [H1N1] | 1.0 | Sarpogrelate hydrochloride | 20 | 5-HT2 antagonization | 10 |
| Ex. 105 | Transnasal | Solution | A/California/07/2009 [H1N1] | 1.0 | Clopidogrel | 20 | P2Y12 antagonization | 10 |
| Ex. 106 | Transnasal | Solution | A/California/07/2009 [H1N1] | 1.0 | Tiolopidine | 40 | | 10 |
| Ex. 107 | Transnasal | Solution | A/California/07/2009 [H1N1] | 1.0 | Prasugrel | 20 | | 10 |
| Ex. 108 | Transnasal | Solution | A/California/07/2009 [H1N1] | 1.0 | Apafant | 20 | PAF antagonization | 10 |
| Ex. 109 | Transnasal | Solution | A/California/07/2009 [H1N1] | 1.0 | Naloxone | 20 | μ, κ, σ antagonization | 10 |
| Ex. 110 | Transnasal | Solution | A/California/07/2009 [H1N1] | 1.0 | Zafirlukast | 20 | CysLT antagonization | 10 |

TABLE 8-continued

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Ex. 111 | Transnasal | Solution | A/California/07/2009 [H1N1] | 1.0 | Montelukast | 20 | | 10 |
| Ex. 112 | Transnasal | Solution | A/California/07/2009 [H1N1] | 1.0 | Pranlukast | 20 | | 10 |
| Ex. 113 | Transnasal | Solution | A/California/07/2009 [H1N1] | 1.0 | Candesartan | 20 | AT1 antagonization | 10 |

TABLE 9

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 26 | Sublingual | Solution | A/California/07/2009 [H1N1] | 1.0 | — | — | | 30 |
| Ex. 114 | Sublingual | Solution | A/California/07/2009 [H1N1] | 1.0 | Resveratrol | 200 | PDE inhibition | 30 |
| Ex. 115 | Sublingual | Solution | A/California/07/2009 [H1N1] | 1.0 | Vinpocetine | 100 | PDE inhibition | 30 |
| Ex. 116 | Sublingual | Solution | A/California/07/2009 [H1N1] | 1.0 | Pimobendan | 100 | PDE inhibition | 30 |
| Ex. 117 | Sublingual | Solution | A/California/07/2009 [H1N1] | 1.0 | BRL50481 | 100 | PDE inhibition | 30 |
| Ex. 118 | Sublingual | Solution | A/California/07/2009 [H1N1] | 1.0 | Dipyridamole | 200 | PDE inhibition | 30 |
| Ex. 119 | Sublingual | Solution | A/California/07/2009 [H1N1] | 1.0 | Methoxyphenamine hydrochloride | 100 | β2 activation | 30 |
| Ex. 120 | Sublingual | Solution | A/California/07/2009 [H1N1] | 1.0 | Fenoldopam mesylate | 100 | D1 activation | 30 |
| Ex. 121 | Sublingual | Solution | A/California/07/2009 [H1N1] | 1.0 | Cisapride | 100 | 5-HT4 activation | 30 |
| Ex. 122 | Sublingual | Solution | A/California/07/2009 [H1N1] | 1.0 | Desmopressin | 100 | V2 activation | 30 |
| Ex. 123 | Sublingual | Solution | A/California/07/2009 [H1N1] | 1.0 | Prazosin hydrochloride | 400 | α1,2 antagonization | 30 |
| Ex. 124 | Sublingual | Solution | A/California/07/2009 [H1N1] | 1.0 | Pirenzepine hycrochloride | 100 | M1 antagonization | 30 |
| Ex. 125 | Sublingual | Solution | A/California/07/2009 [H1N1] | 1.0 | Oxybutynin hydrochloride | 200 | M2 antagonization | 30 |
| Ex. 126 | Sublingual | Solution | A/California/07/2009 [H1N1] | 1.0 | Tolterodine tartrate | 400 | M3 antagonization | 30 |
| Ex. 127 | Sublingual | Solution | A/California/07/2009 [H1N1] | 1.0 | Fluphenazine | 50 | D2 antagonization | 30 |
| Ex. 128 | Sublingual | Solution | A/California/07/2009 [H1N1] | 1.0 | Droperidol | 100 | | 30 |
| Ex. 129 | Sublingual | Solution | A/California/07/2009 [H1N1] | 1.0 | Sulpiride | 100 | | 30 |
| Ex. 130 | Sublingual | Solution | A/California/07/2009 [H1N1] | 1.0 | Azelastine hydrochloride | 200 | H1 antagonization | 30 |
| Ex. 131 | Sublingual | Solution | A/California/07/2009 [H1N1] | 1.0 | Levocetirizine | 100 | | 30 |
| Ex. 132 | Sublingual | Solution | A/California/07/2009 [H1N1] | 1.0 | Mequitazine | 100 | | 30 |
| Ex. 133 | Sublingual | Solution | A/California/07/2009 [H1N1] | 1.0 | Thioperamide | 100 | H3 antagonization | 30 |
| Ex. 134 | Sublingual | Solution | A/California/07/2009 [H1N1] | 1.0 | Sarpogrelate hydrochloride | 100 | 5-HT2 antagonization | 30 |
| Ex. 135 | Sublingual | Solution | A/California/07/2009 [H1N1] | 1.0 | Clopidogrel | 100 | P2Y12 antagonization | 30 |
| Ex. 136 | Sublingual | Solution | A/California/07/2009 [H1N1] | 1.0 | Tiolopidine | 200 | | 30 |
| Ex. 137 | Sublingual | Solution | A/California/07/2009 [H1N1] | 1.0 | Prasugrel | 100 | | 30 |
| Ex. 138 | Sublingual | Solution | A/California/07/2009 [H1N1] | 1.0 | Apafant | 100 | PAF antagonization | 30 |
| Ex. 139 | Sublingual | Solution | A/California/07/2009 [H1N1] | 1.0 | Naloxone | 100 | μ, κ, σ antagonization | 30 |
| Ex. 140 | Sublingual | Solution | A/California/07/2009 [H1N1] | 1.0 | Zafirlukast | 100 | CysLT antagonization | 30 |
| Ex. 141 | Sublingual | Solution | A/California/07/2009 [H1N1] | 1.0 | Montelukast | 100 | | 30 |

TABLE 9-continued

| | Administration route | Dosage form | Antigen Name | Amount [μg] | Th2 reaction promoter Name | Amount [μg] | Pharmacological effect | Amount [μL] |
|---|---|---|---|---|---|---|---|---|
| Ex. 142 | Sublingual | Solution | A/California/07/2009 [H1N1] | 1.0 | Pranlukast | 100 | | 30 |
| Ex. 143 | Sublingual | Solution | A/California/07/2009 [H1N1] | 1.0 | Candesartan | 100 | AT1 antagonization | 30 |

TABLE 10

| | Administration route | Dosage form | Antigen Name | Amount [μg] | Th2 reaction promoter Name | Amount [μg] | Pharmacological effect | Amount [μL] |
|---|---|---|---|---|---|---|---|---|
| Comp. Ex. 27 | Transnasal | Solution | A/Victoria361/2011 [H3N2] | 1.0 | — | — | | 10 |
| Ex. 144 | Transnasal | Solution | A/Victoria361/2011 [H3N2] | 1.0 | Resveratrol | 40 | PDE inhibition | 10 |
| Ex. 145 | Transnasal | Solution | A/Victoria361/2011 [H3N2] | 1.0 | Vinpocetine | 20 | PDE inhibition | 10 |
| Ex. 146 | Transnasal | Solution | A/Victoria361/2011 [H3N2] | 1.0 | Pimobendan | 20 | PDE inhibition | 10 |
| Ex. 147 | Transnasal | Solution | A/Victoria361/2011 [H3N2] | 1.0 | BRL50481 | 20 | PDE inhibition | 10 |
| Ex. 148 | Transnasal | Solution | A/Victoria361/2011 [H3N2] | 1.0 | Dipyridamole | 40 | PDE inhibition | 10 |
| Ex. 149 | Transnasal | Solution | A/Victoria361/2011 [H3N2] | 1.0 | Methoxyphenamine hydrochloride | 20 | β2 activation | 10 |
| Ex. 150 | Transnasal | Solution | A/Victoria361/2011 [H3N2] | 1.0 | Fenoldopam mesylate | 20 | D1 activation | 10 |
| Ex. 151 | Transnasal | Solution | A/Victoria361/2011 [H3N2] | 1.0 | Cisapride | 20 | 5-HT4 activation | 10 |
| Ex. 152 | Transnasal | Solution | A/Victoria361/2011 [H3N2] | 1.0 | Desmopressin | 20 | V2 activation | 10 |
| Ex. 153 | Transnasal | Solution | A/Victoria361/2011 [H3N2] | 1.0 | Prazosin hydrochloride | 80 | α1,2 antagonization | 10 |
| Ex. 154 | Transnasal | Solution | A/Victoria361/2011 [H3N2] | 1.0 | Pirenzepine hycrochloride | 20 | M1 antagonization | 10 |
| Ex. 155 | Transnasal | Solution | A/Victoria361/2011 [H3N2] | 1.0 | Oxybutynin hydrochloride | 40 | M2 antagonization | 10 |
| Ex. 156 | Transnasal | Solution | A/Victoria361/2011 [H3N2] | 1.0 | Tolterodine tartrate | 80 | M3 antagonization | 10 |
| Ex. 157 | Transnasal | Solution | A/Victoria361/2011 [H3N2] | 1.0 | Fluphenazine | 10 | D2 antagonization | 10 |
| Ex. 158 | Transnasal | Solution | A/Victoria361/2011 [H3N2] | 1.0 | Droperidol | 20 | | 10 |
| Ex. 159 | Transnasal | Solution | A/Victoria361/2011 [H3N2] | 1.0 | Sulpiride | 20 | | 10 |
| Ex. 160 | Transnasal | Solution | A/Victoria361/2011 [H3N2] | 1.0 | Azelastine hydrochloride | 40 | H1 antagonization | 10 |
| Ex. 161 | Transnasal | Solution | A/Victoria361/2011 [H3N2] | 1.0 | Levocetirizine | 20 | | 10 |
| Ex. 162 | Transnasal | Solution | A/Victoria361/2011 [H3N2] | 1.0 | Mequitazine | 20 | | 10 |
| Ex. 163 | Transnasal | Solution | A/Victoria361/2011 [H3N2] | 1.0 | Thioperamide | 20 | H3 antagonization | 10 |
| Ex. 164 | Transnasal | Solution | A/Victoria361/2011 [H3N2] | 1.0 | Sarpogrelate hydrochloride | 20 | 5-HT2 antagonization | 10 |
| Ex. 165 | Transnasal | Solution | A/Victoria361/2011 [H3N2] | 1.0 | Clopidogrel | 20 | P2Y12 antagonization | 10 |
| Ex. 166 | Transnasal | Solution | A/Victoria361/2011 [H3N2] | 1.0 | Tiolopidine | 40 | | 10 |
| Ex. 167 | Transnasal | Solution | A/Victoria361/2011 [H3N2] | 1.0 | Prasugrel | 20 | | 10 |
| Ex. 168 | Transnasal | Solution | A/Victoria361/2011 [H3N2] | 1.0 | Apafant | 20 | PAF antagonization | 10 |
| Ex. 169 | Transnasal | Solution | A/Victoria361/2011 [H3N2] | 1.0 | Naloxone | 20 | μ, κ, σ antagonization | 10 |
| Ex. 170 | Transnasal | Solution | A/Victoria361/2011 [H3N2] | 1.0 | Zafirlukast | 20 | CysLT antagonization | 10 |
| Ex. 171 | Transnasal | Solution | A/Victoria361/2011 [H3N2] | 1.0 | Montelukast | 20 | | 10 |
| Ex. 172 | Transnasal | Solution | A/Victoria361/2011 [H3N2] | 1.0 | Pranlukast | 20 | | 10 |

TABLE 10-continued

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Ex. 173 | Transnasal | Solution | A/Victoria361/2011 [H3N2] | 1.0 | Candesartan | 20 | AT1 antagonization | 10 |

TABLE 11

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 28 | Sublingual | Solution | A/Victoria361/2011 [H3N2] | 1.0 | — | — | | 30 |
| Ex. 174 | Sublingual | Solution | A/Victoria361/2011 [H3N2] | 1.0 | Resveratrol | 200 | PDE inhibition | 30 |
| Ex. 175 | Sublingual | Solution | A/Victoria361/2011 [H3N2] | 1.0 | Vinpocetine | 100 | PDE inhibition | 30 |
| Ex. 176 | Sublingual | Solution | A/Victoria361/2011 [H3N2] | 1.0 | Pimobendan | 100 | PDE inhibition | 30 |
| Ex. 177 | Sublingual | Solution | A/Victoria361/2011 [H3N2] | 1.0 | BRL50481 | 100 | PDE inhibition | 30 |
| Ex. 178 | Sublingual | Solution | A/Victoria361/2011 [H3N2] | 1.0 | Dipyridamole | 200 | PDE inhibition | 30 |
| Ex. 179 | Sublingual | Solution | A/Victoria361/2011 [H3N2] | 1.0 | Methoxyphenamine hydrochloride | 100 | β2 activation | 30 |
| Ex. 180 | Sublingual | Solution | A/Victoria361/2011 [H3N2] | 1.0 | Fenoldopam mesylate | 100 | D1 activation | 30 |
| Ex. 181 | Sublingual | Solution | A/Victoria361/2011 [H3N2] | 1.0 | Cisapride | 100 | 5-HT4 activation | 30 |
| Ex. 182 | Sublingual | Solution | A/Victoria361/2011 [H3N2] | 1.0 | Desmopressin | 100 | V2 activation | 30 |
| Ex. 183 | Sublingual | Solution | A/Victoria361/2011 [H3N2] | 1.0 | Prazosin hydrochloride | 400 | α1,2 antagonization | 30 |
| Ex. 184 | Sublingual | Solution | A/Victoria361/2011 [H3N2] | 1.0 | Pirenzepine hycrochloride | 100 | M1 antagonization | 30 |
| Ex. 185 | Sublingual | Solution | A/Victoria361/2011 [H3N2] | 1.0 | Oxybutynin hydrochloride | 200 | M2 antagonization | 30 |
| Ex. 186 | Sublingual | Solution | A/Victoria361/2011 [H3N2] | 1.0 | Tolterodine tartrate | 400 | M3 antagonization | 30 |
| Ex. 187 | Sublingual | Solution | A/Victoria361/2011 [H3N2] | 1.0 | Fluphenazine | 50 | D2 antagonization | 30 |
| Ex. 188 | Sublingual | Solution | A/Victoria361/2011 [H3N2] | 1.0 | Droperidol | 100 | | 30 |
| Ex. 189 | Sublingual | Solution | A/Victoria361/2011 [H3N2] | 1.0 | Sulpiride | 100 | | 30 |
| Ex. 190 | Sublingual | Solution | A/Victoria361/2011 [H3N2] | 1.0 | Azelastine hydrochloride | 200 | H1 antagonization | 30 |
| Ex. 191 | Sublingual | Solution | A/Victoria361/2011 [H3N2] | 1.0 | Levocetirizine | 100 | | 30 |
| Ex. 192 | Sublingual | Solution | A/Victoria361/2011 [H3N2] | 1.0 | Mequitazine | 100 | | 30 |
| Ex. 193 | Sublingual | Solution | A/Victoria361/2011 [H3N2] | 1.0 | Thioperamide | 100 | H3 antagonization | 30 |
| Ex. 194 | Sublingual | Solution | A/Victoria361/2011 [H3N2] | 1.0 | Sarpogrelate hydrochloride | 100 | 5-HT2 antagonization | 30 |
| Ex. 195 | Sublingual | Solution | A/Victoria361/2011 [H3N2] | 1.0 | Clopidogrel | 100 | P2Y12 antagonization | 30 |
| Ex. 196 | Sublingual | Solution | A/Victoria361/2011 [H3N2] | 1.0 | Tiolopidine | 200 | | 30 |
| Ex. 197 | Sublingual | Solution | A/Victoria361/2011 [H3N2] | 1.0 | Prasugrel | 100 | | 30 |
| Ex. 198 | Sublingual | Solution | A/Victoria361/2011 [H3N2] | 1.0 | Apafant | 100 | PAF antagonization | 30 |
| Ex. 199 | Sublingual | Solution | A/Victoria361/2011 [H3N2] | 1.0 | Naloxone | 100 | μ, κ, σ antagonization | 30 |
| Ex. 200 | Sublingual | Solution | A/Victoria361/2011 [H3N2] | 1.0 | Zafirlukast | 100 | CysLT antagonization | 30 |
| Ex. 201 | Sublingual | Solution | A/Victoria361/2011 [H3N2] | 1.0 | Montelukast | 100 | | 30 |

TABLE 11-continued

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Ex. 202 | Sublingual | Solution | A/Victoria361/2011 [H3N2] | 1.0 | Pranlukast | 100 | | 30 |
| Ex. 203 | Sublingual | Solution | A/Victoria361/2011 [H3N2] | 1.0 | Candesartan | 100 | AT1 antagonization | 30 |

TABLE 12

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 29 | Transnasal | Solution | B/Wisconsin/1/2010 | 1.0 | — | — | | 10 |
| Ex. 204 | Transnasal | Solution | B/Wisconsin/1/2010 | 1.0 | Resveratrol | 40 | PDE inhibition | 10 |
| Ex. 205 | Transnasal | Solution | B/Wisconsin/1/2010 | 1.0 | Vinpocetine | 20 | PDE inhibition | 10 |
| Ex. 206 | Transnasal | Solution | B/Wisconsin/1/2010 | 1.0 | Pimobendan | 20 | PDE inhibition | 10 |
| Ex. 207 | Transnasal | Solution | B/Wisconsin/1/2010 | 1.0 | BRL50481 | 20 | PDE inhibition | 10 |
| Ex. 208 | Transnasal | Solution | B/Wisconsin/1/2010 | 1.0 | Dipyridamole | 40 | PDE inhibition | 10 |
| Ex. 209 | Transnasal | Solution | B/Wisconsin/1/2010 | 1.0 | Methoxyphenamine hydrochloride | 20 | β2 activation | 10 |
| Ex. 210 | Transnasal | Solution | B/Wisconsin/1/2010 | 1.0 | Fenoldopam mesylate | 20 | D1 activation | 10 |
| Ex. 211 | Transnasal | Solution | B/Wisconsin/1/2010 | 1.0 | Cisapride | 20 | 5-HT4 activation | 10 |
| Ex. 212 | Transnasal | Solution | B/Wisconsin/1/2010 | 1.0 | Desmopressin | 20 | V2 activation | 10 |
| Ex. 213 | Transnasal | Solution | B/Wisconsin/1/2010 | 1.0 | Prazosin hydrochloride | 80 | α1,2 antagonization | 10 |
| Ex. 214 | Transnasal | Solution | B/Wisconsin/1/2010 | 1.0 | Pirenzepine hycrochloride | 20 | M1 antagonization | 10 |
| Ex. 215 | Transnasal | Solution | B/Wisconsin/1/2010 | 1.0 | Oxybutynin hydrochloride | 40 | M2 antagonization | 10 |
| Ex. 216 | Transnasal | Solution | B/Wisconsin/1/2010 | 1.0 | Tolterodine tartrate | 80 | M3 antagonization | 10 |
| Ex. 217 | Transnasal | Solution | B/Wisconsin/1/2010 | 1.0 | Fluphenazine | 10 | D2 antagonization | 10 |
| Ex. 218 | Transnasal | Solution | B/Wisconsin/1/2010 | 1.0 | Droperidol | 20 | | 10 |
| Ex. 219 | Transnasal | Solution | B/Wisconsin/1/2010 | 1.0 | Sulpiride | 20 | | 10 |
| Ex. 220 | Transnasal | Solution | B/Wisconsin/1/2010 | 1.0 | Azelastine hydrochloride | 40 | H1 antagonization | 10 |
| Ex. 221 | Transnasal | Solution | B/Wisconsin/1/2010 | 1.0 | Levocetirizine | 20 | | 10 |
| Ex. 222 | Transnasal | Solution | B/Wisconsin/1/2010 | 1.0 | Mequitazine | 20 | | 10 |
| Ex. 223 | Transnasal | Solution | B/Wisconsin/1/2010 | 1.0 | Thioperamide | 20 | H3 antagonization | 10 |
| Ex. 224 | Transnasal | Solution | B/Wisconsin/1/2010 | 1.0 | Sarpogrelate hydrochloride | 20 | 5-HT2 antagonization | 10 |
| Ex. 225 | Transnasal | Solution | B/Wisconsin/1/2010 | 1.0 | Clopidogrel | 20 | P2Y12 antagonization | 10 |
| Ex. 226 | Transnasal | Solution | B/Wisconsin/1/2010 | 1.0 | Tiolopidine | 40 | | 10 |
| Ex. 227 | Transnasal | Solution | B/Wisconsin/1/2010 | 1.0 | Prasugrel | 20 | | 10 |
| Ex. 228 | Transnasal | Solution | B/Wisconsin/1/2010 | 1.0 | Apafant | 20 | PAF antagonization | 10 |
| Ex. 229 | Transnasal | Solution | B/Wisconsin/1/2010 | 1.0 | Naloxone | 20 | μ, κ, σ antagonization | 10 |
| Ex. 230 | Transnasal | Solution | B/Wisconsin/1/2010 | 1.0 | Zafirlukast | 20 | CysLT antagonization | 10 |
| Ex. 231 | Transnasal | Solution | B/Wisconsin/1/2010 | 1.0 | Montelukast | 20 | | 10 |
| Ex. 232 | Transnasal | Solution | B/Wisconsin/1/2010 | 1.0 | Pranlukast | 20 | | 10 |
| Ex. 233 | Transnasal | Solution | B/Wisconsin/1/2010 | 1.0 | Candesartan | 20 | AT1 antagonization | 10 |

TABLE 13

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 30 | Sublingual | Solution | B/Wisconsin/1/2010 | 1.0 | — | — | | 30 |
| Ex. 234 | Sublingual | Solution | B/Wisconsin/1/2010 | 1.0 | Resveratrol | 200 | PDE inhibition | 30 |
| Ex. 235 | Sublingual | Solution | B/Wisconsin/1/2010 | 1.0 | Vinpocetine | 100 | PDE inhibition | 30 |
| Ex. 236 | Sublingual | Solution | B/Wisconsin/1/2010 | 1.0 | Pimobendan | 100 | PDE inhibition | 30 |
| Ex. 237 | Sublingual | Solution | B/Wisconsin/1/2010 | 1.0 | BRL50481 | 100 | PDE inhibition | 30 |
| Ex. 238 | Sublingual | Solution | B/Wisconsin/1/2010 | 1.0 | Dipyridamole | 200 | PDE inhibition | 30 |
| Ex. 239 | Sublingual | Solution | B/Wisconsin/1/2010 | 1.0 | Methoxyphenamine hydrochloride | 100 | β2 activation | 30 |
| Ex. 240 | Sublingual | Solution | B/Wisconsin/1/2010 | 1.0 | Fenoldopam mesylate | 100 | D1 activation | 30 |
| Ex. 241 | Sublingual | Solution | B/Wisconsin/1/2010 | 1.0 | Cisapride | 100 | 5-HT4 activation | 30 |
| Ex. 242 | Sublingual | Solution | B/Wisconsin/1/2010 | 1.0 | Desmopressin | 100 | V2 activation | 30 |
| Ex. 243 | Sublingual | Solution | B/Wisconsin/1/2010 | 1.0 | Prazosin hydrochloride | 400 | α1,2 antagonization | 30 |
| Ex. 244 | Sublingual | Solution | B/Wisconsin/1/2010 | 1.0 | Pirenzepine hycrochloride | 100 | M1 antagonization | 30 |
| Ex. 245 | Sublingual | Solution | B/Wisconsin/1/2010 | 1.0 | Oxybutynin hydrochloride | 200 | M2 antagonization | 30 |
| Ex. 246 | Sublingual | Solution | B/Wisconsin/1/2010 | 1.0 | Tolterodine tartrate | 400 | M3 antagonization | 30 |
| Ex. 247 | Sublingual | Solution | B/Wisconsin/1/2010 | 1.0 | Fluphenazine | 50 | D2 antagonization | 30 |
| Ex. 248 | Sublingual | Solution | B/Wisconsin/1/2010 | 1.0 | Droperidol | 100 | | 30 |
| Ex. 249 | Sublingual | Solution | B/Wisconsin/1/2010 | 1.0 | Sulpiride | 100 | | 30 |
| Ex. 250 | Sublingual | Solution | B/Wisconsin/1/2010 | 1.0 | Azelastine hydrochloride | 200 | H1 antagonization | 30 |
| Ex. 251 | Sublingual | Solution | B/Wisconsin/1/2010 | 1.0 | Levocetirizine | 100 | | 30 |
| Ex. 252 | Sublingual | Solution | B/Wisconsin/1/2010 | 1.0 | Mequitazine | 100 | | 30 |
| Ex. 253 | Sublingual | Solution | B/Wisconsin/1/2010 | 1.0 | Thioperamide | 100 | H3 antagonization | 30 |
| Ex. 254 | Sublingual | Solution | B/Wisconsin/1/2010 | 1.0 | Sarpogrelate hydrochloride | 100 | 5-HT2 antagonization | 30 |
| Ex. 255 | Sublingual | Solution | B/Wisconsin/1/2010 | 1.0 | Clopidogrel | 100 | P2Y12 antagonization | 30 |
| Ex. 256 | Sublingual | Solution | B/Wisconsin/1/2010 | 1.0 | Tiolopidine | 200 | | 30 |
| Ex. 257 | Sublingual | Solution | B/Wisconsin/1/2010 | 1.0 | Prasugrel | 100 | | 30 |
| Ex. 258 | Sublingual | Solution | B/Wisconsin/1/2010 | 1.0 | Apafant | 100 | PAF antagonization | 30 |
| Ex. 259 | Sublingual | Solution | B/Wisconsin/1/2010 | 1.0 | Naloxone | 100 | μ, κ, σ antagonization | 30 |
| Ex. 260 | Sublingual | Solution | B/Wisconsin/1/2010 | 1.0 | Zafirlukast | 100 | CysLT antagonization | 30 |
| Ex. 261 | Sublingual | Solution | B/Wisconsin/1/2010 | 1.0 | Montelukast | 100 | | 30 |
| Ex. 262 | Sublingual | Solution | B/Wisconsin/1/2010 | 1.0 | Pranlukast | 100 | | 30 |
| Ex. 263 | Sublingual | Solution | B/Wisconsin/1/2010 | 1.0 | Candesartan | 100 | AT1 antagonization | 30 |

TABLE 14

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 31 | Transnasal | Solution | B/Brisbane/60/2008 | 1.0 | — | — | | 10 |
| Ex. 264 | Transnasal | Solution | B/Brisbane/60/2008 | 1.0 | Resveratrol | 40 | PDE inhibition | 10 |
| Ex. 265 | Transnasal | Solution | B/Brisbane/60/2008 | 1.0 | Vinpocetine | 20 | PDE inhibition | 10 |
| Ex. 266 | Transnasal | Solution | B/Brisbane/60/2008 | 1.0 | Pimobendan | 20 | PDE inhibition | 10 |
| Ex. 267 | Transnasal | Solution | B/Brisbane/60/2008 | 1.0 | BRL50481 | 20 | PDE inhibition | 10 |

TABLE 14-continued

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Ex. 268 | Transnasal | Solution | B/Brisbane/60/2008 | 1.0 | Dipyridamole | 40 | PDE inhibition | 10 |
| Ex. 269 | Transnasal | Solution | B/Brisbane/60/2008 | 1.0 | Methoxyphenamine hydrochloride | 20 | β2 activation | 10 |
| Ex. 270 | Transnasal | Solution | B/Brisbane/60/2008 | 1.0 | Fenoldopam mesylate | 20 | D1 activation | 10 |
| Ex. 271 | Transnasal | Solution | B/Brisbane/60/2008 | 1.0 | Cisapride | 20 | 5-HT4 activation | 10 |
| Ex. 272 | Transnasal | Solution | B/Brisbane/60/2008 | 1.0 | Desmopressin | 20 | V2 activation | 10 |
| Ex. 273 | Transnasal | Solution | B/Brisbane/60/2008 | 1.0 | Prazosin hydrochloride | 80 | α1,2 antagonization | 10 |
| Ex. 274 | Transnasal | Solution | B/Brisbane/60/2008 | 1.0 | Pirenzepine hycrochloride | 20 | M1 antagonization | 10 |
| Ex. 275 | Transnasal | Solution | B/Brisbane/60/2008 | 1.0 | Oxybutynin hydrochloride | 40 | M2 antagonization | 10 |
| Ex. 276 | Transnasal | Solution | B/Brisbane/60/2008 | 1.0 | Tolterodine tartrate | 80 | M3 antagonization | 10 |
| Ex. 277 | Transnasal | Solution | B/Brisbane/60/2008 | 1.0 | Fluphenazine | 10 | D2 antagonization | 10 |
| Ex. 278 | Transnasal | Solution | B/Brisbane/60/2008 | 1.0 | Droperidol | 20 | | 10 |
| Ex. 279 | Transnasal | Solution | B/Brisbane/60/2008 | 1.0 | Sulpiride | 20 | | 10 |
| Ex. 280 | Transnasal | Solution | B/Brisbane/60/2008 | 1.0 | Azelastine hydrochloride | 40 | H1 antagonization | 10 |
| Ex. 281 | Transnasal | Solution | B/Brisbane/60/2008 | 1.0 | Levocetirizine | 20 | | 10 |
| Ex. 282 | Transnasal | Solution | B/Brisbane/60/2008 | 1.0 | Mequitazine | 20 | | 10 |
| Ex. 283 | Transnasal | Solution | B/Brisbane/60/2008 | 1.0 | Thioperamide | 20 | H3 antagonization | 10 |
| Ex. 284 | Transnasal | Solution | B/Brisbane/60/2008 | 1.0 | Sarpogrelate hydrochloride | 20 | 5-HT2 antagonization | 10 |
| Ex. 285 | Transnasal | Solution | B/Brisbane/60/2008 | 1.0 | Clopidogrel | 20 | P2Y12 antagonization | 10 |
| Ex. 286 | Transnasal | Solution | B/Brisbane/60/2008 | 1.0 | Tiolopidine | 40 | | 10 |
| Ex. 287 | Transnasal | Solution | B/Brisbane/60/2008 | 1.0 | Prasugrel | 20 | | 10 |
| Ex. 288 | Transnasal | Solution | B/Brisbane/60/2008 | 1.0 | Apafant | 20 | PAF antagonization | 10 |
| Ex. 289 | Transnasal | Solution | B/Brisbane/60/2008 | 1.0 | Naloxone | 20 | μ, κ, σ antagonization | 10 |
| Ex. 290 | Transnasal | Solution | B/Brisbane/60/2008 | 1.0 | Zafirlukast | 20 | CysLT antagonization | 10 |
| Ex. 291 | Transnasal | Solution | B/Brisbane/60/2008 | 1.0 | Montelukast | 20 | | 10 |
| Ex. 292 | Transnasal | Solution | B/Brisbane/60/2008 | 1.0 | Pranlukast | 20 | | 10 |
| Ex. 293 | Transnasal | Solution | B/Brisbane/60/2008 | 1.0 | Candesartan | 20 | AT1 antagonization | 10 |

TABLE 15

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 32 | Sublingual | Solution | B/Brisbane/60/2008 | 1.0 | — | — | | 30 |
| Ex. 294 | Sublingual | Solution | B/Brisbane/60/2008 | 1.0 | Resveratrol | 200 | PDE inhibition | 30 |
| Ex. 295 | Sublingual | Solution | B/Brisbane/60/2008 | 1.0 | Vinpocetine | 100 | PDE inhibition | 30 |
| Ex. 296 | Sublingual | Solution | B/Brisbane/60/2008 | 1.0 | Pimobendan | 100 | PDE inhibition | 30 |
| Ex. 297 | Sublingual | Solution | B/Brisbane/60/2008 | 1.0 | BRL50481 | 100 | PDE inhibition | 30 |
| Ex. 298 | Sublingual | Solution | B/Brisbane/60/2008 | 1.0 | Dipyridamole | 200 | PDE inhibition | 30 |
| Ex. 299 | Sublingual | Solution | B/Brisbane/60/2008 | 1.0 | Methoxyphenamine hydrochloride | 100 | β2 activation | 30 |
| Ex. 300 | Sublingual | Solution | B/Brisbane/60/2008 | 1.0 | Fenoldopam mesylate | 100 | D1 activation | 30 |
| Ex. 301 | Sublingual | Solution | B/Brisbane/60/2008 | 1.0 | Cisapride | 100 | 5-HT4 activation | 30 |
| Ex. 302 | Sublingual | Solution | B/Brisbane/60/2008 | 1.0 | Desmopressin | 100 | V2 activation | 30 |

TABLE 15-continued

| | Administration route | Dosage form | Antigen Name | Amount [μg] | Th2 reaction promoter Name | Amount [μg] | Pharmacological effect | Amount [μL] |
|---|---|---|---|---|---|---|---|---|
| Ex. 303 | Sublingual | Solution | B/Brisbane/60/2008 | 1.0 | Prazosin hydrochloride | 400 | α1,2 antagonization | 30 |
| Ex. 304 | Sublingual | Solution | B/Brisbane/60/2008 | 1.0 | Pirenzepine hycrochloride | 100 | M1 antagonization | 30 |
| Ex. 305 | Sublingual | Solution | B/Brisbane/60/2008 | 1.0 | Oxybutynin hydrochloride | 200 | M2 antagonization | 30 |
| Ex. 306 | Sublingual | Solution | B/Brisbane/60/2008 | 1.0 | Tolterodine tartrate | 400 | M3 antagonization | 30 |
| Ex. 307 | Sublingual | Solution | B/Brisbane/60/2008 | 1.0 | Fluphenazine | 50 | D2 antagonization | 30 |
| Ex. 308 | Sublingual | Solution | B/Brisbane/60/2008 | 1.0 | Droperidol | 100 | | 30 |
| Ex. 309 | Sublingual | Solution | B/Brisbane/60/2008 | 1.0 | Sulpiride | 100 | | 30 |
| Ex. 310 | Sublingual | Solution | B/Brisbane/60/2008 | 1.0 | Azelastine hydrochloride | 200 | H1 antagonization | 30 |
| Ex. 311 | Sublingual | Solution | B/Brisbane/60/2008 | 1.0 | Levocetirizine | 100 | | 30 |
| Ex. 312 | Sublingual | Solution | B/Brisbane/60/2008 | 1.0 | Mequitazine | 100 | | 30 |
| Ex. 313 | Sublingual | Solution | B/Brisbane/60/2008 | 1.0 | Thioperamide | 100 | H3 antagonization | 30 |
| Ex. 314 | Sublingual | Solution | B/Brisbane/60/2008 | 1.0 | Sarpogrelate hydrochloride | 100 | 5-HT2 antagonization | 30 |
| Ex. 315 | Sublingual | Solution | B/Brisbane/60/2008 | 1.0 | Clopidogrel | 100 | P2Y12 antagonization | 30 |
| Ex. 316 | Sublingual | Solution | B/Brisbane/60/2008 | 1.0 | Tiolopidine | 200 | | 30 |
| Ex. 317 | Sublingual | Solution | B/Brisbane/60/2008 | 1.0 | Prasugrel | 100 | | 30 |
| Ex. 318 | Sublingual | Solution | B/Brisbane/60/2008 | 1.0 | Apafant | 100 | PAF antagonization | 30 |
| Ex. 319 | Sublingual | Solution | B/Brisbane/60/2008 | 1.0 | Naloxone | 100 | μ, κ, σ antagonization | 30 |
| Ex. 320 | Sublingual | Solution | B/Brisbane/60/2008 | 1.0 | Zafirlukast | 100 | CysLT antagonization | 30 |
| Ex. 321 | Sublingual | Solution | B/Brisbane/60/2008 | 1.0 | Montelukast | 100 | | 30 |
| Ex. 322 | Sublingual | Solution | B/Brisbane/60/2008 | 1.0 | Pranlukast | 100 | | 30 |
| Ex. 323 | Sublingual | Solution | B/Brisbane/60/2008 | 1.0 | Candesartan | 100 | AT1 antagonization | 30 |

TABLE 16

| | Administration route | Dosage form | Antigen Name | Amount [μg] | Th2 reaction promoter Name | Amount [μg] | Pharmacological effect | Amount [μL] |
|---|---|---|---|---|---|---|---|---|
| Comp. Ex. 33 | Transnasal | Solution | Pneumococcal capsular polysaccharide Pneumovax NP | 20 | — | — | | 10 |
| Ex. 324 | Transnasal | Solution | Pneumococcal capsular polysaccharide Pneumovax NP | 20 | Resveratrol | 40 | PDE inhibition | 10 |
| Ex. 325 | Transnasal | Solution | Pneumococcal capsular polysaccharide Pneumovax NP | 20 | Vinpocetine | 20 | PDE inhibition | 10 |
| Ex. 326 | Transnasal | Solution | Pneumococcal capsular polysaccharide Pneumovax NP | 20 | Pimobendan | 20 | PDE inhibition | 10 |
| Ex. 327 | Transnasal | Solution | Pneumococcal capsular polysaccharide Pneumovax NP | 20 | BRL50481 | 20 | PDE inhibition | 10 |
| Ex. 328 | Transnasal | Solution | Pneumococcal capsular polysaccharide Pneumovax NP | 20 | Dipyridamole | 40 | PDE inhibition | 10 |
| Ex. 329 | Transnasal | Solution | Pneumococcal capsular polysaccharide Pneumovax NP | 20 | Methoxyphenamine hydrochloride | 20 | β2 activation | 10 |
| Ex. 330 | Transnasal | Solution | Pneumococcal capsular polysaccharide Pneumovax NP | 20 | Fenoldopam mesylate | 20 | D1 activation | 10 |
| Ex. 331 | Transnasal | Solution | Pneumococcal capsular polysaccharide Pneumovax NP | 20 | Cisapride | 20 | 5-HT4 activation | 10 |
| Ex. 332 | Transnasal | Solution | Pneumococcal capsular polysaccharide Pneumovax NP | 20 | Desmopressin | 20 | V2 activation | 10 |
| Ex. 333 | Transnasal | Solution | Pneumococcal capsular polysaccharide Pneumovax NP | 20 | Prazosin hydrochloride | 80 | α1,2 antagonization | 10 |
| Ex. 334 | Transnasal | Solution | Pneumococcal capsular polysaccharide Pneumovax NP | 20 | Pirenzepine hycrochloride | 20 | M1 antagonization | 10 |
| Ex. 335 | Transnasal | Solution | Pneumococcal capsular polysaccharide Pneumovax NP | 20 | Oxybutynin hydrochloride | 40 | M2 antagonization | 10 |
| Ex. 336 | Transnasal | Solution | Pneumococcal capsular polysaccharide Pneumovax NP | 20 | Tolterodine tartrate | 80 | M3 antagonization | 10 |
| Ex. 337 | Transnasal | Solution | Pneumococcal capsular polysaccharide Pneumovax NP | 20 | Fluphenazine | 10 | D2 antagonization | 10 |

TABLE 16-continued

|  | Administration route | Dosage form | Antigen Name | Amount [μg] | Th2 reaction promoter Name | Amount [μg] | Pharmacological effect | Amount [μL] |
|---|---|---|---|---|---|---|---|---|
| Ex. 338 | Transnasal | Solution | Pneumococcal capsular polysaccharide Pneumovax NP | 20 | Droperidol | 20 |  | 10 |
| Ex. 339 | Transnasal | Solution | Pneumococcal capsular polysaccharide Pneumovax NP | 20 | Sulpiride | 20 |  | 10 |
| Ex. 340 | Transnasal | Solution | Pneumococcal capsular polysaccharide Pneumovax NP | 20 | Azelastine hydrochloride | 40 | H1 antagonization | 10 |
| Ex. 341 | Transnasal | Solution | Pneumococcal capsular polysaccharide Pneumovax NP | 20 | Levocetirizine | 20 |  | 10 |
| Ex. 342 | Transnasal | Solution | Pneumococcal capsular polysaccharide Pneumovax NP | 20 | Mequitazine | 20 |  | 10 |
| Ex. 343 | Transnasal | Solution | Pneumococcal capsular polysaccharide Pneumovax NP | 20 | Thioperamide | 20 | H3 antagonization | 10 |
| Ex. 344 | Transnasal | Solution | Pneumococcal capsular polysaccharide Pneumovax NP | 20 | Sarpogrelate hydrochloride | 20 | 5-HT2 antagonization | 10 |
| Ex. 345 | Transnasal | Solution | Pneumococcal capsular polysaccharide Pneumovax NP | 20 | Clopidogrel | 20 | P2Y12 antagonization | 10 |
| Ex. 346 | Transnasal | Solution | Pneumococcal capsular polysaccharide Pneumovax NP | 20 | Tiolopidine | 40 |  | 10 |
| Ex. 347 | Transnasal | Solution | Pneumococcal capsular polysaccharide Pneumovax NP | 20 | Prasugrel | 20 |  | 10 |
| Ex. 348 | Transnasal | Solution | Pneumococcal capsular polysaccharide Pneumovax NP | 20 | Apafant | 20 | PAF antagonization | 10 |
| Ex. 349 | Transnasal | Solution | Pneumococcal capsular polysaccharide Pneumovax NP | 20 | Naloxone | 20 | μ, κ, σ antagonization | 10 |
| Ex. 350 | Transnasal | Solution | Pneumococcal capsular polysaccharide Pneumovax NP | 20 | Zafirlukast | 20 | CysLT antagonization | 10 |
| Ex. 351 | Transnasal | Solution | Pneumococcal capsular polysaccharide Pneumovax NP | 20 | Montelukast | 20 |  | 10 |
| Ex. 352 | Transnasal | Solution | Pneumococcal capsular polysaccharide Pneumovax NP | 20 | Pranlukast | 20 |  | 10 |
| Ex. 353 | Transnasal | Solution | Pneumococcal capsular polysaccharide Pneumovax NP | 20 | Candesartan | 20 | AT1 antagonization | 10 |

TABLE 17

|  | Administration route | Dosage form | Antigen Name | Amount [μg] | Th2 reaction promoter Name | Amount [μg] | Pharmacological effect | Amount [μL] |
|---|---|---|---|---|---|---|---|---|
| Comp. Ex. 34 | Sublingual | Solution | Pneumococcal capsular polysaccharide Pneumovax NP | 20 | — | — |  | 30 |
| Ex. 354 | Sublingual | Solution | Pneumococcal capsular polysaccharide Pneumovax NP | 20 | Resveratrol | 200 | PDE inhibition | 30 |
| Ex. 355 | Sublingual | Solution | Pneumococcal capsular polysaccharide Pneumovax NP | 20 | Vinpocetine | 100 | PDE inhibition | 30 |
| Ex. 356 | Sublingual | Solution | Pneumococcal capsular polysaccharide Pneumovax NP | 20 | Pimobendan | 100 | PDE inhibition | 30 |
| Ex. 357 | Sublingual | Solution | Pneumococcal capsular polysaccharide Pneumovax NP | 20 | BRL50481 | 100 | PDE inhibition | 30 |
| Ex. 358 | Sublingual | Solution | Pneumococcal capsular polysaccharide Pneumovax NP | 20 | Dipyridamole | 200 | PDE inhibition | 30 |
| Ex. 359 | Sublingual | Solution | Pneumococcal capsular polysaccharide Pneumovax NP | 20 | Methoxyphenamine hydrochloride | 100 | β2 activation | 30 |
| Ex. 360 | Sublingual | Solution | Pneumococcal capsular polysaccharide Pneumovax NP | 20 | Fenoldopam mesylate | 100 | D1 activation | 30 |
| Ex. 361 | Sublingual | Solution | Pneumococcal capsular polysaccharide Pneumovax NP | 20 | Cisapride | 100 | 5-HT4 activation | 30 |
| Ex. 362 | Sublingual | Solution | Pneumococcal capsular polysaccharide Pneumovax NP | 20 | Desmopressin | 100 | V2 activation | 30 |
| Ex. 363 | Sublingual | Solution | Pneumococcal capsular polysaccharide Pneumovax NP | 20 | Prazosin hydrochloride | 400 | α1,2 antagonization | 30 |
| Ex. 364 | Sublingual | Solution | Pneumococcal capsular polysaccharide Pneumovax NP | 20 | Pirenzepine hycrochloride | 100 | M1 antagonization | 30 |
| Ex. 365 | Sublingual | Solution | Pneumococcal capsular polysaccharide Pneumovax NP | 20 | Oxybutynin hydrochloride | 200 | M2 antagonization | 30 |
| Ex. 366 | Sublingual | Solution | Pneumococcal capsular polysaccharide Pneumovax NP | 20 | Tolterodine tartrate | 400 | M3 antagonization | 30 |
| Ex. 367 | Sublingual | Solution | Pneumococcal capsular polysaccharide Pneumovax NP | 20 | Fluphenazine | 50 | D2 antagonization | 30 |
| Ex. 368 | Sublingual | Solution | Pneumococcal capsular polysaccharide Pneumovax NP | 20 | Droperidol | 100 |  | 30 |

TABLE 17-continued

| | Administration route | Dosage form | Antigen Name | Amount [µg] | Th2 reaction promoter Name | Amount [µg] | Pharmacological effect | Amount [µL] |
|---|---|---|---|---|---|---|---|---|
| Ex. 369 | Sublingual | Solution | Pneumococcal capsular polysaccharide Pneumovax NP | 20 | Sulpiride | 100 | | 30 |
| Ex. 370 | Sublingual | Solution | Pneumococcal capsular polysaccharide Pneumovax NP | 20 | Azelastine hydrochloride | 200 | H1 antagonization | 30 |
| Ex. 371 | Sublingual | Solution | Pneumococcal capsular polysaccharide Pneumovax NP | 20 | Levocetirizine | 100 | | 30 |
| Ex. 372 | Sublingual | Solution | Pneumococcal capsular polysaccharide Pneumovax NP | 20 | Mequitazine | 100 | | 30 |
| Ex. 373 | Sublingual | Solution | Pneumococcal capsular polysaccharide Pneumovax NP | 20 | Thioperamide | 100 | H3 antagonization | 30 |
| Ex. 374 | Sublingual | Solution | Pneumococcal capsular polysaccharide Pneumovax NP | 20 | Sarpogrelate hydrochloride | 100 | 5-HT2 antagonization | 30 |
| Ex. 375 | Sublingual | Solution | Pneumococcal capsular polysaccharide Pneumovax NP | 20 | Clopidogrel | 100 | P2Y12 antagonization | 30 |
| Ex. 376 | Sublingual | Solution | Pneumococcal capsular polysaccharide Pneumovax NP | 20 | Tiolopidine | 200 | | 30 |
| Ex. 377 | Sublingual | Solution | Pneumococcal capsular polysaccharide Pneumovax NP | 20 | Prasugrel | 100 | | 30 |
| Ex. 378 | Sublingual | Solution | Pneumococcal capsular polysaccharide Pneumovax NP | 20 | Apafant | 100 | PAF antagonization | 30 |
| Ex. 379 | Sublingual | Solution | Pneumococcal capsular polysaccharide Pneumovax NP | 20 | Naloxone | 100 | µ, κ, σ antagonization | 30 |
| Ex. 380 | Sublingual | Solution | Pneumococcal capsular polysaccharide Pneumovax NP | 20 | Zafirlukast | 100 | CysLT antagonization | 30 |
| Ex. 381 | Sublingual | Solution | Pneumococcal capsular polysaccharide Pneumovax NP | 20 | Montelukast | 100 | | 30 |
| Ex. 382 | Sublingual | Solution | Pneumococcal capsular polysaccharide Pneumovax NP | 20 | Pranlukast | 100 | | 30 |
| Ex. 383 | Sublingual | Solution | Pneumococcal capsular polysaccharide Pneumovax NP | 20 | Candesartan | 100 | AT1 antagonization | 30 |

TABLE 18

| | Administration route | Dosage form | Antigen Name | Amount [µg] | Th2 reaction promoter Name | Amount [µg] | Pharmacological effect | Amount [µL] |
|---|---|---|---|---|---|---|---|---|
| Comp. Ex. 35 | Transnasal | Solution | HPV16 recombinant protein | 10 | — | — | | 10 |
| Ex. 384 | Transnasal | Solution | HPV16 recombinant protein | 10 | Resveratrol | 40 | PDE inhibition | 10 |
| Ex. 385 | Transnasal | Solution | HPV16 recombinant protein | 10 | Vinpocetine | 20 | PDE inhibition | 10 |
| Ex. 386 | Transnasal | Solution | HPV16 recombinant protein | 10 | Pimobendan | 20 | PDE inhibition | 10 |
| Ex. 387 | Transnasal | Solution | HPV16 recombinant protein | 10 | BRL50481 | 20 | PDE inhibition | 10 |
| Ex. 388 | Transnasal | Solution | HPV16 recombinant protein | 10 | Dipyridamole | 40 | PDE inhibition | 10 |
| Ex. 389 | Transnasal | Solution | HPV16 recombinant protein | 10 | Methoxyphenamine hydrochloride | 20 | β2 activation | 10 |
| Ex. 390 | Transnasal | Solution | HPV16 recombinant protein | 10 | Fenoldopam mesylate | 20 | D1 activation | 10 |
| Ex. 391 | Transnasal | Solution | HPV16 recombinant protein | 10 | Cisapride | 20 | 5-HT4 activation | 10 |
| Ex. 392 | Transnasal | Solution | HPV16 recombinant protein | 10 | Desmopressin | 20 | V2 activation | 10 |
| Ex. 393 | Transnasal | Solution | HPV16 recombinant protein | 10 | Prazosin hydrochloride | 80 | α1,2 antagonization | 10 |
| Ex. 394 | Transnasal | Solution | HPV16 recombinant protein | 10 | Pirenzepine hycrochloride | 20 | M1 antagonization | 10 |
| Ex. 395 | Transnasal | Solution | HPV16 recombinant protein | 10 | Oxybutynin hydrochloride | 40 | M2 antagonization | 10 |
| Ex. 396 | Transnasal | Solution | HPV16 recombinant protein | 10 | Tolterodine tartrate | 80 | M3 antagonization | 10 |
| Ex. 397 | Transnasal | Solution | HPV16 recombinant protein | 10 | Fluphenazine | 10 | D2 antagonization | 10 |
| Ex. 398 | Transnasal | Solution | HPV16 recombinant protein | 10 | Droperidol | 20 | | 10 |
| Ex. 399 | Transnasal | Solution | HPV16 recombinant protein | 10 | Sulpiride | 20 | | 10 |

TABLE 18-continued

|  | Administration route | Dosage form | Antigen Name | Amount [μg] | Th2 reaction promoter Name | Amount [μg] | Pharmacological effect | Amount [μL] |
|---|---|---|---|---|---|---|---|---|
| Ex. 400 | Transnasal | Solution | HPV16 recombinant protein | 10 | Azelastine hydrochloride | 40 | H1 antagonization | 10 |
| Ex. 401 | Transnasal | Solution | HPV16 recombinant protein | 10 | Levocetirizine | 20 |  | 10 |
| Ex. 402 | Transnasal | Solution | HPV16 recombinant protein | 10 | Mequitazine | 20 |  | 10 |
| Ex. 403 | Transnasal | Solution | HPV16 recombinant protein | 10 | Thioperamide | 20 | H3 antagonization | 10 |
| Ex. 404 | Transnasal | Solution | HPV16 recombinant protein | 10 | Sarpogrelate hydrochloride | 20 | 5-HT2 antagonization | 10 |
| Ex. 405 | Transnasal | Solution | HPV16 recombinant protein | 10 | Clopidogrel | 20 | P2Y12 antagonization | 10 |
| Ex. 406 | Transnasal | Solution | HPV16 recombinant protein | 10 | Tiolopidine | 40 |  | 10 |
| Ex. 407 | Transnasal | Solution | HPV16 recombinant protein | 10 | Prasugrel | 20 |  | 10 |
| Ex. 408 | Transnasal | Solution | HPV16 recombinant protein | 10 | Apafant | 20 | PAF antagonization | 10 |
| Ex. 409 | Transnasal | Solution | HPV16 recombinant protein | 10 | Naloxone | 20 | μ, κ, σ antagonization | 10 |
| Ex. 410 | Transnasal | Solution | HPV16 recombinant protein | 10 | Zafirlukast | 20 | CysLT antagonization | 10 |
| Ex. 411 | Transnasal | Solution | HPV16 recombinant protein | 10 | Montelukast | 20 |  | 10 |
| Ex. 412 | Transnasal | Solution | HPV16 recombinant protein | 10 | Pranlukast | 20 |  | 10 |
| Ex. 413 | Transnasal | Solution | HPV16 recombinant protein | 10 | Candesartan | 20 | AT1 antagonization | 10 |

TABLE 19

|  | Administration route | Dosage form | Antigen Name | Amount [μg] | Th2 reaction promoter Name | Amount [μg] | Pharmacological effect | Amount [μL] |
|---|---|---|---|---|---|---|---|---|
| Comp. Ex. 36 | Sublingual | Solution | HPV16 recombinant protein | 10 | — | — |  | 30 |
| Ex. 414 | Sublingual | Solution | HPV16 recombinant protein | 10 | Resveratrol | 200 | PDE inhibition | 30 |
| Ex. 415 | Sublingual | Solution | HPV16 recombinant protein | 10 | Vinpocetine | 100 | PDE inhibition | 30 |
| Ex. 416 | Sublingual | Solution | HPV16 recombinant protein | 10 | Pimobendan | 100 | PDE inhibition | 30 |
| Ex. 417 | Sublingual | Solution | HPV16 recombinant protein | 10 | BRL50481 | 100 | PDE inhibition | 30 |
| Ex. 418 | Sublingual | Solution | HPV16 recombinant protein | 10 | Dipyridamole | 200 | PDE inhibition | 30 |
| Ex. 419 | Sublingual | Solution | HPV16 recombinant protein | 10 | Methoxyphenamine hydrochloride | 100 | β2 activation | 30 |
| Ex. 420 | Sublingual | Solution | HPV16 recombinant protein | 10 | Fenoldopam mesylate | 100 | D1 activation | 30 |
| Ex. 421 | Sublingual | Solution | HPV16 recombinant protein | 10 | Cisapride | 100 | 5-HT4 activation | 30 |
| Ex. 422 | Sublingual | Solution | HPV16 recombinant protein | 10 | Desmopressin | 100 | V2 activation | 30 |
| Ex. 423 | Sublingual | Solution | HPV16 recombinant protein | 10 | Prazosin hydrochloride | 400 | α1,2 antagonization | 30 |
| Ex. 424 | Sublingual | Solution | HPV16 recombinant protein | 10 | Pirenzepine hycrochloride | 100 | M1 antagonization | 30 |
| Ex. 425 | Sublingual | Solution | HPV16 recombinant protein | 10 | Oxybutynin hydrochloride | 200 | M2 antagonization | 30 |
| Ex. 426 | Sublingual | Solution | HPV16 recombinant protein | 10 | Tolterodine tartrate | 400 | M3 antagonization | 30 |
| Ex. 427 | Sublingual | Solution | HPV16 recombinant protein | 10 | Fluphenazine | 50 | D2 antagonization | 30 |
| Ex. 428 | Sublingual | Solution | HPV16 recombinant protein | 10 | Droperidol | 100 |  | 30 |
| Ex. 429 | Sublingual | Solution | HPV16 recombinant protein | 10 | Sulpiride | 100 |  | 30 |
| Ex. 430 | Sublingual | Solution | HPV16 recombinant protein | 10 | Azelastine hydrochloride | 200 | H1 antagonization | 30 |

TABLE 19-continued

| | Administration route | Dosage form | Antigen Name | Amount [μg] | Th2 reaction promoter Name | Amount [μg] | Pharmacological effect | Amount [μL] |
|---|---|---|---|---|---|---|---|---|
| Ex. 431 | Sublingual | Solution | HPV16 recombinant protein | 10 | Levocetirizine | 100 | | 30 |
| Ex. 432 | Sublingual | Solution | HPV16 recombinant protein | 10 | Mequitazine | 100 | | 30 |
| Ex. 433 | Sublingual | Solution | HPV16 recombinant protein | 10 | Thioperamide | 100 | H3 antagonization | 30 |
| Ex. 434 | Sublingual | Solution | HPV16 recombinant protein | 10 | Sarpogrelate hydrochloride | 100 | 5-HT2 antagonization | 30 |
| Ex. 435 | Sublingual | Solution | HPV16 recombinant protein | 10 | Clopidogrel | 100 | P2Y12 antagonization | 30 |
| Ex. 436 | Sublingual | Solution | HPV16 recombinant protein | 10 | Tiolopidine | 200 | | 30 |
| Ex. 437 | Sublingual | Solution | HPV16 recombinant protein | 10 | Prasugrel | 100 | | 30 |
| Ex. 438 | Sublingual | Solution | HPV16 recombinant protein | 10 | Apafant | 100 | PAF antagonization | 30 |
| Ex. 439 | Sublingual | Solution | HPV16 recombinant protein | 10 | Naloxone | 100 | μ, κ, σ antagonization | 30 |
| Ex. 440 | Sublingual | Solution | HPV16 recombinant protein | 10 | Zafirlukast | 100 | CysLT antagonization | 30 |
| Ex. 441 | Sublingual | Solution | HPV16 recombinant protein | 10 | Montelukast | 100 | | 30 |
| Ex. 442 | Sublingual | Solution | HPV16 recombinant protein | 10 | Pranlukast | 100 | | 30 |
| Ex. 443 | Sublingual | Solution | HPV16 recombinant protein | 10 | Candesartan | 100 | AT1 antagonization | 30 |

TABLE 20

| | Administration route | Dosage form | Antigen Name | Amount [μg] | Th2 reaction promoter Name | Amount [μg] | Pharmacological effect | Amount [μL] |
|---|---|---|---|---|---|---|---|---|
| Comp. Ex. 37 | Transnasal | Solution | Live attenuated rotavirus (RIX4414 strain) | 10 | — | — | | 10 |
| Ex. 444 | Transnasal | Solution | Live attenuated rotavirus (RIX4414 strain) | 10 | Resveratrol | 40 | PDE inhibition | 10 |
| Ex. 445 | Transnasal | Solution | Live attenuated rotavirus (RIX4414 strain) | 10 | Vinpocetine | 20 | PDE inhibition | 10 |
| Ex. 446 | Transnasal | Solution | Live attenuated rotavirus (RIX4414 strain) | 10 | Pimobendan | 20 | PDE inhibition | 10 |
| Ex. 447 | Transnasal | Solution | Live attenuated rotavirus (RIX4414 strain) | 10 | BRL50481 | 20 | PDE inhibition | 10 |
| Ex. 448 | Transnasal | Solution | Live attenuated rotavirus (RIX4414 strain) | 10 | Dipyridamole | 40 | PDE inhibition | 10 |
| Ex. 449 | Transnasal | Solution | Live attenuated rotavirus (RIX4414 strain) | 10 | Methoxyphenamine hydrochloride | 20 | β2 activation | 10 |
| Ex. 450 | Transnasal | Solution | Live attenuated rotavirus (RIX4414 strain) | 10 | Fenoldopam mesylate | 20 | D1 activation | 10 |
| Ex. 451 | Transnasal | Solution | Live attenuated rotavirus (RIX4414 strain) | 10 | Cisapride | 20 | 5-HT4 activation | 10 |
| Ex. 452 | Transnasal | Solution | Live attenuated rotavirus (RIX4414 strain) | 10 | Desmopressin | 20 | V2 activation | 10 |
| Ex. 453 | Transnasal | Solution | Live attenuated rotavirus (RIX4414 strain) | 10 | Prazosin hydrochloride | 80 | α1,2 antagonization | 10 |
| Ex. 454 | Transnasal | Solution | Live attenuated rotavirus (RIX4414 strain) | 10 | Pirenzepine hycrochloride | 20 | M1 antagonization | 10 |
| Ex. 455 | Transnasal | Solution | Live attenuated rotavirus (RIX4414 strain) | 10 | Oxybutynin hydrochloride | 40 | M2 antagonization | 10 |
| Ex. 456 | Transnasal | Solution | Live attenuated rotavirus (RIX4414 strain) | 10 | Tolterodine tartrate | 80 | M3 antagonization | 10 |
| Ex. 457 | Transnasal | Solution | Live attenuated rotavirus (RIX4414 strain) | 10 | Fluphenazine | 10 | D2 antagonization | 10 |
| Ex. 458 | Transnasal | Solution | Live attenuated rotavirus (RIX4414 strain) | 10 | Droperidol | 20 | | 10 |
| Ex. 459 | Transnasal | Solution | Live attenuated rotavirus (RIX4414 strain) | 10 | Sulpiride | 20 | | 10 |
| Ex. 460 | Transnasal | Solution | Live attenuated rotavirus (RIX4414 strain) | 10 | Azelastine hydrochloride | 40 | H1 antagonization | 10 |
| Ex. 461 | Transnasal | Solution | Live attenuated rotavirus (RIX4414 strain) | 10 | Levocetirizine | 20 | | 10 |

TABLE 20-continued

| | Administration route | Dosage form | Antigen Name | Amount [μg] | Th2 reaction promoter Name | Amount [μg] | Pharmacological effect | Amount [μL] |
|---|---|---|---|---|---|---|---|---|
| Ex. 462 | Transnasal | Solution | Live attenuated rotavirus (RIX4414 strain) | 10 | Mequitazine | 20 | | 10 |
| Ex. 463 | Transnasal | Solution | Live attenuated rotavirus (RIX4414 strain) | 10 | Thioperamide | 20 | H3 antagonization | 10 |
| Ex. 464 | Transnasal | Solution | Live attenuated rotavirus (RIX4414 strain) | 10 | Sarpogrelate hydrochloride | 20 | 5-HT2 antagonization | 10 |
| Ex. 465 | Transnasal | Solution | Live attenuated rotavirus (RIX4414 strain) | 10 | Clopidogrel | 20 | P2Y12 antagonization | 10 |
| Ex. 466 | Transnasal | Solution | Live attenuated rotavirus (RIX4414 strain) | 10 | Tiolopidine | 40 | | 10 |
| Ex. 467 | Transnasal | Solution | Live attenuated rotavirus (RIX4414 strain) | 10 | Prasugrel | 20 | | 10 |
| Ex. 468 | Transnasal | Solution | Live attenuated rotavirus (RIX4414 strain) | 10 | Apafant | 20 | PAF antagonization | 10 |
| Ex. 469 | Transnasal | Solution | Live attenuated rotavirus (RIX4414 strain) | 10 | Naloxone | 20 | μ, κ, σ antagonization | 10 |
| Ex. 470 | Transnasal | Solution | Live attenuated rotavirus (RIX4414 strain) | 10 | Zafirlukast | 20 | CysLT antagonization | 10 |
| Ex. 471 | Transnasal | Solution | Live attenuated rotavirus (RIX4414 strain) | 10 | Montelukast | 20 | | 10 |
| Ex. 472 | Transnasal | Solution | Live attenuated rotavirus (RIX4414 strain) | 10 | Pranlukast | 20 | | 10 |
| Ex. 473 | Transnasal | Solution | Live attenuated rotavirus (RIX4414 strain) | 10 | Candesartan | 20 | AT1 antagonization | 10 |

TABLE 21

| | Administration route | Dosage form | Antigen Name | Amount [μg] | Th2 reaction promoter Name | Amount [μg] | Pharmacological effect | Amount [μL] |
|---|---|---|---|---|---|---|---|---|
| Comp. Ex. 38 | Sublingual | Solution | Live attenuated rotavirus (RIX4414 strain) | 10 | — | — | | 30 |
| Ex. 474 | Sublingual | Solution | Live attenuated rotavirus (RIX4414 strain) | 10 | Resveratrol | 200 | PDE inhibition | 30 |
| Ex. 475 | Sublingual | Solution | Live attenuated rotavirus (RIX4414 strain) | 10 | Vinpocetine | 100 | PDE inhibition | 30 |
| Ex. 476 | Sublingual | Solution | Live attenuated rotavirus (RIX4414 strain) | 10 | Pimobendan | 100 | PDE inhibition | 30 |
| Ex. 477 | Sublingual | Solution | Live attenuated rotavirus (RIX4414 strain) | 10 | BRL50481 | 100 | PDE inhibition | 30 |
| Ex. 478 | Sublingual | Solution | Live attenuated rotavirus (RIX4414 strain) | 10 | Dipyridamole | 200 | PDE inhibition | 30 |
| Ex. 479 | Sublingual | Solution | Live attenuated rotavirus (RIX4414 strain) | 10 | Methoxyphenamine hydrochloride | 100 | β2 activation | 30 |
| Ex. 480 | Sublingual | Solution | Live attenuated rotavirus (RIX4414 strain) | 10 | Fenoldopam mesylate | 100 | D1 activation | 30 |
| Ex. 481 | Sublingual | Solution | Live attenuated rotavirus (RIX4414 strain) | 10 | Cisapride | 100 | 5-HT4 activation | 30 |
| Ex. 482 | Sublingual | Solution | Live attenuated rotavirus (RIX4414 strain) | 10 | Desmopressin | 100 | V2 activation | 30 |
| Ex. 483 | Sublingual | Solution | Live attenuated rotavirus (RIX4414 strain) | 10 | Prazosin hydrochloride | 400 | α1,2 antagonization | 30 |
| Ex. 484 | Sublingual | Solution | Live attenuated rotavirus (RIX4414 strain) | 10 | Pirenzepine hydrochloride | 100 | M1 antagonization | 30 |
| Ex. 485 | Sublingual | Solution | Live attenuated rotavirus (RIX4414 strain) | 10 | Oxybutynin hydrochloride | 200 | M2 antagonization | 30 |
| Ex. 486 | Sublingual | Solution | Live attenuated rotavirus (RIX4414 strain) | 10 | Tolterodine tartrate | 400 | M3 antagonization | 30 |
| Ex. 487 | Sublingual | Solution | Live attenuated rotavirus (RIX4414 strain) | 10 | Fluphenazine | 50 | D2 antagonization | 30 |
| Ex. 488 | Sublingual | Solution | Live attenuated rotavirus (RIX4414 strain) | 10 | Droperidol | 100 | | 30 |
| Ex. 489 | Sublingual | Solution | Live attenuated rotavirus (RIX4414 strain) | 10 | Sulpiride | 100 | | 30 |
| Ex. 490 | Sublingual | Solution | Live attenuated rotavirus (RIX4414 strain) | 10 | Azelastine hydrochloride | 200 | H1 antagonization | 30 |
| Ex. 491 | Sublingual | Solution | Live attenuated rotavirus (RIX4414 strain) | 10 | Levocetirizine | 100 | | 30 |
| Ex. 492 | Sublingual | Solution | Live attenuated rotavirus (RIX4414 strain) | 10 | Mequitazine | 100 | | 30 |

TABLE 21-continued

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Ex. 493 | Sublingual | Solution | Live attenuated rotavirus (RIX4414 strain) | 10 | Thioperamide | 100 | H3 antagonization | 30 |
| Ex. 494 | Sublingual | Solution | Live attenuated rotavirus (RIX4414 strain) | 10 | Sarpogrelate hydrochloride | 100 | 5-HT2 antagonization | 30 |
| Ex. 495 | Sublingual | Solution | Live attenuated rotavirus (RIX4414 strain) | 10 | Clopidogrel | 100 | P2Y12 antagonization | 30 |
| Ex. 496 | Sublingual | Solution | Live attenuated rotavirus (RIX4414 strain) | 10 | Ticlopidine | 200 | | 30 |
| Ex. 497 | Sublingual | Solution | Live attenuated rotavirus (RIX4414 strain) | 10 | Prasugrel | 100 | | 30 |
| Ex. 498 | Sublingual | Solution | Live attenuated rotavirus (RIX4414 strain) | 10 | Apafant | 100 | PAF antagonization | 30 |
| Ex. 499 | Sublingual | Solution | Live attenuated rotavirus (RIX4414 strain) | 10 | Naloxone | 100 | μ, κ, σ antagonization | 30 |
| Ex. 500 | Sublingual | Solution | Live attenuated rotavirus (RIX4414 strain) | 10 | Zafirlukast | 100 | CysLT antagonization | 30 |
| Ex. 501 | Sublingual | Solution | Live attenuated rotavirus (RIX4414 strain) | 10 | Montelukast | 100 | | 30 |
| Ex. 502 | Sublingual | Solution | Live attenuated rotavirus (RIX4414 strain) | 10 | Pranlukast | 100 | | 30 |
| Ex. 503 | Sublingual | Solution | Live attenuated rotavirus (RIX4414 strain) | 10 | Candesartan | 100 | AT1 antagonization | 30 |

TABLE 22

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 39 | Transnasal | Solution | Inactivated poliovirus (type 1, type 2, and type 3) | Vaccine 100 μL equivalent | — | — | | 10 |
| Ex. 504 | Transnasal | Solution | Inactivated poliovirus (type 1, type 2, and type 3) | Vaccine 100 μL equivalent | Resveratrol | 40 | PDE inhibition | 10 |
| Ex. 505 | Transnasal | Solution | Inactivated poliovirus (type 1, type 2, and type 3) | Vaccine 100 μL equivalent | Vinpocetine | 20 | PDE inhibition | 10 |
| Ex. 506 | Transnasal | Solution | Inactivated poliovirus (type 1, type 2, and type 3) | Vaccine 100 μL equivalent | Pimobendan | 20 | PDE inhibition | 10 |
| Ex. 507 | Transnasal | Solution | Inactivated poliovirus (type 1, type 2, and type 3) | Vaccine 100 μL equivalent | BRL50481 | 20 | PDE inhibition | 10 |
| Ex. 508 | Transnasal | Solution | Inactivated poliovirus (type 1, type 2, and type 3) | Vaccine 100 μL equivalent | Dipyridamole | 40 | PDE inhibition | 10 |
| Ex. 509 | Transnasal | Solution | Inactivated poliovirus (type 1, type 2, and type 3) | Vaccine 100 μL equivalent | Methoxyphenamine hydrochloride | 20 | β2 activation | 10 |
| Ex. 510 | Transnasal | Solution | Inactivated poliovirus (type 1, type 2, and type 3) | Vaccine 100 μL equivalent | Fenoldopam mesylate | 20 | D1 activation | 10 |
| Ex. 511 | Transnasal | Solution | Inactivated poliovirus (type 1, type 2, and type 3) | Vaccine 100 μL equivalent | Cisapride | 20 | 5-HT4 activation | 10 |
| Ex. 512 | Transnasal | Solution | Inactivated poliovirus (type 1, type 2, and type 3) | Vaccine 100 μL equivalent | Desmopressin | 20 | V2 activation | 10 |
| Ex. 513 | Transnasal | Solution | Inactivated poliovirus (type 1, type 2, and type 3) | Vaccine 100 μL equivalent | Prazosin hydrochloride | 80 | α1,2 antagonization | 10 |
| Ex. 514 | Transnasal | Solution | Inactivated poliovirus (type 1, type 2, and type 3) | Vaccine 100 μL equivalent | Pirenzepine hydrochloride | 20 | M1 antagonization | 10 |
| Ex. 515 | Transnasal | Solution | Inactivated poliovirus (type 1, type 2, and type 3) | Vaccine 100 μL equivalent | Oxybutynin hydrochloride | 40 | M2 antagonization | 10 |
| Ex. 516 | Transnasal | Solution | Inactivated poliovirus (type 1, type 2, and type 3) | Vaccine 100 μL equivalent | Tolterodine tartrate | 80 | M3 antagonization | 10 |
| Ex. 517 | Transnasal | Solution | Inactivated poliovirus (type 1, type 2, and type 3) | Vaccine 100 μL equivalent | Fluphenazine | 10 | D2 antagonization | 10 |
| Ex. 518 | Transnasal | Solution | Inactivated poliovirus (type 1, type 2, and type 3) | Vaccine 100 μL equivalent | Droperidol | 20 | | 10 |
| Ex. 519 | Transnasal | Solution | Inactivated poliovirus (type 1, type 2, and type 3) | Vaccine 100 μL equivalent | Sulpiride | 20 | | 10 |
| Ex. 520 | Transnasal | Solution | Inactivated poliovirus (type 1, type 2, and type 3) | Vaccine 100 μL equivalent | Azelastine hydrochloride | 40 | H1 antagonization | 10 |
| Ex. 521 | Transnasal | Solution | Inactivated poliovirus (type 1, type 2, and type 3) | Vaccine 100 μL equivalent | Levocetirizine | 20 | | 10 |
| Ex. 522 | Transnasal | Solution | Inactivated poliovirus (type 1, type 2, and type 3) | Vaccine 100 μL equivalent | Mequitazine | 20 | | 10 |
| Ex. 523 | Transnasal | Solution | Inactivated poliovirus (type 1, type 2, and type 3) | Vaccine 100 μL equivalent | Thioperamide | 20 | H3 antagonization | 10 |

TABLE 22-continued

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Ex. 524 | Transnasal | Solution | Inactivated poliovirus (type 1, type 2, and type 3) | Vaccine 100 μL equivalent | Sarpogrelate hydrochloride | 20 | 5-HT2 antagonization | 10 |
| Ex. 525 | Transnasal | Solution | Inactivated poliovirus (type 1, type 2, and type 3) | Vaccine 100 μL equivalent | Clopidogrel | 20 | P2Y12 antagonization | 10 |
| Ex. 526 | Transnasal | Solution | Inactivated poliovirus (type 1, type 2, and type 3) | Vaccine 100 μL equivalent | Ticlopidine | 40 | | 10 |
| Ex. 527 | Transnasal | Solution | Inactivated poliovirus (type 1, type 2, and type 3) | Vaccine 100 μL equivalent | Prasugrel | 20 | | 10 |
| Ex. 528 | Transnasal | Solution | Inactivated poliovirus (type 1, type 2, and type 3) | Vaccine 100 μL equivalent | Apafant | 20 | PAF antagonization | 10 |
| Ex. 529 | Transnasal | Solution | Inactivated poliovirus (type 1, type 2, and type 3) | Vaccine 100 μL equivalent | Naloxone | 20 | μ, κ, σ antagonization | 10 |
| Ex. 530 | Transnasal | Solution | Inactivated poliovirus (type 1, type 2, and type 3) | Vaccine 100 μL equivalent | Zafirlukast | 20 | CysLT antagonization | 10 |
| Ex. 531 | Transnasal | Solution | Inactivated poliovirus (type 1, type 2, and type 3) | Vaccine 100 μL equivalent | Montelukast | 20 | | 10 |
| Ex. 532 | Transnasal | Solution | Inactivated poliovirus (type 1, type 2, and type 3) | Vaccine 100 μL equivalent | Pranlukast | 20 | | 10 |
| Ex. 533 | Transnasal | Solution | Inactivated poliovirus (type 1, type 2, and type 3) | Vaccine 100 μL equivalent | Candesartan | 20 | AT1 antagonization | 10 |

TABLE 23

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 40 | Sublingual | Solution | Inactivated poliovirus (type 1, type 2, and type 3) | Vaccine 100 μL equivalent | — | — | | 30 |
| Ex. 534 | Sublingual | Solution | Inactivated poliovirus (type 1, type 2, and type 3) | Vaccine 100 μL equivalent | Resveratrol | 200 | PDE inhibition | 30 |
| Ex. 535 | Sublingual | Solution | Inactivated poliovirus (type 1, type 2, and type 3) | Vaccine 100 μL equivalent | Vinpocetine | 100 | PDE inhibition | 30 |
| Ex. 536 | Sublingual | Solution | Inactivated poliovirus (type 1, type 2, and type 3) | Vaccine 100 μL equivalent | Pimobendan | 100 | PDE inhibition | 30 |
| Ex. 537 | Sublingual | Solution | Inactivated poliovirus (type 1, type 2, and type 3) | Vaccine 100 μL equivalent | BRL50481 | 100 | PDE inhibition | 30 |
| Ex. 538 | Sublingual | Solution | Inactivated poliovirus (type 1, type 2, and type 3) | Vaccine 100 μL equivalent | Dipyridamole | 200 | PDE inhibition | 30 |
| Ex. 539 | Sublingual | Solution | Inactivated poliovirus (type 1, type 2, and type 3) | Vaccine 100 μL equivalent | Methoxyphenamine hydrochloride | 100 | β2 activation | 30 |
| Ex. 540 | Sublingual | Solution | Inactivated poliovirus (type 1, type 2, and type 3) | Vaccine 100 μL equivalent | Fenoldopam mesylate | 100 | D1 activation | 30 |
| Ex. 541 | Sublingual | Solution | Inactivated poliovirus (type 1, type 2, and type 3) | Vaccine 100 μL equivalent | Cisapride | 100 | 5-HT4 activation | 30 |
| Ex. 542 | Sublingual | Solution | Inactivated poliovirus (type 1, type 2, and type 3) | Vaccine 100 μL equivalent | Desmopressin | 100 | V2 activation | 30 |
| Ex. 543 | Sublingual | Solution | Inactivated poliovirus (type 1, type 2, and type 3) | Vaccine 100 μL equivalent | Prazosin hydrochloride | 400 | α1,2 antagonization | 30 |
| Ex. 544 | Sublingual | Solution | Inactivated poliovirus (type 1, type 2, and type 3) | Vaccine 100 μL equivalent | Pirenzepine hydrochloride | 100 | M1 antagonization | 30 |
| Ex. 545 | Sublingual | Solution | Inactivated poliovirus (type 1, type 2, and type 3) | Vaccine 100 μL equivalent | Oxybutynin hydrochloride | 200 | M2 antagonization | 30 |
| Ex. 546 | Sublingual | Solution | Inactivated poliovirus (type 1, type 2, and type 3) | Vaccine 100 μL equivalent | Tolterodine tartrate | 400 | M3 antagonization | 30 |
| Ex. 547 | Sublingual | Solution | Inactivated poliovirus (type 1, type 2, and type 3) | Vaccine 100 μL equivalent | Fluphenazine | 50 | D2 antagonization | 30 |
| Ex. 548 | Sublingual | Solution | Inactivated poliovirus (type 1, type 2, and type 3) | Vaccine 100 μL equivalent | Droperidol | 100 | | 30 |
| Ex. 549 | Sublingual | Solution | Inactivated poliovirus (type 1, type 2, and type 3) | Vaccine 100 μL equivalent | Sulpiride | 100 | | 30 |
| Ex. 550 | Sublingual | Solution | Inactivated poliovirus (type 1, type 2, and type 3) | Vaccine 100 μL equivalent | Azelastine hydrochloride | 200 | H1 antagonization | 30 |
| Ex. 551 | Sublingual | Solution | Inactivated poliovirus (type 1, type 2, and type 3) | Vaccine 100 μL equivalent | Levocetirizine | 100 | | 30 |
| Ex. 552 | Sublingual | Solution | Inactivated poliovirus (type 1, type 2, and type 3) | Vaccine 100 μL equivalent | Mequitazine | 100 | | 30 |
| Ex. 553 | Sublingual | Solution | Inactivated poliovirus (type 1, type 2, and type 3) | Vaccine 100 μL equivalent | Thioperamide | 100 | H3 antagonization | 30 |
| Ex. 554 | Sublingual | Solution | Inactivated poliovirus (type 1, type 2, and type 3) | Vaccine 100 μL equivalent | Sarpogrelate hydrochloride | 100 | 5-HT2 antagonization | 30 |

TABLE 23-continued

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Ex. 555 | Sublingual | Solution | Inactivated poliovirus (type 1, type 2, and type 3) | Vaccine 100 μL equivalent | Clopidogrel | 100 | P2Y12 antagonization | 30 |
| Ex. 556 | Sublingual | Solution | Inactivated poliovirus (type 1, type 2, and type 3) | Vaccine 100 μL equivalent | Ticlopidine | 200 | | 30 |
| Ex. 557 | Sublingual | Solution | Inactivated poliovirus (type 1, type 2, and type 3) | Vaccine 100 μL equivalent | Prasugrel | 100 | | 30 |
| Ex. 558 | Sublingual | Solution | Inactivated poliovirus (type 1, type 2, and type 3) | Vaccine 100 μL equivalent | Apafant | 100 | PAF antagonization | 30 |
| Ex. 589 | Sublingual | Solution | Inactivated poliovirus (type 1, type 2, and type 3) | Vaccine 100 μL equivalent | Naloxone | 100 | μ, κ, σ antagonization | 30 |
| Ex. 560 | Sublingual | Solution | Inactivated poliovirus (type 1, type 2, and type 3) | Vaccine 100 μL equivalent | Zafirlukast | 100 | CysLT antagonization | 30 |
| Ex. 561 | Sublingual | Solution | Inactivated poliovirus (type 1, type 2, and type 3) | Vaccine 100 μL equivalent | Montelukast | 100 | | 30 |
| Ex. 562 | Sublingual | Solution | Inactivated poliovirus (type 1, type 2, and type 3) | Vaccine 100 μL equivalent | Pranlukast | 100 | | 30 |
| Ex. 563 | Sublingual | Solution | Inactivated poliovirus (type 1, type 2, and type 3) | Vaccine 100 μL equivalent | Candesartan | 100 | AT1 antagonization | 30 |

TABLE 24

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 41 | Transnasal | Solution | Inactivated hepatitis A virus | Vaccine 100 μL equivalent | — | — | | 10 |
| Ex. 564 | Transnasal | Solution | Inactivated hepatitis A virus | Vaccine 100 μL equivalent | Resveratrol | 40 | PDE inhibition | 10 |
| Ex. 565 | Transnasal | Solution | Inactivated hepatitis A virus | Vaccine 100 μL equivalent | Vinpocetine | 20 | PDE inhibition | 10 |
| Ex. 566 | Transnasal | Solution | Inactivated hepatitis A virus | Vaccine 100 μL equivalent | Pimobendan | 20 | PDE inhibition | 10 |
| Ex. 567 | Transnasal | Solution | Inactivated hepatitis A virus | Vaccine 100 μL equivalent | BRL50481 | 20 | PDE inhibition | 10 |
| Ex. 568 | Transnasal | Solution | Inactivated hepatitis A virus | Vaccine 100 μL equivalent | Dipyridamole | 40 | PDE inhibition | 10 |
| Ex. 569 | Transnasal | Solution | Inactivated hepatitis A virus | Vaccine 100 μL equivalent | Methoxyphenamine hydrochloride | 20 | β2 activation | 10 |
| Ex. 570 | Transnasal | Solution | Inactivated hepatitis A virus | Vaccine 100 μL equivalent | Fenoldopam mesylate | 20 | D1 activation | 10 |
| Ex. 571 | Transnasal | Solution | Inactivated hepatitis A virus | Vaccine 100 μL equivalent | Cisapride | 20 | 5-HT4 activation | 10 |
| Ex. 572 | Transnasal | Solution | Inactivated hepatitis A virus | Vaccine 100 μL equivalent | Desmopressin | 20 | V2 activation | 10 |
| Ex. 573 | Transnasal | Solution | Inactivated hepatitis A virus | Vaccine 100 μL equivalent | Prazosin hydrochloride | 80 | α1,2 antagonization | 10 |
| Ex. 574 | Transnasal | Solution | Inactivated hepatitis A virus | Vaccine 100 μL equivalent | Pirenzepine hydrochloride | 20 | M1 antagonization | 10 |
| Ex. 575 | Transnasal | Solution | Inactivated hepatitis A virus | Vaccine 100 μL equivalent | Oxybutynin hydrochloride | 40 | M2 antagonization | 10 |
| Ex. 576 | Transnasal | Solution | Inactivated hepatitis A virus | Vaccine 100 μL equivalent | Tolterodine tartrate | 80 | M3 antagonization | 10 |
| Ex. 577 | Transnasal | Solution | Inactivated hepatitis A virus | Vaccine 100 μL equivalent | Fluphenazine | 10 | D2 antagonization | 10 |
| Ex. 578 | Transnasal | Solution | Inactivated hepatitis A virus | Vaccine 100 μL equivalent | Droperidol | 20 | | 10 |
| Ex. 579 | Transnasal | Solution | Inactivated hepatitis A virus | Vaccine 100 μL equivalent | Sulpiride | 20 | | 10 |
| Ex. 580 | Transnasal | Solution | Inactivated hepatitis A virus | Vaccine 100 μL equivalent | Azelastine hydrochloride | 40 | H1 antagonization | 10 |
| Ex. 581 | Transnasal | Solution | Inactivated hepatitis A virus | Vaccine 100 μL equivalent | Levocetirizine | 20 | | 10 |
| Ex. 582 | Transnasal | Solution | Inactivated hepatitis A virus | Vaccine 100 μL equivalent | Mequitazine | 20 | | 10 |
| Ex. 583 | Transnasal | Solution | Inactivated hepatitis A virus | Vaccine 100 μL equivalent | Thioperamide | 20 | H3 antagonization | 10 |
| Ex. 584 | Transnasal | Solution | Inactivated hepatitis A virus | Vaccine 100 μL equivalent | Sarpogrelate hydrochloride | 20 | 5-HT2 antagonization | 10 |
| Ex. 585 | Transnasal | Solution | Inactivated hepatitis A virus | Vaccine 100 μL equivalent | Clopidogrel | 20 | P2Y12 antagonization | 10 |

TABLE 24-continued

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Ex. 586 | Transnasal | Solution | Inactivated hepatitis A virus | Vaccine 100 μL equivalent | Ticlopidine | 40 | | 10 |
| Ex. 587 | Transnasal | Solution | Inactivated hepatitis A virus | Vaccine 100 μL equivalent | Prasugrel | 20 | | 10 |
| Ex. 588 | Transnasal | Solution | Inactivated hepatitis A virus | Vaccine 100 μL equivalent | Apafant | 20 | PAF antagonization | 10 |
| Ex. 589 | Transnasal | Solution | Inactivated hepatitis A virus | Vaccine 100 μL equivalent | Naloxone | 20 | μ, κ, σ antagonization | 10 |
| Ex. 590 | Transnasal | Solution | Inactivated hepatitis A virus | Vaccine 100 μL equivalent | Zafirlukast | 20 | CysLT antagonization | 10 |
| Ex. 591 | Transnasal | Solution | Inactivated hepatitis A virus | Vaccine 100 μL equivalent | Montelukast | 20 | | 10 |
| Ex. 592 | Transnasal | Solution | Inactivated hepatitis A virus | Vaccine 100 μL equivalent | Pranlukast | 20 | | 10 |
| Ex. 593 | Transnasal | Solution | Inactivated hepatitis A virus | Vaccine 100 μL equivalent | Candesartan | 20 | AT1 antagonization | 10 |

TABLE 25

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 42 | Sublingual | Solution | Inactivated hepatitis A virus | Vaccine 100 μL equivalent | — | — | | 30 |
| Ex. 594 | Sublingual | Solution | Inactivated hepatitis A virus | Vaccine 100 μL equivalent | Resveratrol | 200 | PDE inhibition | 30 |
| Ex. 595 | Sublingual | Solution | Inactivated hepatitis A virus | Vaccine 100 μL equivalent | Vinpocetine | 100 | PDE inhibition | 30 |
| Ex. 596 | Sublingual | Solution | Inactivated hepatitis A virus | Vaccine 100 μL equivalent | Pimobendan | 100 | PDE inhibition | 30 |
| Ex. 597 | Sublingual | Solution | Inactivated hepatitis A virus | Vaccine 100 μL equivalent | BRL50481 | 100 | PDE inhibition | 30 |
| Ex. 598 | Sublingual | Solution | Inactivated hepatitis A virus | Vaccine 100 μL equivalent | Dipyridamole | 200 | PDE inhibition | 30 |
| Ex. 599 | Sublingual | Solution | Inactivated hepatitis A virus | Vaccine 100 μL equivalent | Methoxyphenamine hydrochloride | 100 | β2 activation | 30 |
| Ex. 600 | Sublingual | Solution | Inactivated hepatitis A virus | Vaccine 100 μL equivalent | Fenoldopam mesylate | 100 | D1 activation | 30 |
| Ex. 601 | Sublingual | Solution | Inactivated hepatitis A virus | Vaccine 100 μL equivalent | Cisapride | 100 | 5-HT4 activation | 30 |
| Ex. 602 | Sublingual | Solution | Inactivated hepatitis A virus | Vaccine 100 μL equivalent | Desmopressin | 100 | V2 activation | 30 |
| Ex. 603 | Sublingual | Solution | Inactivated hepatitis A virus | Vaccine 100 μL equivalent | Prazosin hydrochloride | 400 | α1,2 antagonization | 30 |
| Ex. 604 | Sublingual | Solution | Inactivated hepatitis A virus | Vaccine 100 μL equivalent | Pirenzepine hydrochloride | 100 | M1 antagonization | 30 |
| Ex. 605 | Sublingual | Solution | Inactivated hepatitis A virus | Vaccine 100 μL equivalent | Oxybutynin hydrochloride | 200 | M2 antagonization | 30 |
| Ex. 606 | Sublingual | Solution | Inactivated hepatitis A virus | Vaccine 100 μL equivalent | Tolterodine tartrate | 400 | M3 antagonization | 30 |
| Ex. 607 | Sublingual | Solution | Inactivated hepatitis A virus | Vaccine 100 μL equivalent | Fluphenazine | 50 | D2 antagonization | 30 |
| Ex. 608 | Sublingual | Solution | Inactivated hepatitis A virus | Vaccine 100 μL equivalent | Droperidol | 100 | | 30 |
| Ex. 609 | Sublingual | Solution | Inactivated hepatitis A virus | Vaccine 100 μL equivalent | Sulpiride | 100 | | 30 |
| Ex. 610 | Sublingual | Solution | Inactivated hepatitis A virus | Vaccine 100 μL equivalent | Azelastine hydrochloride | 200 | H1 antagonization | 30 |
| Ex. 611 | Sublingual | Solution | Inactivated hepatitis A virus | Vaccine 100 μL equivalent | Levocetirizine | 100 | | 30 |
| Ex. 612 | Sublingual | Solution | Inactivated hepatitis A virus | Vaccine 100 μL equivalent | Mequitazine | 100 | | 30 |
| Ex. 613 | Sublingual | Solution | Inactivated hepatitis A virus | Vaccine 100 μL equivalent | Thioperamide | 100 | H3 antagonization | 30 |
| Ex. 614 | Sublingual | Solution | Inactivated hepatitis A virus | Vaccine 100 μL equivalent | Sarpogrelate hydrochloride | 100 | 5-HT2 antagonization | 30 |
| Ex. 615 | Sublingual | Solution | Inactivated hepatitis A virus | Vaccine 100 μL equivalent | Clopidogrel | 100 | P2Y12 antagonization | 30 |
| Ex. 616 | Sublingual | Solution | Inactivated hepatitis A virus | Vaccine 100 μL equivalent | Ticlopidine | 200 | | 30 |

TABLE 25-continued

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Ex. 617 | Sublingual | Solution | Inactivated hepatitis A virus | Vaccine 100 μL equivalent | Prasugrel | 100 | | 30 |
| Ex. 618 | Sublingual | Solution | Inactivated hepatitis A virus | Vaccine 100 μL equivalent | Apafant | 100 | PAF antagonization | 30 |
| Ex. 619 | Sublingual | Solution | Inactivated hepatitis A virus | Vaccine 100 μL equivalent | Naloxone | 100 | μ, κ, σ antagonization | 30 |
| Ex. 620 | Sublingual | Solution | Inactivated hepatitis A virus | Vaccine 100 μL equivalent | Zafirlukast | 100 | CysLT antagonization | 30 |
| Ex. 621 | Sublingual | Solution | Inactivated hepatitis A virus | Vaccine 100 μL equivalent | Montelukast | 100 | | 30 |
| Ex. 622 | Sublingual | Solution | Inactivated hepatitis A virus | Vaccine 100 μL equivalent | Pranlukast | 100 | | 30 |
| Ex. 623 | Sublingual | Solution | Inactivated hepatitis A virus | Vaccine 100 μL equivalent | Candesartan | 100 | AT1 antagonization | 30 |

TABLE 26

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 43 | Transnasal | Solution | Inactivated Japanese encephalitis virus | Vaccine 100 μL equivalent | — | — | | 10 |
| Ex. 624 | Transnasal | Solution | Inactivated Japanese encephalitis virus | Vaccine 100 μL equivalent | Resveratrol | 40 | PDE inhibition | 10 |
| Ex. 625 | Transnasal | Solution | Inactivated Japanese encephalitis virus | Vaccine 100 μL equivalent | Vinpocetine | 20 | PDE inhibition | 10 |
| Ex. 626 | Transnasal | Solution | Inactivated Japanese encephalitis virus | Vaccine 100 μL equivalent | Pimobendan | 20 | PDE inhibition | 10 |
| Ex. 627 | Transnasal | Solution | Inactivated Japanese encephalitis virus | Vaccine 100 μL equivalent | BRL50481 | 20 | PDE inhibition | 10 |
| Ex. 628 | Transnasal | Solution | Inactivated Japanese encephalitis virus | Vaccine 100 μL equivalent | Dipyridamole | 40 | PDE inhibition | 10 |
| Ex. 629 | Transnasal | Solution | Inactivated Japanese encephalitis virus | Vaccine 100 μL equivalent | Methoxyphenamine hydrochloride | 20 | β2 activation | 10 |
| Ex. 630 | Transnasal | Solution | Inactivated Japanese encephalitis virus | Vaccine 100 μL equivalent | Fenoldopam mesylate | 20 | D1 activation | 10 |
| Ex. 631 | Transnasal | Solution | Inactivated Japanese encephalitis virus | Vaccine 100 μL equivalent | Cisapride | 20 | 5-HT4 activation | 10 |
| Ex. 632 | Transnasal | Solution | Inactivated Japanese encephalitis virus | Vaccine 100 μL equivalent | Desmopressin | 20 | V2 activation | 10 |
| Ex. 633 | Transnasal | Solution | Inactivated Japanese encephalitis virus | Vaccine 100 μL equivalent | Prazosin hydrochloride | 80 | α1,2 antagonization | 10 |
| Ex. 634 | Transnasal | Solution | Inactivated Japanese encephalitis virus | Vaccine 100 μL equivalent | Pirenzepine hydrochloride | 20 | M1 antagonization | 10 |
| Ex. 635 | Transnasal | Solution | Inactivated Japanese encephalitis virus | Vaccine 100 μL equivalent | Oxybutynin hydrochloride | 40 | M2 antagonization | 10 |
| Ex. 636 | Transnasal | Solution | Inactivated Japanese encephalitis virus | Vaccine 100 μL equivalent | Tolterodine tartrate | 80 | M3 antagonization | 10 |
| Ex. 637 | Transnasal | Solution | Inactivated Japanese encephalitis virus | Vaccine 100 μL equivalent | Fluphenazine | 10 | D2 antagonization | 10 |
| Ex. 638 | Transnasal | Solution | Inactivated Japanese encephalitis virus | Vaccine 100 μL equivalent | Droperidol | 20 | | 10 |
| Ex. 639 | Transnasal | Solution | Inactivated Japanese encephalitis virus | Vaccine 100 μL equivalent | Sulpiride | 20 | | 10 |
| Ex. 640 | Transnasal | Solution | Inactivated Japanese encephalitis virus | Vaccine 100 μL equivalent | Azelastine hydrochloride | 40 | H1 antagonization | 10 |
| Ex. 641 | Transnasal | Solution | Inactivated Japanese encephalitis virus | Vaccine 100 μL equivalent | Levocetirizine | 20 | | 10 |
| Ex. 642 | Transnasal | Solution | Inactivated Japanese encephalitis virus | Vaccine 100 μL equivalent | Mequitazine | 20 | | 10 |
| Ex. 643 | Transnasal | Solution | Inactivated Japanese encephalitis virus | Vaccine 100 μL equivalent | Thioperamide | 20 | H3 antagonization | 10 |
| Ex. 644 | Transnasal | Solution | Inactivated Japanese encephalitis virus | Vaccine 100 μL equivalent | Sarpogrelate hydrochloride | 20 | 5-HT2 antagonization | 10 |
| Ex. 645 | Transnasal | Solution | Inactivated Japanese encephalitis virus | Vaccine 100 μL equivalent | Clopidogrel | 20 | P2Y12 antagonization | 10 |
| Ex. 646 | Transnasal | Solution | Inactivated Japanese encephalitis virus | Vaccine 100 μL equivalent | Ticlopidine | 40 | | 10 |
| Ex. 647 | Transnasal | Solution | Inactivated Japanese encephalitis virus | Vaccine 100 μL equivalent | Prasugrel | 20 | | 10 |

TABLE 26-continued

| | Administration route | Dosage form | Antigen Name | Amount [μg] | Th2 reaction promoter Name | Amount [μg] | Pharmacological effect | Amount [μL] |
|---|---|---|---|---|---|---|---|---|
| Ex. 648 | Transnasal | Solution | Inactivated Japanese encephalitis virus | Vaccine 100 μL equivalent | Apafant | 20 | PAF antagonization | 10 |
| Ex. 649 | Transnasal | Solution | Inactivated Japanese encephalitis virus | Vaccine 100 μL equivalent | Naloxone | 20 | μ, κ, σ antagonization | 10 |
| Ex. 650 | Transnasal | Solution | Inactivated Japanese encephalitis virus | Vaccine 100 μL equivalent | Zafirlukast | 20 | CysLT antagonization | 10 |
| Ex. 651 | Transnasal | Solution | Inactivated Japanese encephalitis virus | Vaccine 100 μL equivalent | Montelukast | 20 | | 10 |
| Ex. 652 | Transnasal | Solution | Inactivated Japanese encephalitis virus | Vaccine 100 μL equivalent | Pranlukast | 20 | | 10 |
| Ex. 653 | Transnasal | Solution | Inactivated Japanese encephalitis virus | Vaccine 100 μL equivalent | Candesartan | 20 | AT1 antagonization | 10 |

TABLE 27

| | Administration route | Dosage form | Antigen Name | Amount [μg] | Th2 reaction promoter Name | Amount [μg] | Pharmacological effect | Amount [μL] |
|---|---|---|---|---|---|---|---|---|
| Comp. Ex. 44 | Sublingual | Solution | Inactivated Japanese encephalitis virus | Vaccine 100 μL equivalent | — | — | | 30 |
| Ex. 654 | Sublingual | Solution | Inactivated Japanese encephalitis virus | Vaccine 100 μL equivalent | Resveratrol | 200 | PDE inhibition | 30 |
| Ex. 655 | Sublingual | Solution | Inactivated Japanese encephalitis virus | Vaccine 100 μL equivalent | Vinpocetine | 100 | PDE inhibition | 30 |
| Ex. 656 | Sublingual | Solution | Inactivated Japanese encephalitis virus | Vaccine 100 μL equivalent | Pimobendan | 100 | PDE inhibition | 30 |
| Ex. 657 | Sublingual | Solution | Inactivated Japanese encephalitis virus | Vaccine 100 μL equivalent | BRL50481 | 100 | PDE inhibition | 30 |
| Ex. 658 | Sublingual | Solution | Inactivated Japanese encephalitis virus | Vaccine 100 μL equivalent | Dipyridamole | 200 | PDE inhibition | 30 |
| Ex. 659 | Sublingual | Solution | Inactivated Japanese encephalitis virus | Vaccine 100 μL equivalent | Methoxyphenamine hydrochloride | 100 | β2 activation | 30 |
| Ex. 660 | Sublingual | Solution | Inactivated Japanese encephalitis virus | Vaccine 100 μL equivalent | Fenoldopam mesylate | 100 | D1 activation | 30 |
| Ex. 661 | Sublingual | Solution | Inactivated Japanese encephalitis virus | Vaccine 100 μL equivalent | Cisapride | 100 | 5-HT4 activation | 30 |
| Ex. 662 | Sublingual | Solution | Inactivated Japanese encephalitis virus | Vaccine 100 μL equivalent | Desmopressin | 100 | V2 activation | 30 |
| Ex. 663 | Sublingual | Solution | Inactivated Japanese encephalitis virus | Vaccine 100 μL equivalent | Prazosin hydrochloride | 400 | α1,2 antagonization | 30 |
| Ex. 664 | Sublingual | Solution | Inactivated Japanese encephalitis virus | Vaccine 100 μL equivalent | Pirenzepine hydrochloride | 100 | M1 antagonization | 30 |
| Ex. 665 | Sublingual | Solution | Inactivated Japanese encephalitis virus | Vaccine 100 μL equivalent | Oxybutynin hydrochloride | 200 | M2 antagonization | 30 |
| Ex. 666 | Sublingual | Solution | Inactivated Japanese encephalitis virus | Vaccine 100 μL equivalent | Tolterodine tartrate | 400 | M3 antagonization | 30 |
| Ex. 667 | Sublingual | Solution | Inactivated Japanese encephalitis virus | Vaccine 100 μL equivalent | Fluphenazine | 50 | D2 antagonization | 30 |
| Ex. 668 | Sublingual | Solution | Inactivated Japanese encephalitis virus | Vaccine 100 μL equivalent | Droperidol | 100 | | 30 |
| Ex. 669 | Sublingual | Solution | Inactivated Japanese encephalitis virus | Vaccine 100 μL equivalent | Sulpiride | 100 | | 30 |
| Ex. 670 | Sublingual | Solution | Inactivated Japanese encephalitis virus | Vaccine 100 μL equivalent | Azelastine hydrochloride | 200 | H1 antagonization | 30 |
| Ex. 671 | Sublingual | Solution | Inactivated Japanese encephalitis virus | Vaccine 100 μL equivalent | Levocetirizine | 100 | | 30 |
| Ex. 672 | Sublingual | Solution | Inactivated Japanese encephalitis virus | Vaccine 100 μL equivalent | Mequitazine | 100 | | 30 |
| Ex. 673 | Sublingual | Solution | Inactivated Japanese encephalitis virus | Vaccine 100 μL equivalent | Thioperamide | 100 | H3 antagonization | 30 |
| Ex. 674 | Sublingual | Solution | Inactivated Japanese encephalitis virus | Vaccine 100 μL equivalent | Sarpogrelate hydrochloride | 100 | 5-HT2 antagonization | 30 |
| Ex. 675 | Sublingual | Solution | Inactivated Japanese encephalitis virus | Vaccine 100 μL equivalent | Clopidogrel | 100 | P2Y12 antagonization | 30 |
| Ex. 676 | Sublingual | Solution | Inactivated Japanese encephalitis virus | Vaccine 100 μL equivalent | Ticlopidine | 200 | | 30 |
| Ex. 677 | Sublingual | Solution | Inactivated Japanese encephalitis virus | Vaccine 100 μL equivalent | Prasugrel | 100 | | 30 |
| Ex. 678 | Sublingual | Solution | Inactivated Japanese encephalitis virus | Vaccine 100 μL equivalent | Apafant | 100 | PAF antagonization | 30 |

TABLE 27-continued

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Ex. 679 | Sublingual | Solution | Inactivated Japanese encephalitis virus | Vaccine 100 μL equivalent | Naloxone | 100 | μ, κ, σ antagonization | 30 |
| Ex. 680 | Sublingual | Solution | Inactivated Japanese encephalitis virus | Vaccine 100 μL equivalent | Zafirlukast | 100 | CysLT antagonization | 30 |
| Ex. 681 | Sublingual | Solution | Inactivated Japanese encephalitis virus | Vaccine 100 μL equivalent | Montelukast | 100 | | 30 |
| Ex. 682 | Sublingual | Solution | Inactivated Japanese encephalitis virus | Vaccine 100 μL equivalent | Pranlukast | 100 | | 30 |
| Ex. 683 | Sublingual | Solution | Inactivated Japanese encephalitis virus | Vaccine 100 μL equivalent | Candesartan | 100 | AT1 antagonization | 30 |

TABLE 28

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 45 | Transnasal | Solution | Live attenuated mumps virus | Vaccine 100 μL equivalent | — | — | | 10 |
| Ex. 684 | Transnasal | Solution | Live attenuated mumps virus | Vaccine 100 μL equivalent | Resveratrol | 40 | PDE inhibition | 10 |
| Ex. 685 | Transnasal | Solution | Live attenuated mumps virus | Vaccine 100 μL equivalent | Vinpocetine | 20 | PDE inhibition | 10 |
| Ex. 686 | Transnasal | Solution | Live attenuated mumps virus | Vaccine 100 μL equivalent | Pimobendan | 20 | PDE inhibition | 10 |
| Ex. 687 | Transnasal | Solution | Live attenuated mumps virus | Vaccine 100 μL equivalent | BRL50481 | 20 | PDE inhibition | 10 |
| Ex. 688 | Transnasal | Solution | Live attenuated mumps virus | Vaccine 100 μL equivalent | Dipyridamole | 40 | PDE inhibition | 10 |
| Ex. 689 | Transnasal | Solution | Live attenuated mumps virus | Vaccine 100 μL equivalent | Methoxyphenamine hydrochloride | 20 | β2 activation | 10 |
| Ex. 690 | Transnasal | Solution | Live attenuated mumps virus | Vaccine 100 μL equivalent | Fenoldopam mesylate | 20 | D1 activation | 10 |
| Ex. 691 | Transnasal | Solution | Live attenuated mumps virus | Vaccine 100 μL equivalent | Cisapride | 20 | 5-HT4 activation | 10 |
| Ex. 692 | Transnasal | Solution | Live attenuated mumps virus | Vaccine 100 μL equivalent | Desmopressin | 20 | V2 activation | 10 |
| Ex. 693 | Transnasal | Solution | Live attenuated mumps virus | Vaccine 100 μL equivalent | Prazosin hydrochloride | 80 | α1,2 antagonization | 10 |
| Ex. 694 | Transnasal | Solution | Live attenuated mumps virus | Vaccine 100 μL equivalent | Pirenzepine hydrochloride | 20 | M1 antagonization | 10 |
| Ex. 695 | Transnasal | Solution | Live attenuated mumps virus | Vaccine 100 μL equivalent | Oxybutynin hydrochloride | 40 | M2 antagonization | 10 |
| Ex. 696 | Transnasal | Solution | Live attenuated mumps virus | Vaccine 100 μL equivalent | Tolterodine tartrate | 80 | M3 antagonization | 10 |
| Ex. 697 | Transnasal | Solution | Live attenuated mumps virus | Vaccine 100 μL equivalent | Fluphenazine | 10 | D2 antagonization | 10 |
| Ex. 698 | Transnasal | Solution | Live attenuated mumps virus | Vaccine 100 μL equivalent | Droperidol | 20 | | 10 |
| Ex. 699 | Transnasal | Solution | Live attenuated mumps virus | Vaccine 100 μL equivalent | Sulpiride | 20 | | 10 |
| Ex. 700 | Transnasal | Solution | Live attenuated mumps virus | Vaccine 100 μL equivalent | Azelastine hydrochloride | 40 | H1 antagonization | 10 |
| Ex. 701 | Transnasal | Solution | Live attenuated mumps virus | Vaccine 100 μL equivalent | Levocetirizine | 20 | | 10 |
| Ex. 702 | Transnasal | Solution | Live attenuated mumps virus | Vaccine 100 μL equivalent | Mequitazine | 20 | | 10 |
| Ex. 703 | Transnasal | Solution | Live attenuated mumps virus | Vaccine 100 μL equivalent | Thioperamide | 20 | H3 antagonization | 10 |
| Ex. 704 | Transnasal | Solution | Live attenuated mumps virus | Vaccine 100 μL equivalent | Sarpogrelate hydrochloride | 20 | 5-HT2 antagonization | 10 |
| Ex. 705 | Transnasal | Solution | Live attenuated mumps virus | Vaccine 100 μL equivalent | Clopidogrel | 20 | P2Y12 antagonization | 10 |
| Ex. 706 | Transnasal | Solution | Live attenuated mumps virus | Vaccine 100 μL equivalent | Ticlopidine | 40 | | 10 |
| Ex. 707 | Transnasal | Solution | Live attenuated mumps virus | Vaccine 100 μL equivalent | Prasugrel | 20 | | 10 |
| Ex. 708 | Transnasal | Solution | Live attenuated mumps virus | Vaccine 100 μL equivalent | Apafant | 20 | PAF antagonization | 10 |
| Ex. 709 | Transnasal | Solution | Live attenuated mumps virus | Vaccine 100 μL equivalent | Naloxone | 20 | μ, κ, σ antagonization | 10 |

TABLE 28-continued

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Ex. 710 | Transnasal | Solution | Live attenuated mumps virus | Vaccine 100 μL equivalent | Zafirlukast | 20 | CysLT antagonization | 10 |
| Ex. 711 | Transnasal | Solution | Live attenuated mumps virus | Vaccine 100 μL equivalent | Montelukast | 20 | | 10 |
| Ex. 712 | Transnasal | Solution | Live attenuated mumps virus | Vaccine 100 μL equivalent | Pranlukast | 20 | | 10 |
| Ex. 713 | Transnasal | Solution | Live attenuated mumps virus | Vaccine 100 μL equivalent | Candesartan | 20 | AT1 antagonization | 10 |

TABLE 29

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 46 | Sublingual | Solution | Live attenuated mumps virus | Vaccine 100 μL equivalent | — | — | | 30 |
| Ex. 714 | Sublingual | Solution | Live attenuated mumps virus | Vaccine 100 μL equivalent | Resveratrol | 200 | PDE inhibition | 30 |
| Ex. 715 | Sublingual | Solution | Live attenuated mumps virus | Vaccine 100 μL equivalent | Vinpocetine | 100 | PDE inhibition | 30 |
| Ex. 716 | Sublingual | Solution | Live attenuated mumps virus | Vaccine 100 μL equivalent | Pimobendan | 100 | PDE inhibition | 30 |
| Ex. 717 | Sublingual | Solution | Live attenuated mumps virus | Vaccine 100 μL equivalent | BRL50481 | 100 | PDE inhibition | 30 |
| Ex. 718 | Sublingual | Solution | Live attenuated mumps virus | Vaccine 100 μL equivalent | Dipyridamole | 200 | PDE inhibition | 30 |
| Ex. 719 | Sublingual | Solution | Live attenuated mumps virus | Vaccine 100 μL equivalent | Methoxyphenamine hydrochloride | 100 | β2 activation | 30 |
| Ex. 720 | Sublingual | Solution | Live attenuated mumps virus | Vaccine 100 μL equivalent | Fenoldopam mesylate | 100 | D1 activation | 30 |
| Ex. 721 | Sublingual | Solution | Live attenuated mumps virus | Vaccine 100 μL equivalent | Cisapride | 100 | 5-HT4 activation | 30 |
| Ex. 722 | Sublingual | Solution | Live attenuated mumps virus | Vaccine 100 μL equivalent | Desmopressin | 100 | V2 activation | 30 |
| Ex. 723 | Sublingual | Solution | Live attenuated mumps virus | Vaccine 100 μL equivalent | Prazosin hydrochloride | 400 | α1,2 antagonization | 30 |
| Ex. 724 | Sublingual | Solution | Live attenuated mumps virus | Vaccine 100 μL equivalent | Pirenzepine hydrochloride | 100 | M1 antagonization | 30 |
| Ex. 725 | Sublingual | Solution | Live attenuated mumps virus | Vaccine 100 μL equivalent | Oxybutynin hydrochloride | 200 | M2 antagonization | 30 |
| Ex. 726 | Sublingual | Solution | Live attenuated mumps virus | Vaccine 100 μL equivalent | Tolterodine tartrate | 400 | M3 antagonization | 30 |
| Ex. 727 | Sublingual | Solution | Live attenuated mumps virus | Vaccine 100 μL equivalent | Fluphenazine | 50 | D2 antagonization | 30 |
| Ex. 728 | Sublingual | Solution | Live attenuated mumps virus | Vaccine 100 μL equivalent | Droperidol | 100 | | 30 |
| Ex. 729 | Sublingual | Solution | Live attenuated mumps virus | Vaccine 100 μL equivalent | Sulpiride | 100 | | 30 |
| Ex. 730 | Sublingual | Solution | Live attenuated mumps virus | Vaccine 100 μL equivalent | Azelastine hydrochloride | 200 | H1 antagonization | 30 |
| Ex. 731 | Sublingual | Solution | Live attenuated mumps virus | Vaccine 100 μL equivalent | Levocetirizine | 100 | | 30 |
| Ex. 732 | Sublingual | Solution | Live attenuated mumps virus | Vaccine 100 μL equivalent | Mequitazine | 100 | | 30 |
| Ex. 733 | Sublingual | Solution | Live attenuated mumps virus | Vaccine 100 μL equivalent | Thioperamide | 100 | H3 antagonization | 30 |
| Ex. 734 | Sublingual | Solution | Live attenuated mumps virus | Vaccine 100 μL equivalent | Sarpogrelate hydrochloride | 100 | 5-HT2 antagonization | 30 |
| Ex. 735 | Sublingual | Solution | Live attenuated mumps virus | Vaccine 100 μL equivalent | Clopidogrel | 100 | P2Y12 antagonization | 30 |
| Ex. 736 | Sublingual | Solution | Live attenuated mumps virus | Vaccine 100 μL equivalent | Ticlopidine | 200 | | 30 |
| Ex. 737 | Sublingual | Solution | Live attenuated mumps virus | Vaccine 100 μL equivalent | Prasugrel | 100 | | 30 |
| Ex. 738 | Sublingual | Solution | Live attenuated mumps virus | Vaccine 100 μL equivalent | Apafant | 100 | PAF antagonization | 30 |
| Ex. 739 | Sublingual | Solution | Live attenuated mumps virus | Vaccine 100 μL equivalent | Naloxone | 100 | μ, κ, σ antagonization | 30 |
| Ex. 740 | Sublingual | Solution | Live attenuated mumps virus | Vaccine 100 μL equivalent | Zafirlukast | 100 | CysLT antagonization | 30 |

TABLE 29-continued

|  | Administration route | Dosage form | Antigen | | Th2 reaction promoter | | | Amount [μL] |
|---|---|---|---|---|---|---|---|---|
|  |  |  | Name | Amount [μg] | Name | Amount [μg] | Pharmacological effect |  |
| Ex. 741 | Sublingual | Solution | Live attenuated mumps virus | Vaccine 100 μL equivalent | Montelukast | 100 |  | 30 |
| Ex. 742 | Sublingual | Solution | Live attenuated mumps virus | Vaccine 100 μL equivalent | Pranlukast | 100 |  | 30 |
| Ex. 743 | Sublingual | Solution | Live attenuated mumps virus | Vaccine 100 μL equivalent | Candesartan | 100 | AT1 antagonization | 30 |

TABLE 30

|  | Administration route | Dosage form | Antigen | | Th2 reaction promoter | | | Amount [μL] |
|---|---|---|---|---|---|---|---|---|
|  |  |  | Name | Amount [μg] | Name | Amount [μg] | Pharmacological effect |  |
| Comp. Ex. 47 | Transnasal | Solution | Live attenuated measles virus | Vaccine 100 μL equivalent | — | — |  | 10 |
| Ex. 744 | Transnasal | Solution | Live attenuated measles virus | Vaccine 100 μL equivalent | Resveratrol | 40 | PDE inhibition | 10 |
| Ex. 745 | Transnasal | Solution | Live attenuated measles virus | Vaccine 100 μL equivalent | Vinpocetine | 20 | PDE inhibition | 10 |
| Ex. 746 | Transnasal | Solution | Live attenuated measles virus | Vaccine 100 μL equivalent | Pimobendan | 20 | PDE inhibition | 10 |
| Ex. 747 | Transnasal | Solution | Live attenuated measles virus | Vaccine 100 μL equivalent | BRL50481 | 20 | PDE inhibition | 10 |
| Ex. 748 | Transnasal | Solution | Live attenuated measles virus | Vaccine 100 μL equivalent | Dipyridamole | 40 | PDE inhibition | 10 |
| Ex. 749 | Transnasal | Solution | Live attenuated measles virus | Vaccine 100 μL equivalent | Methoxyphenamine hydrochloride | 20 | β2 activation | 10 |
| Ex. 750 | Transnasal | Solution | Live attenuated measles virus | Vaccine 100 μL equivalent | Fenoldopam mesylate | 20 | D1 activation | 10 |
| Ex. 751 | Transnasal | Solution | Live attenuated measles virus | Vaccine 100 μL equivalent | Cisapride | 20 | 5-HT4 activation | 10 |
| Ex. 752 | Transnasal | Solution | Live attenuated measles virus | Vaccine 100 μL equivalent | Desmopressin | 20 | V2 activation | 10 |
| Ex. 753 | Transnasal | Solution | Live attenuated measles virus | Vaccine 100 μL equivalent | Prazosin hydrochloride | 80 | α1,2 antagonization | 10 |
| Ex. 754 | Transnasal | Solution | Live attenuated measles virus | Vaccine 100 μL equivalent | Pirenzepine hydrochloride | 20 | M1 antagonization | 10 |
| Ex. 755 | Transnasal | Solution | Live attenuated measles virus | Vaccine 100 μL equivalent | Oxybutynin hydrochloride | 40 | M2 antagonization | 10 |
| Ex. 756 | Transnasal | Solution | Live attenuated measles virus | Vaccine 100 μL equivalent | Tolterodine tartrate | 80 | M3 antagonization | 10 |
| Ex. 757 | Transnasal | Solution | Live attenuated measles virus | Vaccine 100 μL equivalent | Fluphenazine | 10 | D2 antagonization | 10 |
| Ex. 758 | Transnasal | Solution | Live attenuated measles virus | Vaccine 100 μL equivalent | Droperidol | 20 |  | 10 |
|

TABLE 30-continued

|  | Administration route | Dosage form | Antigen Name | Amount [μg] | Th2 reaction promoter Name | Amount [μg] | Pharmacological effect | Amount [μL] |
|---|---|---|---|---|---|---|---|---|
| Ex. 772 | Transnasal | Solution | Live attenuated measles virus | Vaccine 100 μL equivalent | Pranlukast | 20 |  | 10 |
| Ex. 773 | Transnasal | Solution | Live attenuated measles virus | Vaccine 100 μL equivalent | Candesartan | 20 | AT1 antagonization | 10 |

TABLE 31

|  | Administration route | Dosage form | Antigen Name | Amount [μg] | Th2 reaction promoter Name | Amount [μg] | Pharmacological effect | Amount [μL] |
|---|---|---|---|---|---|---|---|---|
| Comp. Ex. 48 | Sublingual | Solution | Live attenuated measles virus | Vaccine 100 μL equivalent | — | — |  | 30 |
| Ex. 774 | Sublingual | Solution | Live attenuated measles virus | Vaccine 100 μL equivalent | Resveratrol | 200 | PDE inhibition | 30 |
| Ex. 775 | Sublingual | Solution | Live attenuated measles virus | Vaccine 100 μL equivalent | Vinpocetine | 100 | PDE inhibition | 30 |
| Ex. 776 | Sublingual | Solution | Live attenuated measles virus | Vaccine 100 μL equivalent | Pimobendan | 100 | PDE inhibition | 30 |
| Ex. 777 | Sublingual | Solution | Live attenuated measles virus | Vaccine 100 μL equivalent | BRL50481 | 100 | PDE inhibition | 30 |
| Ex. 778 | Sublingual | Solution | Live attenuated measles virus | Vaccine 100 μL equivalent | Dipyridamole | 200 | PDE inhibition | 30 |
| Ex. 779 | Sublingual | Solution | Live attenuated measles virus | Vaccine 100 μL equivalent | Methoxyphenamine hydrochloride | 100 | β2 activation | 30 |
| Ex. 780 | Sublingual | Solution | Live attenuated measles virus | Vaccine 100 μL equivalent | Fenoldopam mesylate | 100 | D1 activation | 30 |
| Ex. 781 | Sublingual | Solution | Live attenuated measles virus | Vaccine 100 μL equivalent | Cisapride | 100 | 5-HT4 activation | 30 |
| Ex. 782 | Sublingual | Solution | Live attenuated measles virus | Vaccine 100 μL equivalent | Desmopressin | 100 | V2 activation | 30 |
| Ex. 783 | Sublingual | Solution | Live attenuated measles virus | Vaccine 100 μL equivalent | Prazosin hydrochloride | 400 | α1,2 antagonization | 30 |
| Ex. 784 | Sublingual | Solution | Live attenuated measles virus | Vaccine 100 μL equivalent | Pirenzepine hydrochloride | 100 | M1 antagonization | 30 |
| Ex. 785 | Sublingual | Solution | Live attenuated measles virus | Vaccine 100 μL equivalent | Oxybutynin hydrochloride | 200 | M2 antagonization | 30 |
| Ex. 786 | Sublingual | Solution | Live attenuated measles virus | Vaccine 100 μL equivalent | Tolterodine tartrate | 400 | M3 antagonization | 30 |
| Ex. 787 | Sublingual | Solution | Live attenuated measles virus | Vaccine 100 μL equivalent | Fluphenazine | 50 | D2 antagonization | 30 |
| Ex. 788 | Sublingual | Solution | Live attenuated measles virus | Vaccine 100 μL equivalent | Droperidol | 100 |  | 30 |
| Ex. 789 | Sublingual | Solution | Live attenuated measles virus | Vaccine 100 μL equivalent | Sulpiride | 100 |  | 30 |
| Ex. 790 | Sublingual | Solution | Live attenuated measles virus | Vaccine 100 μL equivalent | Azelastine hydrochloride | 200 | H1 antagonization | 30 |
| Ex. 791 | Sublingual | Solution | Live attenuated measles virus | Vaccine 100 μL equivalent | Levocetirizine | 100 |  | 30 |
| Ex. 792 | Sublingual | Solution | Live attenuated measles virus | Vaccine 100 μL equivalent | Mequitazine | 100 |  | 30 |
| Ex. 793 | Sublingual | Solution | Live attenuated measles virus | Vaccine 100 μL equivalent | Thioperamide | 100 | H3 antagonization | 30 |
| Ex. 794 | Sublingual | Solution | Live attenuated measles virus | Vaccine 100 μL equivalent | Sarpogrelate hydrochloride | 100 | 5-HT2 antagonization | 30 |
| Ex. 795 | Sublingual | Solution | Live attenuated measles virus | Vaccine 100 μL equivalent | Clopidogrel | 100 | P2Y12 antagonization | 30 |
| Ex. 796 | Sublingual | Solution | Live attenuated measles virus | Vaccine 100 μL equivalent | Ticlopidine | 200 |  | 30 |
| Ex. 797 | Sublingual | Solution | Live attenuated measles virus | Vaccine 100 μL equivalent | Prasugrel | 100 |  | 30 |
| Ex. 798 | Sublingual | Solution | Live attenuated measles virus | Vaccine 100 μL equivalent | Apafant | 100 | PAF antagonization | 30 |
| Ex. 799 | Sublingual | Solution | Live attenuated measles virus | Vaccine 100 μL equivalent | Naloxone | 100 | μ, κ, σ antagonization | 30 |
| Ex. 800 | Sublingual | Solution | Live attenuated measles virus | Vaccine 100 μL equivalent | Zafirlukast | 100 | CysLT antagonization | 30 |
| Ex. 801 | Sublingual | Solution | Live attenuated measles virus | Vaccine 100 μL equivalent | Montelukast | 100 |  | 30 |
| Ex. 802 | Sublingual | Solution | Live attenuated measles virus | Vaccine 100 μL equivalent | Pranlukast | 100 |  | 30 |

TABLE 31-continued

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Ex. 803 | Sublingual | Solution | Live attenuated measles virus | Vaccine 100 μL equivalent | Candesartan | 100 | AT1 antagonization | 30 |

TABLE 32

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 49 | Trasnasal | Solution | Live attenuated rubella virus | Vaccine 100 μL equivalent | — | — | | 10 |
| Ex. 804 | Trasnasal | Solution | Live attenuated rubella virus | Vaccine 100 μL equivalent | Resveratrol | 40 | PDE inhibition | 10 |
| Ex. 805 | Trasnasal | Solution | Live attenuated rubella virus | Vaccine 100 μL equivalent | Vinpocetine | 20 | PDE inhibition | 10 |
| Ex. 806 | Trasnasal | Solution | Live attenuated rubella virus | Vaccine 100 μL equivalent | Pimobendan | 20 | PDE inhibition | 10 |
| Ex. 807 | Trasnasal | Solution | Live attenuated rubella virus | Vaccine 100 μL equivalent | BRL50481 | 20 | PDE inhibition | 10 |
| Ex. 808 | Trasnasal | Solution | Live attenuated rubella virus | Vaccine 100 μL equivalent | Dipyridamole | 40 | PDE inhibition | 10 |
| Ex. 809 | Trasnasal | Solution | Live attenuated rubella virus | Vaccine 100 μL equivalent | Methoxyphenamine hydrochloride | 20 | β2 activation | 10 |
| Ex. 810 | Trasnasal | Solution | Live attenuated rubella virus | Vaccine 100 μL equivalent | Fenoldopam mesylate | 20 | D1 activation | 10 |
| Ex. 811 | Trasnasal | Solution | Live attenuated rubella virus | Vaccine 100 μL equivalent | Cisapride | 20 | 5-HT4 activation | 10 |
| Ex. 812 | Trasnasal | Solution | Live attenuated rubella virus | Vaccine 100 μL equivalent | Desmopressin | 20 | V2 activation | 10 |
| Ex. 813 | Trasnasal | Solution | Live attenuated rubella virus | Vaccine 100 μL equivalent | Prazosin hydrochloride | 80 | α1,2 antagonization | 10 |
| Ex. 814 | Trasnasal | Solution | Live attenuated rubella virus | Vaccine 100 μL equivalent | Pirenzepine hydrochloride | 20 | M1 antagonization | 10 |
| Ex. 815 | Trasnasal | Solution | Live attenuated rubella virus | Vaccine 100 μL equivalent | Oxybutynin hydrochloride | 40 | M2 antagonization | 10 |
| Ex. 816 | Trasnasal | Solution | Live attenuated rubella virus | Vaccine 100 μL equivalent | Tolterodine tartrate | 80 | M3 antagonization | 10 |
| Ex. 817 | Trasnasal | Solution | Live attenuated rubella virus | Vaccine 100 μL equivalent | Fluphenazine | 10 | D2 antagonization | 10 |
| Ex. 818 | Trasnasal | Solution | Live attenuated rubella virus | Vaccine 100 μL equivalent | Droperidol | 20 | | 10 |
| Ex. 819 | Trasnasal | Solution | Live attenuated rubella virus | Vaccine 100 μL equivalent | Sulpiride | 20 | | 10 |
| Ex. 820 | Trasnasal | Solution | Live attenuated rubella virus | Vaccine 100 μL equivalent | Azelastine hydrochloride | 40 | H1 antagonization | 10 |
| Ex. 821 | Trasnasal | Solution | Live attenuated rubella virus | Vaccine 100 μL equivalent | Levocetirizine | 20 | | 10 |
| Ex. 822 | Trasnasal | Solution | Live attenuated rubella virus | Vaccine 100 μL equivalent | Mequitazine | 20 | | 10 |
| Ex. 823 | Trasnasal | Solution | Live attenuated rubella virus | Vaccine 100 μL equivalent | Thioperamide | 20 | H3 antagonization | 10 |
| Ex. 824 | Trasnasal | Solution | Live attenuated rubella virus | Vaccine 100 μL equivalent | Sarpogrelate hydrochloride | 20 | 5-HT2 antagonization | 10 |
| Ex. 825 | Trasnasal | Solution | Live attenuated rubella virus | Vaccine 100 μL equivalent | Clopidogrel | 20 | P2Y12 antagonization | 10 |
| Ex. 826 | Trasnasal | Solution | Live attenuated rubella virus | Vaccine 100 μL equivalent | Ticlopidine | 40 | | 10 |
| Ex. 827 | Trasnasal | Solution | Live attenuated rubella virus | Vaccine 100 μL equivalent | Prasugrel | 20 | | 10 |
| Ex. 828 | Trasnasal | Solution | Live attenuated rubella virus | Vaccine 100 μL equivalent | Apafant | 20 | PAF antagonization | 10 |
| Ex. 829 | Trasnasal | Solution | Live attenuated rubella virus | Vaccine 100 μL equivalent | Naloxone | 20 | μ, κ, σ antagonization | 10 |
| Ex. 830 | Trasnasal | Solution | Live attenuated rubella virus | Vaccine 100 μL equivalent | Zafirlukast | 20 | CysLT antagonization | 10 |
| Ex. 831 | Trasnasal | Solution | Live attenuated rubella virus | Vaccine 100 μL equivalent | Montelukast | 20 | | 10 |

TABLE 32-continued

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Ex. 832 | Trasnasal | Solution | Live attenuated rubella virus | Vaccine 100 μL equivalent | Pranlukast | 20 | | 10 |
| Ex. 833 | Trasnasal | Solution | Live attenuated rubella virus | Vaccine 100 μL equivalent | Candesartan | 20 | AT1 antagonization | 10 |

TABLE 33

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 50 | Sublingual | Solution | Live attenuated rubella virus | Vaccine 100 μL equivalent | — | — | | 30 |
| Ex. 834 | Sublingual | Solution | Live attenuated rubella virus | Vaccine 100 μL equivalent | Resveratrol | 200 | PDE inhibition | 30 |
| Ex. 835 | Sublingual | Solution | Live attenuated rubella virus | Vaccine 100 μL equivalent | Vinpocetine | 100 | PDE inhibition | 30 |
| Ex. 836 | Sublingual | Solution | Live attenuated rubella virus | Vaccine 100 μL equivalent | Pimobendan | 100 | PDE inhibition | 30 |
| Ex. 837 | Sublingual | Solution | Live attenuated rubella virus | Vaccine 100 μL equivalent | BRL50481 | 100 | PDE inhibition | 30 |
| Ex. 838 | Sublingual | Solution | Live attenuated rubella virus | Vaccine 100 μL equivalent | Dipyridamole | 200 | PDE inhibition | 30 |
| Ex. 839 | Sublingual | Solution | Live attenuated rubella virus | Vaccine 100 μL equivalent | Methoxyphenamine hydrochloride | 100 | β2 activation | 30 |
| Ex. 840 | Sublingual | Solution | Live attenuated rubella virus | Vaccine 100 μL equivalent | Fenoldopam mesylate | 100 | D1 activation | 30 |
| Ex. 841 | Sublingual | Solution | Live attenuated rubella virus | Vaccine 100 μL equivalent | Cisapride | 100 | 5-HT4 activation | 30 |
| Ex. 842 | Sublingual | Solution | Live attenuated rubella virus | Vaccine 100 μL equivalent | Desmopressin | 100 | V2 activation | 30 |
| Ex. 843 | Sublingual | Solution | Live attenuated rubella virus | Vaccine 100 μL equivalent | Prazosin hydrochloride | 400 | α1,2 antagonization | 30 |
| Ex. 844 | Sublingual | Solution | Live attenuated rubella virus | Vaccine 100 μL equivalent | Pirenzepine hydrochloride | 100 | M1 antagonization | 30 |
| Ex. 845 | Sublingual | Solution | Live attenuated rubella virus | Vaccine 100 μL equivalent | Oxybutynin hydrochloride | 200 | M2 antagonization | 30 |
| Ex. 846 | Sublingual | Solution | Live attenuated rubella virus | Vaccine 100 μL equivalent | Tolterodine tartrate | 400 | M3 antagonization | 30 |
| Ex. 847 | Sublingual | Solution | Live attenuated rubella virus | Vaccine 100 μL equivalent | Fluphenazine | 50 | D2 antagonization | 30 |
| Ex. 848 | Sublingual | Solution | Live attenuated rubella virus | Vaccine 100 μL equivalent | Droperidol | 100 | | 30 |
| Ex. 849 | Sublingual | Solution | Live attenuated rubella virus | Vaccine 100 μL equivalent | Sulpiride | 100 | | 30 |
| Ex. 850 | Sublingual | Solution | Live attenuated rubella virus | Vaccine 100 μL equivalent | Azelastine hydrochloride | 200 | H1 antagonization | 30 |
| Ex. 851 | Sublingual | Solution | Live attenuated rubella virus | Vaccine 100 μL equivalent | Levocetirizine | 100 | | 30 |
| Ex. 852 | Sublingual | Solution | Live attenuated rubella virus | Vaccine 100 μL equivalent | Mequitazine | 100 | | 30 |
| Ex. 853 | Sublingual | Solution | Live attenuated rubella virus | Vaccine 100 μL equivalent | Thioperamide | 100 | H3 antagonization | 30 |
| Ex. 854 | Sublingual | Solution | Live attenuated rubella virus | Vaccine 100 μL equivalent | Sarpogrelate hydrochloride | 100 | 5-HT2 antagonization | 30 |
| Ex. 855 | Sublingual | Solution | Live attenuated rubella virus | Vaccine 100 μL equivalent | Clopidogrel | 100 | P2Y12 antagonization | 30 |
| Ex. 856 | Sublingual | Solution | Live attenuated rubella virus | Vaccine 100 μL equivalent | Ticlopidine | 200 | | 30 |
| Ex. 857 | Sublingual | Solution | Live attenuated rubella virus | Vaccine 100 μL equivalent | Prasugrel | 100 | | 30 |
| Ex. 858 | Sublingual | Solution | Live attenuated rubella virus | Vaccine 100 μL equivalent | Apafant | 100 | PAF antagonization | 30 |
| Ex. 859 | Sublingual | Solution | Live attenuated rubella virus | Vaccine 100 μL equivalent | Naloxone | 100 | μ, κ, σ antagonization | 30 |
| Ex. 860 | Sublingual | Solution | Live attenuated rubella virus | Vaccine 100 μL equivalent | Zafirlukast | 100 | CysLT antagonization | 30 |
| Ex. 861 | Sublingual | Solution | Live attenuated rubella virus | Vaccine 100 μL equivalent | Montelukast | 100 | | 30 |
| Ex. 862 | Sublingual | Solution | Live attenuated rubella virus | Vaccine 100 μL equivalent | Pranlukast | 100 | | 30 |

TABLE 33-continued

| | Administration route | Dosage form | Antigen Name | Amount [μg] | Th2 reaction promoter Name | Amount [μg] | Pharmacological effect | Amount [μL] |
|---|---|---|---|---|---|---|---|---|
| Ex. 863 | Sublingual | Solution | Live attenuated rubella virus | Vaccine 100 μL equivalent | Candesartan | 100 | AT1 antagonization | 30 |

TABLE 34

| | Administration route | Dosage form | Antigen Name | Amount [μg] | Th2 reaction promoter Name | Amount [μg] | Pharmacological effect | Amount [μL] |
|---|---|---|---|---|---|---|---|---|
| Comp. Ex. 51 | Transnasal | Solution | *Haemophilus influenzae* type b polysaccharide-tetanus toxoid conjugate | Vaccine 100 μL equivalent | — | — | | 10 |
| Ex. 864 | Transnasal | Solution | *Haemophilus influenzae* type b polysaccharide-tetanus toxoid conjugate | Vaccine 100 μL equivalent | Resveratrol | 40 | PDE inhibition | 10 |
| Ex. 865 | Transnasal | Solution | *Haemophilus influenzae* type b polysaccharide-tetanus toxoid conjugate | Vaccine 100 μL equivalent | Vinpocetine | 20 | PDE inhibition | 10 |
| Ex. 866 | Transnasal | Solution | *Haemophilus influenzae* type b polysaccharide-tetanus toxoid conjugate | Vaccine 100 μL equivalent | Pimobendan | 20 | PDE inhibition | 10 |
| Ex. 867 | Transnasal | Solution | *Haemophilus influenzae* type b polysaccharide-tetanus toxoid conjugate | Vaccine 100 μL equivalent | BRL50481 | 20 | PDE inhibition | 10 |
| Ex. 868 | Transnasal | Solution | *Haemophilus influenzae* type b polysaccharide-tetanus toxoid conjugate | Vaccine 100 μL equivalent | Dipyridamole | 40 | PDE inhibition | 10 |
| Ex. 869 | Transnasal | Solution | *Haemophilus influenzae* type b polysaccharide-tetanus toxoid conjugate | Vaccine 100 μL equivalent | Methoxyphenamine hydrochloride | 20 | β2 activation | 10 |
| Ex. 870 | Transnasal | Solution | *Haemophilus influenzae* type b polysaccharide-tetanus toxoid conjugate | Vaccine 100 μL equivalent | Fenoldopam mesylate | 20 | D1 activation | 10 |
| Ex. 871 | Transnasal | Solution | *Haemophilus influenzae* type b polysaccharide-tetanus toxoid conjugate | Vaccine 100 μL equivalent | Cisapride | 20 | 5-HT4 activation | 10 |
| Ex. 872 | Transnasal | Solution | *Haemophilus influenzae* type b polysaccharide-tetanus toxoid conjugate | Vaccine 100 μL equivalent | Desmopressin | 20 | V2 activation | 10 |
| Ex. 873 | Transnasal | Solution | *Haemophilus influenzae* type b polysaccharide-tetanus toxoid conjugate | Vaccine 100 μL equivalent | Prazosin hydrochloride | 80 | α1,2 antagonization | 10 |
| Ex. 874 | Transnasal | Solution | *Haemophilus influenzae* type b polysaccharide-tetanus toxoid conjugate | Vaccine 100 μL equivalent | Pirenzepine hydrochloride | 20 | M1 antagonization | 10 |
| Ex. 875 | Transnasal | Solution | *Haemophilus influenzae* type b polysaccharide-tetanus toxoid conjugate | Vaccine 100 μL equivalent | Oxybutynin hydrochloride | 40 | M2 antagonization | 10 |
| Ex. 876 | Transnasal | Solution | *Haemophilus influenzae* type b polysaccharide-tetanus toxoid conjugate | Vaccine 100 μL equivalent | Tolterodine tartrate | 80 | M3 antagonization | 10 |
| Ex. 877 | Transnasal | Solution | *Haemophilus influenzae* type b polysaccharide-tetanus toxoid conjugate | Vaccine 100 μL equivalent | Fluphenazine | 10 | D2 antagonization | 10 |
| Ex. 878 | Transnasal | Solution | *Haemophilus influenzae* type b polysaccharide-tetanus toxoid conjugate | Vaccine 100 μL equivalent | Droperidol | 20 | | 10 |
| Ex. 879 | Transnasal | Solution | *Haemophilus influenzae* type b polysaccharide-tetanus toxoid conjugate | Vaccine 100 μL equivalent | Sulpiride | 20 | | 10 |
| Ex. 880 | Transnasal | Solution | *Haemophilus influenzae* type b polysaccharide-tetanus toxoid conjugate | Vaccine 100 μL equivalent | Azelastine hydrochloride | 40 | H1 antagonization | 10 |
| Ex. 881 | Transnasal | Solution | *Haemophilus influenzae* type b polysaccharide-tetanus toxoid conjugate | Vaccine 100 μL equivalent | Levocetirizine | 20 | | 10 |
| Ex. 882 | Transnasal | Solution | *Haemophilus influenzae* type b polysaccharide-tetanus toxoid conjugate | Vaccine 100 μL equivalent | Mequitazine | 20 | | 10 |

TABLE 34-continued

| | | | Antigen | | Th2 reaction promoter | | | |
|---|---|---|---|---|---|---|---|---|
| | Administration route | Dosage form | Name | Amount [μg] | Name | Amount [μg] | Pharmacological effect | Amount [μL] |
| Ex. 883 | Transnasal | Solution | Haemophilus influenzae type b polysaccharide-tetanus toxoid conjugate | Vaccine 100 μL equivalent | Thioperamide | 20 | H3 antagonization | 10 |
| Ex. 884 | Transnasal | Solution | Haemophilus influenzae type b polysaccharide-tetanus toxoid conjugate | Vaccine 100 μL equivalent | Sarpogrelate hydrochloride | 20 | 5-HT2 antagonization | 10 |
| Ex. 885 | Transnasal | Solution | Haemophilus influenzae type b polysaccharide-tetanus toxoid conjugate | Vaccine 100 μL equivalent | Clopidogrel | 20 | P2Y12 antagonization | 10 |
| Ex. 886 | Transnasal | Solution | Haemophilus influenzae type b polysaccharide-tetanus toxoid conjugate | Vaccine 100 μL equivalent | Ticlopidine | 40 | | 10 |
| Ex. 887 | Transnasal | Solution | Haemophilus influenzae type b polysaccharide-tetanus toxoid conjugate | Vaccine 100 μL equivalent | Prasugrel | 20 | | 10 |
| Ex. 888 | Transnasal | Solution | Haemophilus influenzae type b polysaccharide-tetanus toxoid conjugate | Vaccine 100 μL equivalent | Apafant | 20 | PAF antagonization | 10 |
| Ex. 889 | Transnasal | Solution | Haemophilus influenzae type b polysaccharide-tetanus toxoid conjugate | Vaccine 100 μL equivalent | Naloxone | 20 | μ, κ, σ antagonization | 10 |
| Ex. 890 | Transnasal | Solution | Haemophilus influenzae type b polysaccharide-tetanus toxoid conjugate | Vaccine 100 μL equivalent | Zafirlukast | 20 | CysLT antagonization | 10 |
| Ex. 891 | Transnasal | Solution | Haemophilus influenzae type b polysaccharide-tetanus toxoid conjugate | Vaccine 100 μL equivalent | Montelukast | 20 | | 10 |
| Ex. 892 | Transnasal | Solution | Haemophilus influenzae type b polysaccharide-tetanus toxoid conjugate | Vaccine 100 μL equivalent | Pranlukast | 20 | | 10 |
| Ex. 893 | Transnasal | Solution | Haemophilus influenzae type b polysaccharide-tetanus toxoid conjugate | Vaccine 100 μL equivalent | Candesartan | 20 | AT1 antagonization | 10 |

TABLE 35

| | | | Antigen | | Th2 reaction promoter | | | |
|---|---|---|---|---|---|---|---|---|
| | Administration route | Dosage form | Name | Amount [μg] | Name | Amount [μg] | Pharmacological effect | Amount [μL] |
| Comp. Ex. 52 | Sublingual | Solution | Haemophilus influenzae type b polysaccharide-tetanus toxoid conjugate | Vaccine 100 μL equivalent | — | — | | 30 |
| Ex. 894 | Sublingual | Solution | Haemophilus influenzae type b polysaccharide-tetanus toxoid conjugate | Vaccine 100 μL equivalent | Resveratrol | 200 | PDE inhibition | 30 |
| Ex. 895 | Sublingual | Solution | Haemophilus influenzae type b polysaccharide-tetanus toxoid conjugate | Vaccine 100 μL equivalent | Vinpocetine | 100 | PDE inhibition | 30 |
| Ex. 896 | Sublingual | Solution | Haemophilus influenzae type b polysaccharide-tetanus toxoid conjugate | Vaccine 100 μL equivalent | Pimobendan | 100 | PDE inhibition | 30 |
| Ex. 897 | Sublingual | Solution | Haemophilus influenzae type b polysaccharide-tetanus toxoid conjugate | Vaccine 100 μL equivalent | BRL50481 | 100 | PDE inhibition | 30 |
| Ex. 898 | Sublingual | Solution | Haemophilus influenzae type b polysaccharide-tetanus toxoid conjugate | Vaccine 100 μL equivalent | Dipyridamole | 200 | PDE inhibition | 30 |
| Ex. 899 | Sublingual | Solution | Haemophilus influenzae type b polysaccharide-tetanus toxoid conjugate | Vaccine 100 μL equivalent | Methoxyphenamine hydrochloride | 100 | β2 activation | 30 |
| Ex. 900 | Sublingual | Solution | Haemophilus influenzae type b polysaccharide-tetanus toxoid conjugate | Vaccine 100 μL equivalent | Fenoldopam mesylate | 100 | D1 activation | 30 |
| Ex. 901 | Sublingual | Solution | Haemophilus influenzae type b polysaccharide-tetanus toxoid conjugate | Vaccine 100 μL equivalent | Cisapride | 100 | 5-HT4 activation | 30 |

TABLE 35-continued

| | Administration route | Dosage form | Antigen Name | Amount [µg] | Th2 reaction promoter Name | Amount [µg] | Pharmacological effect | Amount [µL] |
|---|---|---|---|---|---|---|---|---|
| Ex. 902 | Sublingual | Solution | *Haemophilus influenzae* type b polysaccharide-tetanus toxoid conjugate | Vaccine 100 µL equivalent | Desmopressin | 100 | V2 activation | 30 |
| Ex. 903 | Sublingual | Solution | *Haemophilus influenzae* type b polysaccharide-tetanus toxoid conjugate | Vaccine 100 µL equivalent | Prazosin hydrochloride | 400 | α1,2 antagonization | 30 |
| Ex. 904 | Sublingual | Solution | *Haemophilus influenzae* type b polysaccharide-tetanus toxoid conjugate | Vaccine 100 µL equivalent | Pirenzepine hycrochloride | 100 | M1 antagonization | 30 |
| Ex. 905 | Sublingual | Solution | *Haemophilus influenzae* type b polysaccharide-tetanus toxoid conjugate | Vaccine 100 µL equivalent | Oxybutynin hydrochloride | 200 | M2 antagonization | 30 |
| Ex. 906 | Sublingual | Solution | *Haemophilus influenzae* type b polysaccharide-tetanus toxoid conjugate | Vaccine 100 µL equivalent | Tolterodine tartrate | 400 | M3 antagonization | 30 |
| Ex. 907 | Sublingual | Solution | *Haemophilus influenzae* type b polysaccharide-tetanus toxoid conjugate | Vaccine 100 µL equivalent | Fluphenazine | 50 | D2 antagonization | 30 |
| Ex. 908 | Sublingual | Solution | *Haemophilus influenzae* type b polysaccharide-tetanus toxoid conjugate | Vaccine 100 µL equivalent | Droperidol | 100 | | 30 |
| Ex. 909 | Sublingual | Solution | *Haemophilus influenzae* type b polysaccharide-tetanus toxoid conjugate | Vaccine 100 µL equivalent | Sulpiride | 100 | | 30 |
| Ex. 910 | Sublingual | Solution | *Haemophilus influenzae* type b polysaccharide-tetanus toxoid conjugate | Vaccine 100 µL equivalent | Azelastine hydrochloride | 200 | H1 antagonization | 30 |
| Ex. 911 | Sublingual | Solution | *Haemophilus influenzae* type b polysaccharide-tetanus toxoid conjugate | Vaccine 100 µL equivalent | Levocetirizine | 100 | | 30 |
| Ex. 912 | Sublingual | Solution | *Haemophilus influenzae* type b polysaccharide-tetanus toxoid conjugate | Vaccine 100 µL equivalent | Mequitazine | 100 | | 30 |
| Ex. 913 | Sublingual | Solution | *Haemophilus influenzae* type b polysaccharide-tetanus toxoid conjugate | Vaccine 100 µL equivalent | Thioperamide | 100 | H3 antagonization | 30 |
| Ex. 914 | Sublingual | Solution | *Haemophilus influenzae* type b polysaccharide-tetanus toxoid conjugate | Vaccine 100 µL equivalent | Sarpogrelate hydrochloride | 100 | 5-HT2 antagonization | 30 |
| Ex. 915 | Sublingual | Solution | *Haemophilus influenzae* type b polysaccharide-tetanus toxoid conjugate | Vaccine 100 µL equivalent | Clopidogrel | 100 | P2Y12 antagonization | 30 |
| Ex. 916 | Sublingual | Solution | *Haemophilus influenzae* type b polysaccharide-tetanus toxoid conjugate | Vaccine 100 µL equivalent | Tiolopidine | 200 | | 30 |
| Ex. 917 | Sublingual | Solution | *Haemophilus influenzae* type b polysaccharide-tetanus toxoid conjugate | Vaccine 100 µL equivalent | Prasugrel | 100 | | 30 |
| Ex. 918 | Sublingual | Solution | *Haemophilus influenzae* type b polysaccharide-tetanus toxoid conjugate | Vaccine 100 µL equivalent | Apafant | 100 | PAF antagonization | 30 |
| Ex. 919 | Sublingual | Solution | *Haemophilus influenzae* type b polysaccharide-tetanus toxoid conjugate | Vaccine 100 µL equivalent | Naloxone | 100 | µ, κ, σ antagonization | 30 |
| Ex. 920 | Sublingual | Solution | *Haemophilus influenzae* type b polysaccharide-tetanus toxoid conjugate | Vaccine 100 µL equivalent | Zafirlukast | 100 | CysLT antagonization | 30 |
| Ex. 921 | Sublingual | Solution | *Haemophilus influenzae* type b polysaccharide-tetanus toxoid conjugate | Vaccine 100 µL equivalent | Montelukast | 100 | | 30 |
| Ex. 922 | Sublingual | Solution | *Haemophilus influenzae* type b polysaccharide-tetanus toxoid conjugate | Vaccine 100 µL equivalent | Pranlukast | 100 | | 30 |
| Ex. 923 | Sublingual | Solution | *Haemophilus influenzae* type b polysaccharide-tetanus toxoid conjugate | Vaccine 100 µL equivalent | Candesartan | 100 | AT1 antagonization | 30 |

TABLE 36

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 53 | Transnasal | Solution | Recombinant HBs antigen protein | Vaccine 100 μL equivalent | — | — | | 10 |
| Ex. 924 | Transnasal | Solution | Recombinant HBs antigen protein | Vaccine 100 μL equivalent | Resveratrol | 40 | PDE inhibition | 10 |
| Ex. 925 | Transnasal | Solution | Recombinant HBs antigen protein | Vaccine 100 μL equivalent | Vinpocetine | 20 | PDE inhibition | 10 |
| Ex. 926 | Transnasal | Solution | Recombinant HBs antigen protein | Vaccine 100 μL equivalent | Pimobendan | 20 | PDE inhibition | 10 |
| Ex. 927 | Transnasal | Solution | Recombinant HBs antigen protein | Vaccine 100 μL equivalent | BRL50481 | 20 | PDE inhibition | 10 |
| Ex. 928 | Transnasal | Solution | Recombinant HBs antigen protein | Vaccine 100 μL equivalent | Dipyridamole | 40 | PDE inhibition | 10 |
| Ex. 929 | Transnasal | Solution | Recombinant HBs antigen protein | Vaccine 100 μL equivalent | Methoxyphenamine hydrochloride | 20 | β2 activation | 10 |
| Ex. 930 | Transnasal | Solution | Recombinant HBs antigen protein | Vaccine 100 μL equivalent | Fenoldopam mesylate | 20 | D1 activation | 10 |
| Ex. 931 | Transnasal | Solution | Recombinant HBs antigen protein | Vaccine 100 μL equivalent | Cisapride | 20 | 5-HT4 activation | 10 |
| Ex. 932 | Transnasal | Solution | Recombinant HBs antigen protein | Vaccine 100 μL equivalent | Desmopressin | 20 | V2 activation | 10 |
| Ex. 933 | Transnasal | Solution | Recombinant HBs antigen protein | Vaccine 100 μL equivalent | Prazosin hydrochloride | 80 | α1,2 antagonization | 10 |
| Ex. 934 | Transnasal | Solution | Recombinant HBs antigen protein | Vaccine 100 μL equivalent | Pirenzepine hycrochloride | 20 | M1 antagonization | 10 |
| Ex. 935 | Transnasal | Solution | Recombinant HBs antigen protein | Vaccine 100 μL equivalent | Oxybutynin hydrochloride | 40 | M2 antagonization | 10 |
| Ex. 936 | Transnasal | Solution | Recombinant HBs antigen protein | Vaccine 100 μL equivalent | Tolterodine tartrate | 80 | M3 antagonization | 10 |
| Ex. 937 | Transnasal | Solution | Recombinant HBs antigen protein | Vaccine 100 μL equivalent | Fluphenazine | 10 | D2 antagonization | 10 |
| Ex. 938 | Transnasal | Solution | Recombinant HBs antigen protein | Vaccine 100 μL equivalent | Droperidol | 20 | | 10 |
| Ex. 939 | Transnasal | Solution | Recombinant HBs antigen protein | Vaccine 100 μL equivalent | Sulpiride | 20 | | 10 |
| Ex. 940 | Transnasal | Solution | Recombinant HBs antigen protein | Vaccine 100 μL equivalent | Azelastine hydrochloride | 40 | H1 antagonization | 10 |
| Ex. 941 | Transnasal | Solution | Recombinant HBs antigen protein | Vaccine 100 μL equivalent | Levocetirizine | 20 | | 10 |
| Ex. 942 | Transnasal | Solution | Recombinant HBs antigen protein | Vaccine 100 μL equivalent | Mequitazine | 20 | | 10 |
| Ex. 943 | Transnasal | Solution | Recombinant HBs antigen protein | Vaccine 100 μL equivalent | Thioperamide | 20 | H3 antagonization | 10 |
| Ex. 944 | Transnasal | Solution | Recombinant HBs antigen protein | Vaccine 100 μL equivalent | Sarpogrelate hydrochloride | 20 | 5-HT2 antagonization | 10 |
| Ex. 945 | Transnasal | Solution | Recombinant HBs antigen protein | Vaccine 100 μL equivalent | Clopidogrel | 20 | P2Y12 antagonization | 10 |
| Ex. 946 | Transnasal | Solution | Recombinant HBs antigen protein | Vaccine 100 μL equivalent | Tiolopidine | 40 | | 10 |
| Ex. 947 | Transnasal | Solution | Recombinant HBs antigen protein | Vaccine 100 μL equivalent | Prasugrel | 20 | | 10 |
| Ex. 948 | Transnasal | Solution | Recombinant HBs antigen protein | Vaccine 100 μL equivalent | Apafant | 20 | PAF antagonization | 10 |
| Ex. 949 | Transnasal | Solution | Recombinant HBs antigen protein | Vaccine 100 μL equivalent | Naloxone | 20 | μ, κ, σ antagonization | 10 |
| Ex. 950 | Transnasal | Solution | Recombinant HBs antigen protein | Vaccine 100 μL equivalent | Zafirlukast | 20 | CysLT antagonization | 10 |
| Ex. 951 | Transnasal | Solution | Recombinant HBs antigen protein | Vaccine 100 μL equivalent | Montelukast | 20 | | 10 |
| Ex. 952 | Transnasal | Solution | Recombinant HBs antigen protein | Vaccine 100 μL equivalent | Pranlukast | 20 | | 10 |
| Ex. 953 | Transnasal | Solution | Recombinant HBs antigen protein | Vaccine 100 μL equivalent | Candesartan | 20 | AT1 antagonization | 10 |

TABLE 37

| | Administration route | Dosage form | Antigen Name | Antigen Amount [μg] | TH2 reaction promoter Name | TH2 reaction promoter Amount [μg] | Pharmacological effect | Amount [μL] |
|---|---|---|---|---|---|---|---|---|
| Comp. Ex. 54 | Sublingual | Solution | Recombinant HBs antigen protein | Vaccine 100 μL equivalent | — | — | | 30 |

TABLE 37-continued

| | Administration route | Dosage form | Antigen Name | Amount [µg] | TH2 reaction promoter Name | Amount [µg] | Pharmacological effect | Amount [µL] |
|---|---|---|---|---|---|---|---|---|
| Ex. 954 | Sublingual | Solution | Recombinant HBs antigen protein | Vaccine 100 µL equivalent | Resveratrol | 200 | PDE inhibition | 30 |
| Ex. 955 | Sublingual | Solution | Recombinant HBs antigen protein | Vaccine 100 µL equivalent | Vinpocetine | 100 | PDE inhibition | 30 |
| Ex. 956 | Sublingual | Solution | Recombinant HBs antigen protein | Vaccine 100 µL equivalent | Pimobendan | 100 | PDE inhibition | 30 |
| Ex. 957 | Sublingual | Solution | Recombinant HBs antigen protein | Vaccine 100 µL equivalent | BRL50481 | 100 | PDE inhibition | 30 |
| Ex. 958 | Sublingual | Solution | Recombinant HBs antigen protein | Vaccine 100 µL equivalent | Dipyridamole | 200 | PDE inhibition | 30 |
| Ex. 959 | Sublingual | Solution | Recombinant HBs antigen protein | Vaccine 100 µL equivalent | Methoxyphenamine hydrochloride | 100 | β2 activation | 30 |
| Ex. 960 | Sublingual | Solution | Recombinant HBs antigen protein | Vaccine 100 µL equivalent | Fenoldopam mesylate | 100 | D1 activation | 30 |
| Ex. 961 | Sublingual | Solution | Recombinant HBs antigen protein | Vaccine 100 µL equivalent | Cisapride | 100 | 5-HT4 activation | 30 |
| Ex. 962 | Sublingual | Solution | Recombinant HBs antigen protein | Vaccine 100 µL equivalent | Desmopressin | 100 | V2 activation | 30 |
| Ex. 963 | Sublingual | Solution | Recombinant HBs antigen protein | Vaccine 100 µL equivalent | Prazosin hydrochloride | 400 | α1,2 antagonization | 30 |
| Ex. 964 | Sublingual | Solution | Recombinant HBs antigen protein | Vaccine 100 µL equivalent | Pirenzepine hycrochloride | 100 | M1 antagonization | 30 |
| Ex. 965 | Sublingual | Solution | Recombinant HBs antigen protein | Vaccine 100 µL equivalent | Oxybutynin hydrochloride | 200 | M2 antagonization | 30 |
| Ex. 966 | Sublingual | Solution | Recombinant HBs antigen protein | Vaccine 100 µL equivalent | Tolterodine tartrate | 400 | M3 antagonization | 30 |
| Ex. 967 | Sublingual | Solution | Recombinant HBs antigen protein | Vaccine 100 µL equivalent | Fluphenazine | 50 | D2 antagonization | 30 |
| Ex. 968 | Sublingual | Solution | Recombinant HBs antigen protein | Vaccine 100 µL equivalent | Droperidol | 100 | | 30 |
| Ex. 969 | Sublingual | Solution | Recombinant HBs antigen protein | Vaccine 100 µL equivalent | Sulpiride | 100 | | 30 |
| Ex. 970 | Sublingual | Solution | Recombinant HBs antigen protein | Vaccine 100 µL equivalent | Azelastine hydrochloride | 200 | H1 antagonization | 30 |
| Ex. 971 | Sublingual | Solution | Recombinant HBs antigen protein | Vaccine 100 µL equivalent | Levocetirizine | 100 | | 30 |
| Ex. 972 | Sublingual | Solution | Recombinant HBs antigen protein | Vaccine 100 µL equivalent | Mequitazine | 100 | | 30 |
| Ex. 973 | Sublingual | Solution | Recombinant HBs antigen protein | Vaccine 100 µL equivalent | Thioperamide | 100 | H3 antagonization | 30 |
| Ex. 974 | Sublingual | Solution | Recombinant HBs antigen protein | Vaccine 100 µL equivalent | Sarpogrelate hydrochloride | 100 | 5-HT2 antagonization | 30 |
| Ex. 975 | Sublingual | Solution | Recombinant HBs antigen protein | Vaccine 100 µL equivalent | Clopidogrel | 100 | P2Y12 antagonization | 30 |
| Ex. 976 | Sublingual | Solution | Recombinant HBs antigen protein | Vaccine 100 µL equivalent | Tiolopidine | 200 | | 30 |
| Ex. 977 | Sublingual | Solution | Recombinant HBs antigen protein | Vaccine 100 µL equivalent | Prasugrel | 100 | | 30 |
| Ex. 978 | Sublingual | Solution | Recombinant HBs antigen protein | Vaccine 100 µL equivalent | Apafant | 100 | PAF antagonization | 30 |
| Ex. 979 | Sublingual | Solution | Recombinant HBs antigen protein | Vaccine 100 µL equivalent | Naloxone | 100 | µ, κ, σ antagonization | 30 |
| Ex. 980 | Sublingual | Solution | Recombinant HBs antigen protein | Vaccine 100 µL equivalent | Zafirlukast | 100 | CysLT antagonization | 30 |
| Ex. 981 | Sublingual | Solution | Recombinant HBs antigen protein | Vaccine 100 µL equivalent | Montelukast | 100 | | 30 |
| Ex. 982 | Sublingual | Solution | Recombinant HBs antigen protein | Vaccine 100 µL equivalent | Pranlukast | 100 | | 30 |
| Ex. 983 | Sublingual | Solution | Recombinant HBs antigen protein | Vaccine 100 µL equivalent | Candesartan | 100 | AT1 antagonization | 30 |

TABLE 38

| | Administration route | Dosage form | Antigen Name | Amount [µg] | Th2 reaction promoter Name | Amount [µg] | Pharmacological effect | Amount [µL] |
|---|---|---|---|---|---|---|---|---|
| Comp. Ex. 55 | Transnasal | Solution | Live attenuated yellow fever virus | Vaccine 100 µL equivalent | — | — | | 10 |
| Ex. 984 | Transnasal | Solution | Live attenuated yellow fever virus | Vaccine 100 µL equivalent | Resveratrol | 40 | PDE inhibition | 10 |

TABLE 38-continued

| | Administration route | Dosage form | Antigen Name | Amount [µg] | Th2 reaction promoter Name | Amount [µg] | Pharmacological effect | Amount [µL] |
|---|---|---|---|---|---|---|---|---|
| Ex. 985 | Transnasal | Solution | Live attenuated yellow fever virus | Vaccine 100 µL equivalent | Vinpocetine | 20 | PDE inhibition | 10 |
| Ex. 986 | Transnasal | Solution | Live attenuated yellow fever virus | Vaccine 100 µL equivalent | Pimobendan | 20 | PDE inhibition | 10 |
| Ex. 987 | Transnasal | Solution | Live attenuated yellow fever virus | Vaccine 100 µL equivalent | BRL50481 | 20 | PDE inhibition | 10 |
| Ex. 988 | Transnasal | Solution | Live attenuated yellow fever virus | Vaccine 100 µL equivalent | Dipyridamole | 40 | PDE inhibition | 10 |
| Ex. 989 | Transnasal | Solution | Live attenuated yellow fever virus | Vaccine 100 µL equivalent | Methoxyphenamine hydrochloride | 20 | β2 activation | 10 |
| Ex. 990 | Transnasal | Solution | Live attenuated yellow fever virus | Vaccine 100 µL equivalent | Fenoldopam mesylate | 20 | D1 activation | 10 |
| Ex. 991 | Transnasal | Solution | Live attenuated yellow fever virus | Vaccine 100 µL equivalent | Cisapride | 20 | 5-HT4 activation | 10 |
| Ex. 992 | Transnasal | Solution | Live attenuated yellow fever virus | Vaccine 100 µL equivalent | Desmopressin | 20 | V2 activation | 10 |
| Ex. 993 | Transnasal | Solution | Live attenuated yellow fever virus | Vaccine 100 µL equivalent | Prazosin hydrochloride | 80 | α1,2 antagonization | 10 |
| Ex. 994 | Transnasal | Solution | Live attenuated yellow fever virus | Vaccine 100 µL equivalent | Pirenzepine hycrochloride | 20 | M1 antagonization | 10 |
| Ex. 995 | Transnasal | Solution | Live attenuated yellow fever virus | Vaccine 100 µL equivalent | Oxybutynin hydrochloride | 40 | M2 antagonization | 10 |
| Ex. 996 | Transnasal | Solution | Live attenuated yellow fever virus | Vaccine 100 µL equivalent | Tolterodine tartrate | 80 | M3 antagonization | 10 |
| Ex. 997 | Transnasal | Solution | Live attenuated yellow fever virus | Vaccine 100 µL equivalent | Fluphenazine | 10 | D2 antagonization | 10 |
| Ex. 998 | Transnasal | Solution | Live attenuated yellow fever virus | Vaccine 100 µL equivalent | Droperidol | 20 | | 10 |
| Ex. 999 | Transnasal | Solution | Live attenuated yellow fever virus | Vaccine 100 µL equivalent | Sulpiride | 20 | | 10 |
| Ex. 1000 | Transnasal | Solution | Live attenuated yellow fever virus | Vaccine 100 µL equivalent | Azelastine hydrochloride | 40 | H1 antagonization | 10 |
| Ex. 1001 | Transnasal | Solution | Live attenuated yellow fever virus | Vaccine 100 µL equivalent | Levocetirizine | 20 | | 10 |
| Ex. 1002 | Transnasal | Solution | Live attenuated yellow fever virus | Vaccine 100 µL equivalent | Mequitazine | 20 | | 10 |
| Ex. 1003 | Transnasal | Solution | Live attenuated yellow fever virus | Vaccine 100 µL equivalent | Thioperamide | 20 | H3 antagonization | 10 |
| Ex. 1004 | Transnasal | Solution | Live attenuated yellow fever virus | Vaccine 100 µL equivalent | Sarpogrelate hydrochloride | 20 | 5-HT2 antagonization | 10 |
| Ex. 1005 | Transnasal | Solution | Live attenuated yellow fever virus | Vaccine 100 µL equivalent | Clopidogrel | 20 | P2Y12 antagonization | 10 |
| Ex. 1006 | Transnasal | Solution | Live attenuated yellow fever virus | Vaccine 100 µL equivalent | Tiolopidine | 40 | | 10 |
| Ex. 1007 | Transnasal | Solution | Live attenuated yellow fever virus | Vaccine 100 µL equivalent | Prasugrel | 20 | | 10 |
| Ex. 1008 | Transnasal | Solution | Live attenuated yellow fever virus | Vaccine 100 µL equivalent | Apafant | 20 | PAF antagonization | 10 |
| Ex. 1009 | Transnasal | Solution | Live attenuated yellow fever virus | Vaccine 100 µL equivalent | Naloxone | 20 | µ, κ, σ antagonization | 10 |
| Ex. 1010 | Transnasal | Solution | Live attenuated yellow fever virus | Vaccine 100 µL equivalent | Zafirlukast | 20 | CysLT antagonization | 10 |
| Ex. 1011 | Transnasal | Solution | Live attenuated yellow fever virus | Vaccine 100 µL equivalent | Montelukast | 20 | | 10 |
| Ex. 1012 | Transnasal | Solution | Live attenuated yellow fever virus | Vaccine 100 µL equivalent | Pranlukast | 20 | | 10 |
| Ex. 1013 | Transnasal | Solution | Live attenuated yellow fever virus | Vaccine 100 µL equivalent | Candesartan | 20 | AT1 antagonization | 10 |

TABLE 39

| | Administration route | Dosage form | Antigen Name | Amount [µg] | Th2 reaction promoter Name | Amount [µg] | Pharmacological effect | Amount [µL] |
|---|---|---|---|---|---|---|---|---|
| Comp. Ex. 56 | Sublingual | Solution | Live attenuated yellow fever virus | Vaccine 100 µL equivalent | — | — | | 30 |
| Ex. 1014 | Sublingual | Solution | Live attenuated yellow fever virus | Vaccine 100 µL equivalent | Resveratrol | 200 | PDE inhibition | 30 |
| Ex. 1015 | Sublingual | Solution | Live attenuated yellow fever virus | Vaccine 100 µL equivalent | Vinpocetine | 100 | PDE inhibition | 30 |

TABLE 39-continued

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Ex. 1016 | Sublingual | Solution | Live attenuated yellow fever virus | Vaccine 100 μL equivalent | Pimobendan | 100 | PDE inhibition | 30 |
| Ex. 1017 | Sublingual | Solution | Live attenuated yellow fever virus | Vaccine 100 μL equivalent | BRL50481 | 100 | PDE inhibition | 30 |
| Ex. 1018 | Sublingual | Solution | Live attenuated yellow fever virus | Vaccine 100 μL equivalent | Dipyridamole | 200 | PDE inhibition | 30 |
| Ex. 1019 | Sublingual | Solution | Live attenuated yellow fever virus | Vaccine 100 μL equivalent | Methoxyphenamine hydrochloride | 100 | β2 activation | 30 |
| Ex. 1020 | Sublingual | Solution | Live attenuated yellow fever virus | Vaccine 100 μL equivalent | Fenoldopam mesylate | 100 | D1 activation | 30 |
| Ex. 1021 | Sublingual | Solution | Live attenuated yellow fever virus | Vaccine 100 μL equivalent | Cisapride | 100 | 5-HT4 activation | 30 |
| Ex. 1022 | Sublingual | Solution | Live attenuated yellow fever virus | Vaccine 100 μL equivalent | Desmopressin | 100 | V2 activation | 30 |
| Ex. 1023 | Sublingual | Solution | Live attenuated yellow fever virus | Vaccine 100 μL equivalent | Prazosin hydrochloride | 400 | α1,2 antagonization | 30 |
| Ex. 1024 | Sublingual | Solution | Live attenuated yellow fever virus | Vaccine 100 μL equivalent | Pirenzepine hycrochloride | 100 | M1 antagonization | 30 |
| Ex. 1025 | Sublingual | Solution | Live attenuated yellow fever virus | Vaccine 100 μL equivalent | Oxybutynin hydrochloride | 200 | M2 antagonization | 30 |
| Ex. 1026 | Sublingual | Solution | Live attenuated yellow fever virus | Vaccine 100 μL equivalent | Tolterodine tartrate | 400 | M3 antagonization | 30 |
| Ex. 1027 | Sublingual | Solution | Live attenuated yellow fever virus | Vaccine 100 μL equivalent | Fluphenazine | 50 | D2 antagonization | 30 |
| Ex. 1028 | Sublingual | Solution | Live attenuated yellow fever virus | Vaccine 100 μL equivalent | Droperidol | 100 | | 30 |
| Ex. 1029 | Sublingual | Solution | Live attenuated yellow fever virus | Vaccine 100 μL equivalent | Sulpiride | 100 | | 30 |
| Ex. 1030 | Sublingual | Solution | Live attenuated yellow fever virus | Vaccine 100 μL equivalent | Azelastine hydrochloride | 200 | H1 antagonization | 30 |
| Ex. 1031 | Sublingual | Solution | Live attenuated yellow fever virus | Vaccine 100 μL equivalent | Levocetirizine | 100 | | 30 |
| Ex. 1032 | Sublingual | Solution | Live attenuated yellow fever virus | Vaccine 100 μL equivalent | Mequitazine | 100 | | 30 |
| Ex. 1033 | Sublingual | Solution | Live attenuated yellow fever virus | Vaccine 100 μL equivalent | Thioperamide | 100 | H3 antagonization | 30 |
| Ex. 1034 | Sublingual | Solution | Live attenuated yellow fever virus | Vaccine 100 μL equivalent | Sarpogrelate hydrochloride | 100 | 5-HT2 antagonization | 30 |
| Ex. 1035 | Sublingual | Solution | Live attenuated yellow fever virus | Vaccine 100 μL equivalent | Clopidogrel | 100 | P2Y12 antagonization | 30 |
| Ex. 1036 | Sublingual | Solution | Live attenuated yellow fever virus | Vaccine 100 μL equivalent | Tiolopidine | 200 | | 30 |
| Ex. 1037 | Sublingual | Solution | Live attenuated yellow fever virus | Vaccine 100 μL equivalent | Prasugrel | 100 | | 30 |
| Ex. 1038 | Sublingual | Solution | Live attenuated yellow fever virus | Vaccine 100 μL equivalent | Apafant | 100 | PAF antagonization | 30 |
| Ex. 1039 | Sublingual | Solution | Live attenuated yellow fever virus | Vaccine 100 μL equivalent | Naloxone | 100 | μ, κ, σ antagonization | 30 |
| Ex. 1040 | Sublingual | Solution | Live attenuated yellow fever virus | Vaccine 100 μL equivalent | Zafirlukast | 100 | CysLT antagonization | 30 |
| Ex. 1041 | Sublingual | Solution | Live attenuated yellow fever virus | Vaccine 100 μL equivalent | Montelukast | 100 | | 30 |
| Ex. 1042 | Sublingual | Solution | Live attenuated yellow fever virus | Vaccine 100 μL equivalent | Pranlukast | 100 | | 30 |
| Ex. 1043 | Sublingual | Solution | Live attenuated yellow fever virus | Vaccine 100 μL equivalent | Candesartan | 100 | AT1 antagonization | 30 |

TABLE 40

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 57 | Transnasal | Solution | Tetanus toxoid | Vaccine 100 μL equivalent | — | — | | 10 |
| Ex. 1044 | Transnasal | Solution | Tetanus toxoid | Vaccine 100 μL equivalent | Resveratrol | 40 | PDE inhibition | 10 |
| Ex. 1045 | Transnasal | Solution | Tetanus toxoid | Vaccine 100 μL equivalent | Vinpocetine | 20 | PDE inhibition | 10 |
| Ex. 1046 | Transnasal | Solution | Tetanus toxoid | Vaccine 100 μL equivalent | Pimobendan | 20 | PDE inhibition | 10 |

TABLE 40-continued

| | Administration route | Dosage form | Antigen Name | Amount [μg] | Th2 reaction promoter Name | Amount [μg] | Pharmacological effect | Amount [μL] |
|---|---|---|---|---|---|---|---|---|
| Ex. 1047 | Transnasal | Solution | Tetanus toxoid | Vaccine 100 μL equivalent | BRL50481 | 20 | PDE inhibition | 10 |
| Ex. 1048 | Transnasal | Solution | Tetanus toxoid | Vaccine 100 μL equivalent | Dipyridamole | 40 | PDE inhibition | 10 |
| Ex. 1049 | Transnasal | Solution | Tetanus toxoid | Vaccine 100 μL equivalent | Methoxyphenamine hydrochloride | 20 | β2 activation | 10 |
| Ex. 1050 | Transnasal | Solution | Tetanus toxoid | Vaccine 100 μL equivalent | Fenoldopam mesylate | 20 | D1 activation | 10 |
| Ex. 1051 | Transnasal | Solution | Tetanus toxoid | Vaccine 100 μL equivalent | Cisapride | 20 | 5-HT4 activation | 10 |
| Ex. 1052 | Transnasal | Solution | Tetanus toxoid | Vaccine 100 μL equivalent | Desmopressin | 20 | V2 activation | 10 |
| Ex. 1053 | Transnasal | Solution | Tetanus toxoid | Vaccine 100 μL equivalent | Prazosin hydrochloride | 80 | α1,2 antagonization | 10 |
| Ex. 1054 | Transnasal | Solution | Tetanus toxoid | Vaccine 100 μL equivalent | Pirenzepine hycrochloride | 20 | M1 antagonization | 10 |
| Ex. 1055 | Transnasal | Solution | Tetanus toxoid | Vaccine 100 μL equivalent | Oxybutynin hydrochloride | 40 | M2 antagonization | 10 |
| Ex. 1056 | Transnasal | Solution | Tetanus toxoid | Vaccine 100 μL equivalent | Tolterodine tartrate | 80 | M3 antagonization | 10 |
| Ex. 1057 | Transnasal | Solution | Tetanus toxoid | Vaccine 100 μL equivalent | Fluphenazine | 10 | D2 antagonization | 10 |
| Ex. 1058 | Transnasal | Solution | Tetanus toxoid | Vaccine 100 μL equivalent | Droperidol | 20 | | 10 |
| Ex. 1059 | Transnasal | Solution | Tetanus toxoid | Vaccine 100 μL equivalent | Sulpiride | 20 | | 10 |
| Ex. 1060 | Transnasal | Solution | Tetanus toxoid | Vaccine 100 μL equivalent | Azelastine hydrochloride | 40 | H1 antagonization | 10 |
| Ex. 1061 | Transnasal | Solution | Tetanus toxoid | Vaccine 100 μL equivalent | Levocetirizine | 20 | | 10 |
| Ex. 1062 | Transnasal | Solution | Tetanus toxoid | Vaccine 100 μL equivalent | Mequitazine | 20 | | 10 |
| Ex. 1063 | Transnasal | Solution | Tetanus toxoid | Vaccine 100 μL equivalent | Thioperamide | 20 | H3 antagonization | 10 |
| Ex. 1064 | Transnasal | Solution | Tetanus toxoid | Vaccine 100 μL equivalent | Sarpogrelate hydrochloride | 20 | 5-HT2 antagonization | 10 |
| Ex. 1065 | Transnasal | Solution | Tetanus toxoid | Vaccine 100 μL equivalent | Clopidogrel | 20 | P2Y12 antagonization | 10 |
| Ex. 1066 | Transnasal | Solution | Tetanus toxoid | Vaccine 100 μL equivalent | Tiolopidine | 40 | | 10 |
| Ex. 1067 | Transnasal | Solution | Tetanus toxoid | Vaccine 100 μL equivalent | Prasugrel | 20 | | 10 |
| Ex. 1068 | Transnasal | Solution | Tetanus toxoid | Vaccine 100 μL equivalent | Apafant | 20 | PAF antagonization | 10 |
| Ex. 1069 | Transnasal | Solution | Tetanus toxoid | Vaccine 100 μL equivalent | Naloxone | 20 | μ, κ, σ antagonization | 10 |
| Ex. 1070 | Transnasal | Solution | Tetanus toxoid | Vaccine 100 μL equivalent | Zafirlukast | 20 | CysLT antagonization | 10 |
| Ex. 1071 | Transnasal | Solution | Tetanus toxoid | Vaccine 100 μL equivalent | Montelukast | 20 | | 10 |
| Ex. 1072 | Transnasal | Solution | Tetanus toxoid | Vaccine 100 μL equivalent | Pranlukast | 20 | | 10 |
| Ex. 1073 | Transnasal | Solution | Tetanus toxoid | Vaccine 100 μL equivalent | Candesartan | 20 | AT1 antagonization | 10 |

TABLE 41

| | Administration route | Dosage form | Antigen Name | Amount [μg] | Th2 reaction promoter Name | Amount [μg] | Pharmacological effect | Amount [μL] |
|---|---|---|---|---|---|---|---|---|
| Comp. Ex. 58 | Sublingual | Solution | Tetanus toxoid | Vaccine 100 μL equivalent | — | — | | 30 |
| Ex. 1074 | Sublingual | Solution | Tetanus toxoid | Vaccine 100 μL equivalent | Resveratrol | 200 | PDE inhibition | 30 |
| Ex. 1075 | Sublingual | Solution | Tetanus toxoid | Vaccine 100 μL equivalent | Vinpocetine | 100 | PDE inhibition | 30 |
| Ex. 1076 | Sublingual | Solution | Tetanus toxoid | Vaccine 100 μL equivalent | Pimobendan | 100 | PDE inhibition | 30 |
| Ex. 1077 | Sublingual | Solution | Tetanus toxoid | Vaccine 100 μL equivalent | BRL50481 | 100 | PDE inhibition | 30 |

TABLE 41-continued

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Ex. 1078 | Sublingual | Solution | Tetanus toxoid | Vaccine 100 μL equivalent | Dipyridamole | 200 | PDE inhibition | 30 |
| Ex. 1079 | Sublingual | Solution | Tetanus toxoid | Vaccine 100 μL equivalent | Methoxyphenamine hydrochloride | 100 | β2 activation | 30 |
| Ex. 1080 | Sublingual | Solution | Tetanus toxoid | Vaccine 100 μL equivalent | Fenoldopam mesylate | 100 | D1 activation | 30 |
| Ex. 1081 | Sublingual | Solution | Tetanus toxoid | Vaccine 100 μL equivalent | Cisapride | 100 | 5-HT4 activation | 30 |
| Ex. 1082 | Sublingual | Solution | Tetanus toxoid | Vaccine 100 μL equivalent | Desmopressin | 100 | V2 activation | 30 |
| Ex. 1083 | Sublingual | Solution | Tetanus toxoid | Vaccine 100 μL equivalent | Prazosin hydrochloride | 400 | α1,2 antagonization | 30 |
| Ex. 1084 | Sublingual | Solution | Tetanus toxoid | Vaccine 100 μL equivalent | Pirenzepine hycrochloride | 100 | M1 antagonization | 30 |
| Ex. 1085 | Sublingual | Solution | Tetanus toxoid | Vaccine 100 μL equivalent | Oxybutynin hydrochloride | 200 | M2 antagonization | 30 |
| Ex. 1086 | Sublingual | Solution | Tetanus toxoid | Vaccine 100 μL equivalent | Tolterodine tartrate | 400 | M3 antagonization | 30 |
| Ex. 1087 | Sublingual | Solution | Tetanus toxoid | Vaccine 100 μL equivalent | Fluphenazine | 50 | D2 antagonization | 30 |
| Ex. 1088 | Sublingual | Solution | Tetanus toxoid | Vaccine 100 μL equivalent | Droperidol | 100 | | 30 |
| Ex. 1089 | Sublingual | Solution | Tetanus toxoid | Vaccine 100 μL equivalent | Sulpiride | 100 | | 30 |
| Ex. 1090 | Sublingual | Solution | Tetanus toxoid | Vaccine 100 μL equivalent | Azelastine hydrochloride | 200 | H1 antagonization | 30 |
| Ex. 1091 | Sublingual | Solution | Tetanus toxoid | Vaccine 100 μL equivalent | Levocetirizine | 100 | | 30 |
| Ex. 1092 | Sublingual | Solution | Tetanus toxoid | Vaccine 100 μL equivalent | Mequitazine | 100 | | 30 |
| Ex. 1093 | Sublingual | Solution | Tetanus toxoid | Vaccine 100 μL equivalent | Thioperamide | 100 | H3 antagonization | 30 |
| Ex. 1094 | Sublingual | Solution | Tetanus toxoid | Vaccine 100 μL equivalent | Sarpogrelate hydrochloride | 100 | 5-HT2 antagonization | 30 |
| Ex. 1095 | Sublingual | Solution | Tetanus toxoid | Vaccine 100 μL equivalent | Clopidogrel | 100 | P2Y12 antagonization | 30 |
| Ex. 1096 | Sublingual | Solution | Tetanus toxoid | Vaccine 100 μL equivalent | Tiolopidine | 200 | | 30 |
| Ex. 1097 | Sublingual | Solution | Tetanus toxoid | Vaccine 100 μL equivalent | Prasugrel | 100 | | 30 |
| Ex. 1098 | Sublingual | Solution | Tetanus toxoid | Vaccine 100 μL equivalent | Apafant | 100 | PAF antagonization | 30 |
| Ex. 1099 | Sublingual | Solution | Tetanus toxoid | Vaccine 100 μL equivalent | Naloxone | 100 | μ, κ, σ antagonization | 30 |
| Ex. 1100 | Sublingual | Solution | Tetanus toxoid | Vaccine 100 μL equivalent | Zafirlukast | 100 | CysLT antagonization | 30 |
| Ex. 1101 | Sublingual | Solution | Tetanus toxoid | Vaccine 100 μL equivalent | Montelukast | 100 | | 30 |
| Ex. 1102 | Sublingual | Solution | Tetanus toxoid | Vaccine 100 μL equivalent | Pranlukast | 100 | | 30 |
| Ex. 1103 | Sublingual | Solution | Tetanus toxoid | Vaccine 100 μL equivalent | Candesartan | 100 | AT1 antagonization | 30 |

TABLE 42

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 59 | Transnasal | Solution | Live attenuated varicella virus | Vaccine 100 μL equivalent | — | — | | 10 |
| Ex. 1104 | Transnasal | Solution | Live attenuated varicella virus | Vaccine 100 μL equivalent | Resveratrol | 40 | PDE inhibition | 10 |
| Ex. 1105 | Transnasal | Solution | Live attenuated varicella virus | Vaccine 100 μL equivalent | Vinpocetine | 20 | PDE inhibition | 10 |
| Ex. 1106 | Transnasal | Solution | Live attenuated varicella virus | Vaccine 100 μL equivalent | Pimobendan | 20 | PDE inhibition | 10 |
| Ex. 1107 | Transnasal | Solution | Live attenuated varicella virus | Vaccine 100 μL equivalent | BRL50481 | 20 | PDE inhibition | 10 |
| Ex. 1108 | Transnasal | Solution | Live attenuated varicella virus | Vaccine 100 μL equivalent | Dipyridamole | 40 | PDE inhibition | 10 |

TABLE 42-continued

| | Administration route | Dosage form | Antigen Name | Amount [µg] | Th2 reaction promoter Name | Amount [µg] | Pharmacological effect | Amount [µL] |
|---|---|---|---|---|---|---|---|---|
| Ex. 1109 | Transnasal | Solution | Live attenuated varicella virus | Vaccine 100 µL equivalent

TABLE 43-continued

| | Administration route | Dosage form | Antigen Name | Amount [µg] | Th2 reaction promoter Name | Amount [µg] | Pharmacological effect | Amount [µL] |
|---|---|---|---|---|---|---|---|---|
| Ex. 1140 | Sublingual | Solution | Live attenuated varicella virus | Vaccine 100 µL equivalent | Fenoldopam mesylate | 100 | D1 activation | 30 |
| Ex. 1141 | Sublingual | Solution | Live attenuated varicella virus | Vaccine 100 µL equivalent | Cisapride | 100 | 5-HT4 activation | 30 |
| Ex. 1142 |

TABLE 44-continued

|  | Administration route | Dosage form | Antigen Name | Amount [μg] | Th2 reaction promoter Name | Amount [μg] | Pharmacological effect | Amount [μL] |
|---|---|---|---|---|---|---|---|---|
| Ex. 1171 | Transnasal | Solution | Live BCG Vaccine | 30 μL equivalent | Cisapride | 20 | 5-HT4 activation | 10 |
| Ex. 1172 | Transnasal | Solution | Live BCG Vaccine | 30 μL equivalent | Desmopressin | 20 | V2 activation | 10 |
| Ex. 1173 | Transnasal | Solution | Live BCG Vaccine | 30 μL equivalent | Prazosin hydrochloride | 80 | α1,2 antagonization | 10 |
| Ex. 1174 | Transnasal | Solution | Live BCG Vaccine | 30 μL equivalent | Pirenzepine hycrochloride | 20 | M1 antagonization | 10 |
| Ex. 1175 | Transnasal | Solution | Live BCG Vaccine | 30 μL equivalent | Oxybutynin hydrochloride | 40 | M2 antagonization | 10 |
| Ex. 1176 | Transnasal | Solution | Live BCG Vaccine | 30 μL equivalent | Tolterodine tartrate | 80 | M3 antagonization | 10 |
| Ex. 1177 | Transnasal | Solution | Live BCG Vaccine | 30 μL equivalent | Fluphenazine | 10 | D2 antagonization | 10 |
| Ex. 1178 | Transnasal | Solution | Live BCG Vaccine | 30 μL equivalent | Droperidol | 20 |  | 10 |
| Ex. 1179 | Transnasal | Solution | Live BCG Vaccine | 30 μL equivalent | Sulpiride | 20 |  | 10 |
| Ex. 1180 | Transnasal | Solution | Live BCG Vaccine | 30 μL equivalent | Azelastine hydrochloride | 40 | H1 antagonization | 10 |
| Ex. 1181 | Transnasal | Solution | Live BCG Vaccine | 30 μL equivalent | Levocetirizine | 20 |  | 10 |
| Ex. 1182 | Transnasal | Solution | Live BCG Vaccine | 30 μL equivalent | Mequitazine | 20 |  | 10 |
| Ex. 1183 | Transnasal | Solution | Live BCG Vaccine | 30 μL equivalent | Thioperamide | 20 | H3 antagonization | 10 |
| Ex. 1184 | Transnasal | Solution | Live BCG Vaccine | 30 μL equivalent | Sarpogrelate hydrochloride | 20 | 5-HT2 antagonization | 10 |
| Ex. 1185 | Transnasal | Solution | Live BCG Vaccine | 30 μL equivalent | Clopidogrel | 20 | P2Y12 antagonization | 10 |
| Ex. 1186 | Transnasal | Solution | Live BCG Vaccine | 30 μL equivalent | Tiolopidine | 40 |  | 10 |
| Ex. 1187 | Transnasal | Solution | Live BCG Vaccine | 30 μL equivalent | Prasugrel | 20 |  | 10 |
| Ex. 1188 | Transnasal | Solution | Live BCG Vaccine | 30 μL equivalent | Apafant | 20 | PAF antagonization | 10 |
| Ex. 1189 | Transnasal | Solution | Live BCG Vaccine | 30 μL equivalent | Naloxone | 20 | μ, κ, σ antagonization | 10 |
| Ex. 1190 | Transnasal | Solution | Live BCG Vaccine | 30 μL equivalent | Zafirlukast | 20 | CysLT antagonization | 10 |
| Ex. 1191 | Transnasal | Solution | Live BCG Vaccine | 30 μL equivalent | Montelukast | 20 |  | 10 |
| Ex. 1192 | Transnasal | Solution | Live BCG Vaccine | 30 μL equivalent | Pranlukast | 20 |  | 10 |
| Ex. 1193 | Transnasal | Solution | Live BCG Vaccine | 30 μL equivalent | Candesartan | 20 | AT1 antagonization | 10 |

TABLE 45

|  | Administration route | Dosage form | Antigen Name | Amount [μg] | Th2 reaction promoter Name | Amount [μg] | Pharmacological effect | Amount [μL] |
|---|---|---|---|---|---|---|---|---|
| Comp. Ex. 62 | Sublingual | Solution | Live BCG Vaccine | 30 μL equivalent | — | — |  | 30 |
| Ex. 1194 | Sublingual | Solution | Live BCG Vaccine | 30 μL equivalent | Resveratrol | 200 | PDE inhibition | 30 |
| Ex. 1195 | Sublingual | Solution | Live BCG Vaccine | 30 μL equivalent | Vinpocetine | 100 | PDE inhibition | 30 |
| Ex. 1196 | Sublingual | Solution | Live BCG Vaccine | 30 μL equivalent | Pimobendan | 100 | PDE inhibition | 30 |
| Ex. 1197 | Sublingual | Solution | Live BCG Vaccine | 30 μL equivalent | BRL50481 | 100 | PDE inhibition | 30 |
| Ex. 1198 | Sublingual | Solution | Live BCG Vaccine | 30 μL equivalent | Dipyridamole | 200 | PDE inhibition | 30 |
| Ex. 1199 | Sublingual | Solution | Live BCG Vaccine | 30 μL equivalent | Methoxyphenamine hydrochloride | 100 | β2 activation | 30 |
| Ex. 1200 | Sublingual | Solution | Live BCG Vaccine | 30 μL equivalent | Fenoldopam mesylate | 100 | D1 activation | 30 |
| Ex. 1201 | Sublingual | Solution | Live BCG Vaccine | 30 μL equivalent | Cisapride | 100 | 5-HT4 activation | 30 |

TABLE 45-continued

| | Administration route | Dosage form | Antigen Name | Amount [µg] | Th2 reaction promoter Name | Amount [µg] | Pharmacological effect | Amount [µL] |
|---|---|---|---|---|---|---|---|---|
| Ex. 1202 | Sublingual | Solution | Live BCG Vaccine | 30 µL equivalent | Desmopressin | 100 | V2 activation | 30 |
| Ex. 1203 | Sublingual | Solution | Live BCG Vaccine | 30 µL equivalent | Prazosin hydrochloride | 400 | α1,2 antagonization | 30 |
| Ex. 1204 | Sublingual | Solution | Live BCG Vaccine | 30 µL equivalent | Pirenzepine hycrochloride | 100 | M1 antagonization | 30 |
| Ex. 1205 | Sublingual | Solution | Live BCG Vaccine | 30 µL equivalent | Oxybutynin hydrochloride | 200 | M2 antagonization | 30 |
| Ex. 1206 | Sublingual | Solution | Live BCG Vaccine | 30 µL equivalent | Tolterodine tartrate | 400 | M3 antagonization | 30 |
| Ex. 1207 | Sublingual | Solution | Live BCG Vaccine | 30 µL equivalent | Fluphenazine | 50 | D2 antagonization | 30 |
| Ex. 1208 | Sublingual | Solution | Live BCG Vaccine | 30 µL equivalent | Droperidol | 100 | | 30 |
| Ex. 1209 | Sublingual | Solution | Live BCG Vaccine | 30 µL equivalent | Sulpiride | 100 | | 30 |
| Ex. 1210 | Sublingual | Solution | Live BCG Vaccine | 30 µL equivalent | Azelastine hydrochloride | 200 | H1 antagonization | 30 |
| Ex. 1211 | Sublingual | Solution | Live BCG Vaccine | 30 µL equivalent | Levocetirizine | 100 | | 30 |
| Ex. 1212 | Sublingual | Solution | Live BCG Vaccine | 30 µL equivalent | Mequitazine | 100 | | 30 |
| Ex. 1213 | Sublingual | Solution | Live BCG Vaccine | 30 µL equivalent | Thioperamide | 100 | H3 antagonization | 30 |
| Ex. 1214 | Sublingual | Solution | Live BCG Vaccine | 30 µL equivalent | Sarpogrelate hydrochloride | 100 | 5-HT2 antagonization | 30 |
| Ex. 1215 | Sublingual | Solution | Live BCG Vaccine | 30 µL equivalent | Clopidogrel | 100 | P2Y12 antagonization | 30 |
| Ex. 1216 | Sublingual | Solution | Live BCG Vaccine | 30 µL equivalent | Tiolopidine | 200 | | 30 |
| Ex. 1217 | Sublingual | Solution | Live BCG Vaccine | 30 µL equivalent | Prasugrel | 100 | | 30 |
| Ex. 1218 | Sublingual | Solution | Live BCG Vaccine | 30 µL equivalent | Apafant | 100 | PAF antagonization | 30 |
| Ex. 1219 | Sublingual | Solution | Live BCG Vaccine | 30 µL equivalent | Naloxone | 100 | µ, κ, σ antagonization | 30 |
| Ex. 1220 | Sublingual | Solution | Live BCG Vaccine | 30 µL equivalent | Zafirlukast | 100 | CysLT antagonization | 30 |
| Ex. 1221 | Sublingual | Solution | Live BCG Vaccine | 30 µL equivalent | Montelukast | 100 | | 30 |
| Ex. 1222 | Sublingual | Solution | Live BCG Vaccine | 30 µL equivalent | Pranlukast | 100 | | 30 |
| Ex. 1223 | Sublingual | Solution | Live BCG Vaccine | 30 µL equivalent | Candesartan | 100 | AT1 antagonization | 30 |

TABLE 46

| | Administration route | Dosage form | Antigen Name | Amount [µg] | Th2 reaction promoter Name | Amount [µg] | Pharmacological effect | Amount [µL] |
|---|---|---|---|---|---|---|---|---|
| Comp. Ex. 63 | Transnasal | Solution | Inactivated rabies virus | Vaccine 200 µL equivalent | — | — | | 10 |
| Ex. 1224 | Transnasal | Solution | Inactivated rabies virus | Vaccine 200 µL equivalent | Resveratrol | 40 | PDE inhibition | 10 |
| Ex. 1225 | Transnasal | Solution | Inactivated rabies virus | Vaccine 200 µL equivalent | Vinpocetine | 20 | PDE inhibition | 10 |
| Ex. 1226 | Transnasal | Solution | Inactivated rabies virus | Vaccine 200 µL equivalent | Pimobendan | 20 | PDE inhibition | 10 |
| Ex. 1227 | Transnasal | Solution | Inactivated rabies virus | Vaccine 200 µL equivalent | BRL50481 | 20 | PDE inhibition | 10 |
| Ex. 1228 | Transnasal | Solution | Inactivated rabies virus | Vaccine 200 µL equivalent | Dipyridamole | 40 | PDE inhibition | 10 |
| Ex. 1229 | Transnasal | Solution | Inactivated rabies virus | Vaccine 200 µL equivalent | Methoxyphenamine hydrochloride | 20 | β2 activation | 10 |
| Ex. 1230 | Transnasal | Solution | Inactivated rabies virus | Vaccine 200 µL equivalent | Fenoldopam mesylate | 20 | D1 activation | 10 |
| Ex. 1231 | Transnasal | Solution | Inactivated rabies virus | Vaccine 200 µL equivalent | Cisapride | 20 | 5-HT4 activation | 10 |
| Ex. 1232 | Transnasal | Solution | Inactivated rabies virus | Vaccine 200 µL equivalent | Desmopressin | 20 | V2 activation | 10 |

TABLE 46-continued

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Ex. 1233 | Transnasal | Solution | Inactivated rabies virus | Vaccine 200 μL equivalent | Prazosin hydrochloride | 80 | α1,2 antagonization | 10 |
| Ex. 1234 | Transnasal | Solution | Inactivated rabies virus | Vaccine 200 μL equivalent | Pirenzepine hycrochloride | 20 | M1 antagonization | 10 |
| Ex. 1235 | Transnasal | Solution | Inactivated rabies virus | Vaccine 200 μL equivalent | Oxybutynin hydrochloride | 40 | M2 antagonization | 10 |
| Ex. 1236 | Transnasal | Solution | Inactivated rabies virus | Vaccine 200 μL equivalent | Tolterodine tartrate | 80 | M3 antagonization | 10 |
| Ex. 1237 | Transnasal | Solution | Inactivated rabies virus | Vaccine 200 μL equivalent | Fluphenazine | 10 | D2 antagonization | 10 |
| Ex. 1238 | Transnasal | Solution | Inactivated rabies virus | Vaccine 200 μL equivalent | Droperidol | 20 | | 10 |
| Ex. 1239 | Transnasal | Solution | Inactivated rabies virus | Vaccine 200 μL equivalent | Sulpiride | 20 | | 10 |
| Ex. 1240 | Transnasal | Solution | Inactivated rabies virus | Vaccine 200 μL equivalent | Azelastine hydrochloride | 40 | H1 antagonization | 10 |
| Ex. 1241 | Transnasal | Solution | Inactivated rabies virus | Vaccine 200 μL equivalent | Levocetirizine | 20 | | 10 |
| Ex. 1242 | Transnasal | Solution | Inactivated rabies virus | Vaccine 200 μL equivalent | Mequitazine | 20 | | 10 |
| Ex. 1243 | Transnasal | Solution | Inactivated rabies virus | Vaccine 200 μL equivalent | Thioperamide | 20 | H3 antagonization | 10 |
| Ex. 1244 | Transnasal | Solution | Inactivated rabies virus | Vaccine 200 μL equivalent | Sarpogrelate hydrochloride | 20 | 5-HT2 antagonization | 10 |
| Ex. 1245 | Transnasal | Solution | Inactivated rabies virus | Vaccine 200 μL equivalent | Clopidogrel | 20 | P2Y12 antagonization | 10 |
| Ex. 1246 | Transnasal | Solution | Inactivated rabies virus | Vaccine 200 μL equivalent | Tiolopidine | 40 | | 10 |
| Ex. 1247 | Transnasal | Solution | Inactivated rabies virus | Vaccine 200 μL equivalent | Prasugrel | 20 | | 10 |
| Ex. 1248 | Transnasal | Solution | Inactivated rabies virus | Vaccine 200 μL equivalent | Apafant | 20 | PAF antagonization | 10 |
| Ex. 1249 | Transnasal | Solution | Inactivated rabies virus | Vaccine 200 μL equivalent | Naloxone | 20 | μ, κ, σ antagonization | 10 |
| Ex. 1250 | Transnasal | Solution | Inactivated rabies virus | Vaccine 200 μL equivalent | Zafirlukast | 20 | CysLT antagonization | 10 |
| Ex. 1251 | Transnasal | Solution | Inactivated rabies virus | Vaccine 200 μL equivalent | Montelukast | 20 | | 10 |
| Ex. 1252 | Transnasal | Solution | Inactivated rabies virus | Vaccine 200 μL equivalent | Pranlukast | 20 | | 10 |
| Ex. 1253 | Transnasal | Solution | Inactivated rabies virus | Vaccine 200 μL equivalent | Candesartan | 20 | AT1 antagonization | 10 |

TABLE 47

| | Administration route | Dosage form | Antigen Name | Antigen Amount [μg] | Th2 reaction promoter Name | Th2 reaction promoter Amount [μg] | Pharmacological effect | Amount [μL] |
|---|---|---|---|---|---|---|---|---|
| Comp. Ex. 64 | Sublingual | Solution | Inactivated rabies virus | Vaccine 200 μL equivalent | — | — | | 30 |
| Ex. 1254 | Sublingual | Solution | Inactivated rabies virus | Vaccine 200 μL equivalent | Resveratrol | 200 | PDE inhibition | 30 |
| Ex. 1255 | Sublingual | Solution | Inactivated rabies virus | Vaccine 200 μL equivalent | Vinpocetine | 100 | PDE inhibition | 30 |
| Ex. 1256 | Sublingual | Solution | Inactivated rabies virus | Vaccine 200 μL equivalent | Pimobendan | 100 | PDE inhibition | 30 |
| Ex. 1257 | Sublingual | Solution | Inactivated rabies virus | Vaccine 200 μL equivalent | BRL50481 | 100 | PDE inhibition | 30 |
| Ex. 1258 | Sublingual | Solution | Inactivated rabies virus | Vaccine 200 μL equivalent | Dipyridamole | 200 | PDE inhibition | 30 |
| Ex. 1259 | Sublingual | Solution | Inactivated rabies virus | Vaccine 200 μL equivalent | Methoxyphenamine hydrochloride | 100 | β2 activation | 30 |
| Ex. 1260 | Sublingual | Solution | Inactivated rabies virus | Vaccine 200 μL equivalent | Fenoldopam mesylate | 100 | D1 activation | 30 |
| Ex. 1261 | Sublingual | Solution | Inactivated rabies virus | Vaccine 200 μL equivalent | Cisapride | 100 | 5-HT4 activation | 30 |
| Ex. 1262 | Sublingual | Solution | Inactivated rabies virus | Vaccine 200 μL equivalent | Desmopressin | 100 | V2 activation | 30 |
| Ex. 1263 | Sublingual | Solution | Inactivated rabies virus | Vaccine 200 μL equivalent | Prazosin hydrochloride | 400 | α1,2 antagonization | 30 |

TABLE 47-continued

| | Administration route | Dosage form | Antigen Name | Amount [μg] | Th2 reaction promoter Name | Amount [μg] | Pharmacological effect | Amount [μL] |
|---|---|---|---|---|---|---|---|---|
| Ex. 1264 | Sublingual | Solution | Inactivated rabies virus | Vaccine 200 μL equivalent | Pirenzepine hycrochloride | 100 | M1 antagonization | 30 |
| Ex. 1265 | Sublingual | Solution | Inactivated rabies virus | Vaccine 200 μL equivalent | Oxybutynin hydrochloride | 200 | M2 antagonization | 30 |
| Ex. 1266 | Sublingual | Solution | Inactivated rabies virus | Vaccine 200 μL equivalent | Tolterodine tartrate | 400 | M3 antagonization | 30 |
| Ex. 1267 | Sublingual | Solution | Inactivated rabies virus | Vaccine 200 μL equivalent | Fluphenazine | 50 | D2 antagonization | 30 |
| Ex. 1268 | Sublingual | Solution | Inactivated rabies virus | Vaccine 200 μL equivalent | Droperidol | 100 | | 30 |
| Ex. 1269 | Sublingual | Solution | Inactivated rabies virus | Vaccine 200 μL equivalent | Sulpiride | 100 | | 30 |
| Ex. 1270 | Sublingual | Solution | Inactivated rabies virus | Vaccine 200 μL equivalent | Azelastine hydrochloride | 200 | H1 antagonization | 30 |
| Ex. 1271 | Sublingual | Solution | Inactivated rabies virus | Vaccine 200 μL equivalent | Levocetirizine | 100 | | 30 |
| Ex. 1272 | Sublingual | Solution | Inactivated rabies virus | Vaccine 200 μL equivalent | Mequitazine | 100 | | 30 |
| Ex. 1273 | Sublingual | Solution | Inactivated rabies virus | Vaccine 200 μL equivalent | Thioperamide | 100 | H3 antagonization | 30 |
| Ex. 1274 | Sublingual | Solution | Inactivated rabies virus | Vaccine 200 μL equivalent | Sarpogrelate hydrochloride | 100 | 5-HT2 antagonization | 30 |
| Ex. 1275 | Sublingual | Solution | Inactivated rabies virus | Vaccine 200 μL equivalent | Clopidogrel | 100 | P2Y12 antagonization | 30 |
| Ex. 1276 | Sublingual | Solution | Inactivated rabies virus | Vaccine 200 μL equivalent | Tiolopidine | 200 | | 30 |
| Ex. 1277 | Sublingual | Solution | Inactivated rabies virus | Vaccine 200 μL equivalent | Prasugrel | 100 | | 30 |
| Ex. 1278 | Sublingual | Solution | Inactivated rabies virus | Vaccine 200 μL equivalent | Apafant | 100 | PAF antagonization | 30 |
| Ex. 1279 | Sublingual | Solution | Inactivated rabies virus | Vaccine 200 μL equivalent | Naloxone | 100 | μ, κ, σ antagonization | 30 |
| Ex. 1280 | Sublingual | Solution | Inactivated rabies virus | Vaccine 200 μL equivalent | Zafirlukast | 100 | CysLT antagonization | 30 |
| Ex. 1281 | Sublingual | Solution | Inactivated rabies virus | Vaccine 200 μL equivalent | Montelukast | 100 | | 30 |
| Ex. 1282 | Sublingual | Solution | Inactivated rabies virus | Vaccine 200 μL equivalent | Pranlukast | 100 | | 30 |
| Ex. 1283 | Sublingual | Solution | Inactivated rabies virus | Vaccine 200 μL equivalent | Candesartan | 100 | AT1 antagonization | 30 |

The evaluation of the humoral immunity inducing effect shows that the transmucosal administration (transnasal administration) of a solution for transmucosal administration containing a Th2 reaction promoter (Examples 1 to 30) provides a higher antigen-specific IgG antibody titer than the administration of a solution for transmucosal administration free from a Th2 reaction promoter (Comparative Examples 1 to 8). Although the antigen and the Th2 reaction promoter in the examples were administered in the same formulation, the effect mentioned above can be obtained also when they are in separate formulations and administered separately. Not only in the case of the solution for transmucosal administration, but also in the case of other dosage forms such as solutions for subcutaneous administration or creams for transdermal administration, a high antigen-specific IgG antibody titer as mentioned above can be obtained by preparing an antigen and a Th2 reaction promoter as different formulations and administering them separately.

TABLE 48

| Additive | Amount [Parts by weight] |
|---|---|
| White Vaseline | 60.7 |
| Sorbitan monostearate | 0.7 |
| Isostearic acid | 12 |
| Benzyl alcohol | 2.4 |
| Cetanol | 2.4 |
| Stearyl alcohol | 3.5 |
| Polysorbate 60 | 3.5 |
| Concentrated glycerin | 2.4 |
| Purified water | 12.4 |
| Total | 100 |

The invention claimed is:

1. A method for promoting humoral immunity induction in a subject in need thereof, comprising:

administering to the subject an effective amount of a G protein-coupled receptor (GPCR) ligand that is at least one selected from an antagonist for a Gi-coupled GPCR and an antagonist for a Gq-coupled GPCR.

2. A method for promoting humoral immunity induction in a subject in need thereof, comprising:

administering to the subject an effective amount of a pharmaceutical composition comprising:

an antigen for humoral immunity induction; and
a G protein-coupled receptor (GPCR) ligand that is at least one selected from an antagonist for a Gi-coupled GPCR and an antagonist for a Gq-coupled GPCR.

3. The method according to claim 1, wherein the antagonist is selected from the group consisting of an adrenergic receptor antagonist, a muscarinic receptor antagonist, a dopamine receptor antagonist, a histamine receptor antagonist, a serotonin receptor antagonist, a PAF receptor antagonist, a purine receptor antagonist, a vasopressin receptor antagonist, an opioid receptor antagonist, a leukotriene receptor antagonist, and an angiotensin receptor antagonist.

* * * * *